US012742005B2

(12) United States Patent
Guo et al.

(10) Patent No.: US 12,742,005 B2
(45) Date of Patent: Sep. 22, 2026

(54) HUMAN IL-33 ANTIBODIES, PREPARATION METHOD AND CONJUGATES THEREOF AND METHOD OF USE THEREOF FOR TREATMENT

(71) Applicant: SUNSHINE GUOJIAN PHARMACEUTICAL (SHANGHAI) CO., LTD., Pudong New Area (CN)

(72) Inventors: Wei Guo, Pudong New Area (CN); Xuesai Zhang, Pudong New Area (CN); Huiting Xu, Pudong New Area (CN); Qingrou Li, Pudong New Area (CN); Le Zhao, Pudong New Area (CN); Jianhe Chen, Pudong New Area (CN); Haomin Huang, Pudong New Area (CN); Zhenping Zhu, Pudong New Area (CN)

(73) Assignee: SUNSHINE GUOJIAN PHARMACEUTICAL (SHANGHAI) CO., LTD., Shanghai (CN)

( * ) Notice: Subject to any disclaimer, the term of this patent is extended or adjusted under 35 U.S.C. 154(b) by 697 days.

(21) Appl. No.: 18/246,756

(22) PCT Filed: Sep. 26, 2021

(86) PCT No.: PCT/CN2021/120785
§ 371 (c)(1), (2) Date: Mar. 27, 2023

(87) PCT Pub. No.: WO2022/063281
PCT Pub. Date: Mar. 31, 2022

(65) Prior Publication Data

US 2023/0399394 A1 Dec. 14, 2023

(30) Foreign Application Priority Data

Sep. 25, 2020 (CN) ........................ 202011023301.8

(51) Int. Cl.
*C07K 16/24* (2006.01)
*A61P 37/02* (2006.01)
*C12N 15/63* (2006.01)

(52) U.S. Cl.
CPC ............ *C07K 16/244* (2013.01); *A61P 37/02* (2018.01); *C12N 15/63* (2013.01); *C07K 2317/14* (2013.01); *C07K 2317/565* (2013.01)

(58) Field of Classification Search
CPC .............. C07K 16/244; C07K 2317/14; C07K 2317/56524; C07K 2317/33; C07K 2317/34; C07K 2317/76; C07K 2317/90; C07K 2317/92; C07K 2317/52; C07K 2317/56; A61P 37/02; A61P 1/00; A61P 1/04; A61P 1/16; A61P 3/10; A61P 11/00; A61P 11/02; A61P 11/06; A61P 13/12; A61P 17/00; A61P 17/06; A61P 19/02; A61P 25/00; A61P 27/02; A61P 35/00; A61P 37/08; C12N 15/63; A61K 2039/505

See application file for complete search history.

(56) References Cited

U.S. PATENT DOCUMENTS

2020/0071396 A1 3/2020 Murphy et al.

FOREIGN PATENT DOCUMENTS

| | | | |
|---|---|---|---|
| AU | 2017-257330 | A1 | 10/2018 |
| CN | 105051063 | A | 11/2015 |
| CN | 105980556 | A | 9/2016 |
| CN | 106103480 | A | 11/2016 |
| CN | 111620948 | A | 9/2020 |
| JP | 6501650 | B2 | 4/2019 |

OTHER PUBLICATIONS

Paul, WE (1993) Fundamental Immunology, 3rd ed. Raven Press, NY, Chap. 9, pp. 292-295.*
Rudikoff, S et al. (1982) Proc. Natl. Acad. Sci. USA, 79:1979-1983 (doi: 10.1073/pnas.79.6.1979).*
Colman, PM (1994) Research in Immunology, Elsevier, NY, 145(1):33-36.*
Bendig M. M. (1995) Methods: A Companion to Methods in Enzymology, 8:83-93.*
MacCallum et al. (Oct. 11, 1996) J. Mol. Biol., 262(5):732-745. (doi: 10.1006/jmbi.1996.0548).*
Casset et al (2003) Biochemical and Biophysical Research Communications, 307:198-205. (doi: 10.1016/S0006-291X(03)01131-8).*
Chen et al. (1995) EMBO J., 14(12):2784-2794. (doi: 10.1002/j.1460-2075.1995.tb07278.x).*
Scheffer L, et al. (Nov. 2024) Briefings in Bioinformatics. 25(6):1-10. (https://doi.org/10.1093/bib/bbae537).*
Valdes-Trescano MS, et al. (2023) Molecules. 28(10):3991. pp. 1-7. (https://doi.org/10.3390/molecules28103991).*

(Continued)

*Primary Examiner* — Robert S Landsman
(74) *Attorney, Agent, or Firm* — Banner & Witcoff, Ltd.

(57) ABSTRACT

The present invention relates to an antibody binding to human IL-33 or an antigen-binding fragment thereof, which can bind to the human IL-33 with a high affinity and block the binding of ST2 to IL-33, can be used in the preparation of a drug for treating diseases with a high IL-33 expression (such as asthma, atopic/allergic dermatitis, chronic rhino sinusitis and chronic obstructive pulmonary diseases (COPD)), and has good clinical application prospects.

19 Claims, 11 Drawing Sheets

Specification includes a Sequence Listing.

(56) References Cited

OTHER PUBLICATIONS

Ye C, et al. JMIR Bioinform Biotechnol. Oct. 28, 2022;3(1):e29404. pp. 1-7. (doi: 10.2196/29404).*
Oboki et al., IL-33 and IL-33 Receptors in Host Defense and Diseases, Allergology International, vol. 59, pp. 143-160, 2010.
Partial Supplementary European Search Report issued Sep. 16, 2024 in European Patent Application No. 21871650.4.
Jan. 6, 2022—(WO) International Search Report and Written Opinion—App PCT/CN2021/120785.
Williams, D.G.; Matthews, D.J.; Jones, T. Humanising Antibodies by CDR Grafting. In Antibody Engineering; Kontermann, R., Dubel, S., Eds.; Springer: Berlin/Heidelberg, Germany, 2010; pp. 319-339. ISBN 978-3-642-01144-3.

* cited by examiner

SEQUENCE LISTING

```
<160> NUMBER OF SEQ ID NOS: 71

<210> SEQ ID NO 1
<211> LENGTH: 363
<212> TYPE: DNA
<213> ORGANISM: Mus musculus

<400> SEQUENCE: 1

caggtacagc tgaaggagtc aggacctggc ctggtggcgc cctcacagag cctgtccatc     60

acttgcactg tctctgggtt ttcattaacc aactatggtg tacactgggt tcgcctgcct    120

ccaggaaagg gtctggagtg gctgggagtg atacgagctg gtggaagttc agattataat    180

tcggctctca tgtccagact gaacatcagg aaagacaatt ccaagagcca agttttctta    240

gaaatgaaca gtcttcaaac tgctgacaca gccatgtact actgtgccag agaccattat    300

ttcagtaata gttacggggg ttctccttac tggggccaag ggactctggt cactgtctct    360

gca                                                                  363


<210> SEQ ID NO 2
<211> LENGTH: 121
<212> TYPE: PRT
<213> ORGANISM: Mus musculus

<400> SEQUENCE: 2

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Leu Pro Pro Gly Lys Gly Leu Glu Trp Leu
        35                  40                  45

Gly Val Ile Arg Ala Gly Gly Ser Ser Asp Tyr Asn Ser Ala Leu Met
    50                  55                  60

Ser Arg Leu Asn Ile Arg Lys Asp Asn Ser Lys Ser Gln Val Phe Leu
65                  70                  75                  80

Glu Met Asn Ser Leu Gln Thr Ala Asp Thr Ala Met Tyr Tyr Cys Ala
                85                  90                  95

Arg Asp His Tyr Phe Ser Asn Ser Tyr Gly Gly Ser Pro Tyr Trp Gly
            100                 105                 110

Gln Gly Thr Leu Val Thr Val Ser Ala
        115                 120
```

<210> SEQ ID NO 3
<211> LENGTH: 363
<212> TYPE: DNA
<213> ORGANISM: Mus musculus

<400> SEQUENCE: 3
caggttcacc tgaaggagtc agggcctggc ctggtggcgc cctcacagag cctgtccatc 60
acttgcaatg tctctggatt ttcattatcc aaatatggtg tacactggat ccgccagact 120
ccaggaaggg gtctggactg gctgggagtg ttacgggctg gtggaaccat aagttataat 180
tcggctctca tgtccagact gagtatcagc gaagacattt ccaaaagcca agttttctta 240
aaaatgaatg atttacaaac tgatgactca gccatctact tctgtgccag agaccattac 300
tactatagtt ccttcggggg ttttgcttcc tggggtcagg ggactctggt cactgtctct 360
gca 363

<210> SEQ ID NO 4
<211> LENGTH: 121
<212> TYPE: PRT
<213> ORGANISM: Mus musculus

<400> SEQUENCE: 4

Gln Val His Leu Lys Glu Ser Gly Pro Gly Leu Val Ala Pro Ser Gln
1 5 10 15

Ser Leu Ser Ile Thr Cys Asn Val Ser Gly Phe Ser Leu Ser Lys Tyr
20 25 30

Gly Val His Trp Ile Arg Gln Thr Pro Gly Arg Gly Leu Asp Trp Leu
35 40 45

Gly Val Leu Arg Ala Gly Gly Thr Ile Ser Tyr Asn Ser Ala Leu Met
50 55 60

Ser Arg Leu Ser Ile Ser Glu Asp Ile Ser Lys Ser Gln Val Phe Leu
65 70 75 80

Lys Met Asn Asp Leu Gln Thr Asp Asp Ser Ala Ile Tyr Phe Cys Ala
85 90 95

Arg Asp His Tyr Tyr Tyr Ser Ser Phe Gly Gly Phe Ala Ser Trp Gly
100 105 110

Gln Gly Thr Leu Val Thr Val Ser Ala
115 120

<210> SEQ ID NO 5
<211> LENGTH: 321
<212> TYPE: DNA
<213> ORGANISM: Mus musculus

<400> SEQUENCE: 5
gacattcaga tgacccagtc tcctgcctcc cagtctgcat ctctgggaga aagtgtcacc 60
atcacatgcc tggcaagtca gaccattgct acatggttag catggtatca gcagaaacca 120
gggaaatctc ctcagctcct gatttatgct gcaaccaggt tggcagatgg ggtcccatca 180
aggttcagtg gtagtggatc tggcacagaa ttttctttca agatcagtag cctacaggct 240
gaagattttg tgatttatta ctgtcaacaa ctttacaata ctccgtacac gttcggaggg 300
gggaccaagc tggagataaa a 321

<210> SEQ ID NO 6
<211> LENGTH: 107
<212> TYPE: PRT

<213> ORGANISM: Mus musculus

<400> SEQUENCE: 6

```
Asp Ile Gln Met Thr Gln Ser Pro Ala Ser Gln Ser Ala Ser Leu Gly
1               5                   10                  15

Glu Ser Val Thr Ile Thr Cys Leu Ala Ser Gln Thr Ile Ala Thr Trp
            20                  25                  30

Leu Ala Trp Tyr Gln Gln Lys Pro Gly Lys Ser Pro Gln Leu Leu Ile
        35                  40                  45

Tyr Ala Ala Thr Arg Leu Ala Asp Gly Val Pro Ser Arg Phe Ser Gly
    50                  55                  60

Ser Gly Ser Gly Thr Glu Phe Ser Phe Lys Ile Ser Ser Leu Gln Ala
65                  70                  75                  80

Glu Asp Phe Val Ile Tyr Tyr Cys Gln Gln Leu Tyr Asn Thr Pro Tyr
                85                  90                  95

Thr Phe Gly Gly Gly Thr Lys Leu Glu Ile Lys
            100                 105
```

<210> SEQ ID NO 7
<211> LENGTH: 363
<212> TYPE: DNA
<213> ORGANISM: Mus musculus

<400> SEQUENCE: 7

```
caggtgcaac tgaaggagtc aggacctggt ctggtggcgc cctcacacag cctgtccatc     60

acctgcaatg tctctgggtt ttcattatcc aagtatggtg tacactggat tcgtcagatt    120

ccaggaaggg gtctggactg gctgggagtg ttacgggctg gtggaagtac aggttataat    180

tcggctctca tgtccaggct gagtatcagc aaagacagtt ccaaaagcca agttttctta    240

aagatgaacg atctacggac tgatgacaca gccgtttact tctgtgtcag agaccattac    300

tactacagtt cttacggggg ttttgtttac tggggccagg ggactctggt cactgtctct    360

gca                                                                  363
```

<210> SEQ ID NO 8
<211> LENGTH: 121
<212> TYPE: PRT
<213> ORGANISM: Mus musculus

<400> SEQUENCE: 8

```
Gln Val Gln Leu Lys Glu Ser Gly Pro Gly Leu Val Ala Pro Ser His
1               5                   10                  15

Ser Leu Ser Ile Thr Cys Asn Val Ser Gly Phe Ser Leu Ser Lys Tyr
            20                  25                  30

Gly Val His Trp Ile Arg Gln Ile Pro Gly Arg Gly Leu Asp Trp Leu
        35                  40                  45

Gly Val Leu Arg Ala Gly Gly Ser Thr Gly Tyr Asn Ser Ala Leu Met
    50                  55                  60

Ser Arg Leu Ser Ile Ser Lys Asp Ser Ser Lys Ser Gln Val Phe Leu
65                  70                  75                  80

Lys Met Asn Asp Leu Arg Thr Asp Asp Thr Ala Val Tyr Phe Cys Val
                85                  90                  95

Arg Asp His Tyr Tyr Tyr Ser Ser Tyr Gly Gly Phe Val Tyr Trp Gly
            100                 105                 110

Gln Gly Thr Leu Val Thr Val Ser Ala
        115                 120
```

<210> SEQ ID NO 9
<211> LENGTH: 318
<212> TYPE: DNA
<213> ORGANISM: Mus musculus

<400> SEQUENCE: 9
gacattcaga tgacccagtc tcctgcctcc cagtctgcat ctctgggaga aagtgtcacc 60
atcacatgcc tggcaagtca gaccataggt gcatggttag catggtatcg gcagcaacca 120
ggaaaatctc ctcagctcct gatttatgct gcaaccaggt tggcagatgg ggtcccatca 180
aggttcagtg gtagtggttc tgggacagaa ttttctttca agatcaacaa cctacaggct 240
gaagattttg taagttatta ctgtcaacaa cttgacagta gtccgtacac gttcggaggg 300
gggaccaggc tggaaatg 318

<210> SEQ ID NO 10
<211> LENGTH: 106
<212> TYPE: PRT
<213> ORGANISM: Mus musculus

<400> SEQUENCE: 10

Asp Ile Gln Met Thr Gln Ser Pro Ala Ser Gln Ser Ala Ser Leu Gly
1 5 10 15

Glu Ser Val Thr Ile Thr Cys Leu Ala Ser Gln Thr Ile Gly Ala Trp
20 25 30

Leu Ala Trp Tyr Arg Gln Gln Pro Gly Lys Ser Pro Gln Leu Leu Ile
35 40 45

Tyr Ala Ala Thr Arg Leu Ala Asp Gly Val Pro Ser Arg Phe Ser Gly
50 55 60

Ser Gly Ser Gly Thr Glu Phe Ser Phe Lys Ile Asn Asn Leu Gln Ala
65 70 75 80

Glu Asp Phe Val Ser Tyr Tyr Cys Gln Gln Leu Asp Ser Ser Pro Tyr
85 90 95

Thr Phe Gly Gly Gly Thr Arg Leu Glu Met
100 105

<210> SEQ ID NO 11
<211> LENGTH: 318
<212> TYPE: DNA
<213> ORGANISM: Mus musculus

<400> SEQUENCE: 11
gacattcaga tgacccagtc tcctgcctcc cagtctgcat ctctgggaga aagtgtcacc 60
atcacatgcc tggcaagtca gaccattggt gcatggttag catggtatcg gcagcaacca 120
ggaaaatctc ctcagctcct gatttatgct gcaaccaggt tggcagatgg ggtcccatca 180
aggttcagtg gtagtggatc tggcacaaaa ttttctttca agatcaacaa cctacaggct 240
gaagattttg tgatttatta ctgtcaacaa cttaacagta ctccgtacac gttcggaggg 300
gggaccaggc tggaaatg 318

<210> SEQ ID NO 12
<211> LENGTH: 106
<212> TYPE: PRT
<213> ORGANISM: Mus musculus

<400> SEQUENCE: 12

Asp Ile Gln Met Thr Gln Ser Pro Ala Ser Gln Ser Ala Ser Leu Gly
1 5 10 15

```
Glu Ser Val Thr Ile Thr Cys Leu Ala Ser Gln Thr Ile Gly Ala Trp
            20                  25                  30

Leu Ala Trp Tyr Arg Gln Gln Pro Gly Lys Ser Pro Gln Leu Leu Ile
        35                  40                  45

Tyr Ala Ala Thr Arg Leu Ala Asp Gly Val Pro Ser Arg Phe Ser Gly
    50                  55                  60

Ser Gly Ser Gly Thr Lys Phe Ser Phe Lys Ile Asn Asn Leu Gln Ala
65                  70                  75                  80

Glu Asp Phe Val Ile Tyr Tyr Cys Gln Gln Leu Asn Ser Thr Pro Tyr
                85                  90                  95

Thr Phe Gly Gly Gly Thr Arg Leu Glu Met
            100                 105


<210> SEQ ID NO 13
<211> LENGTH: 327
<212> TYPE: PRT
<213> ORGANISM: Homo sapiens

<400> SEQUENCE: 13

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
```

```
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 14
<211> LENGTH: 107
<212> TYPE: PRT
<213> ORGANISM: Homo sapiens

<400> SEQUENCE: 14

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 15
<211> LENGTH: 5
<212> TYPE: PRT
<213> ORGANISM: Mus musculus

<400> SEQUENCE: 15

Asn Tyr Gly Val His
1               5


<210> SEQ ID NO 16
<211> LENGTH: 16
<212> TYPE: PRT
<213> ORGANISM: Mus musculus

<400> SEQUENCE: 16

Val Ile Arg Ala Gly Gly Ser Ser Asp Tyr Asn Ser Ala Leu Met Ser
1               5                   10                  15


<210> SEQ ID NO 17
<211> LENGTH: 13
<212> TYPE: PRT
<213> ORGANISM: Mus musculus

<400> SEQUENCE: 17

Asp His Tyr Phe Ser Asn Ser Tyr Gly Gly Ser Pro Tyr
1               5                   10


<210> SEQ ID NO 18
<211> LENGTH: 5
<212> TYPE: PRT
<213> ORGANISM: Mus musculus
```

<400> SEQUENCE: 18

Lys Tyr Gly Val His
1 5

<210> SEQ ID NO 19
<211> LENGTH: 16
<212> TYPE: PRT
<213> ORGANISM: Mus musculus

<400> SEQUENCE: 19

Val Leu Arg Ala Gly Gly Thr Ile Ser Tyr Asn Ser Ala Leu Met Ser
1 5 10 15

<210> SEQ ID NO 20
<211> LENGTH: 13
<212> TYPE: PRT
<213> ORGANISM: Mus musculus

<400> SEQUENCE: 20

Asp His Tyr Tyr Tyr Ser Ser Phe Gly Gly Phe Ala Ser
1 5 10

<210> SEQ ID NO 21
<211> LENGTH: 11
<212> TYPE: PRT
<213> ORGANISM: Mus musculus

<400> SEQUENCE: 21

Leu Ala Ser Gln Thr Ile Ala Thr Trp Leu Ala
1 5 10

<210> SEQ ID NO 22
<211> LENGTH: 7
<212> TYPE: PRT
<213> ORGANISM: Mus musculus

<400> SEQUENCE: 22

Ala Ala Thr Arg Leu Ala Asp
1 5

<210> SEQ ID NO 23
<211> LENGTH: 9
<212> TYPE: PRT
<213> ORGANISM: Mus musculus

<400> SEQUENCE: 23

Gln Gln Leu Tyr Asn Thr Pro Tyr Thr
1 5

<210> SEQ ID NO 24
<211> LENGTH: 16
<212> TYPE: PRT
<213> ORGANISM: Mus musculus

<400> SEQUENCE: 24

Val Leu Arg Ala Gly Gly Ser Thr Gly Tyr Asn Ser Ala Leu Met Ser
1 5 10 15

<210> SEQ ID NO 25
<211> LENGTH: 13
<212> TYPE: PRT
<213> ORGANISM: Mus musculus

<400> SEQUENCE: 25

-continued

```
Asp His Tyr Tyr Tyr Ser Ser Tyr Gly Gly Phe Val Tyr
1               5                   10


<210> SEQ ID NO 26
<211> LENGTH: 11
<212> TYPE: PRT
<213> ORGANISM: Mus musculus

<400> SEQUENCE: 26

Leu Ala Ser Gln Thr Ile Gly Ala Trp Leu Ala
1               5                   10


<210> SEQ ID NO 27
<211> LENGTH: 9
<212> TYPE: PRT
<213> ORGANISM: Mus musculus

<400> SEQUENCE: 27

Gln Gln Leu Asp Ser Ser Pro Tyr Thr
1               5


<210> SEQ ID NO 28
<211> LENGTH: 9
<212> TYPE: PRT
<213> ORGANISM: Mus musculus

<400> SEQUENCE: 28

Gln Gln Leu Asn Ser Thr Pro Tyr Thr
1               5


<210> SEQ ID NO 29
<211> LENGTH: 121
<212> TYPE: PRT
<213> ORGANISM: Artificial Sequence
<220> FEATURE:
<223> OTHER INFORMATION: Humanized variable fragment

<400> SEQUENCE: 29

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Val His Trp Ile Arg Gln Pro Pro Gly Lys Gly Leu Glu Trp Ile
        35                  40                  45

Gly Val Ile Arg Ala Gly Gly Ser Ser Asp Tyr Asn Ser Ala Leu Met
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp His Tyr Phe Ser Asn Ser Tyr Gly Gly Ser Pro Tyr Trp Gly
            100                 105                 110

Gln Gly Thr Leu Val Thr Val Ser Ser
        115                 120


<210> SEQ ID NO 30
<211> LENGTH: 121
<212> TYPE: PRT
<213> ORGANISM: Artificial Sequence
<220> FEATURE:
<223> OTHER INFORMATION: Humanized variable fragment

<400> SEQUENCE: 30
```

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Val His Trp Ile Arg Leu Pro Pro Gly Lys Gly Leu Glu Trp Ile
        35                  40                  45

Gly Val Ile Arg Ala Gly Gly Ser Ser Asp Tyr Asn Ser Ala Leu Met
    50                  55                  60

Ser Arg Val Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Asp His Tyr Phe Ser Asn Ser Tyr Gly Gly Ser Pro Tyr Trp Gly
            100                 105                 110

Gln Gly Thr Leu Val Thr Val Ser Ser
        115                 120
```

<210> SEQ ID NO 31
<211> LENGTH: 121
<212> TYPE: PRT
<213> ORGANISM: Artificial Sequence
<220> FEATURE:
<223> OTHER INFORMATION: Humanized variable fragment

<400> SEQUENCE: 31

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Val His Trp Val Arg Leu Pro Pro Gly Lys Gly Leu Glu Trp Leu
        35                  40                  45

Gly Val Ile Arg Ala Gly Gly Ser Ser Asp Tyr Asn Ser Ala Leu Met
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Asp His Tyr Phe Ser Asn Ser Tyr Gly Gly Ser Pro Tyr Trp Gly
            100                 105                 110

Gln Gly Thr Leu Val Thr Val Ser Ser
        115                 120
```

<210> SEQ ID NO 32
<211> LENGTH: 107
<212> TYPE: PRT
<213> ORGANISM: Artificial Sequence
<220> FEATURE:
<223> OTHER INFORMATION: Humanized variable fragment

<400> SEQUENCE: 32

```
Asp Ile Gln Met Thr Gln Ser Pro Ser Ser Leu Ser Ala Ser Val Gly
1               5                   10                  15

Asp Arg Val Thr Ile Thr Cys Leu Ala Ser Gln Thr Ile Ala Thr Trp
            20                  25                  30

Leu Ala Trp Tyr Gln Gln Lys Pro Gly Lys Ser Pro Lys Leu Leu Ile
        35                  40                  45

Tyr Ala Ala Thr Arg Leu Ala Asp Gly Val Pro Ser Arg Phe Ser Gly
```

```
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Tyr Asn Thr Pro Tyr
                85                  90                  95

Thr Phe Gly Gln Gly Thr Lys Val Glu Ile Lys
            100                 105


<210> SEQ ID NO 33
<211> LENGTH: 121
<212> TYPE: PRT
<213> ORGANISM: Artificial Sequence
<220> FEATURE:
<223> OTHER INFORMATION: Humanized variable fragment

<400> SEQUENCE: 33

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Lys Tyr
            20                  25                  30

Gly Val His Trp Ile Arg Gln Pro Pro Gly Lys Gly Leu Glu Trp Ile
        35                  40                  45

Gly Val Leu Arg Ala Gly Gly Thr Ile Ser Tyr Asn Ser Ala Leu Met
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp His Tyr Tyr Tyr Ser Ser Phe Gly Gly Phe Ala Ser Trp Gly
            100                 105                 110

Gln Gly Thr Leu Val Thr Val Ser Ser
        115                 120


<210> SEQ ID NO 34
<211> LENGTH: 121
<212> TYPE: PRT
<213> ORGANISM: Artificial Sequence
<220> FEATURE:
<223> OTHER INFORMATION: Humanized variable fragment

<400> SEQUENCE: 34

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Lys Tyr
            20                  25                  30

Gly Val His Trp Ile Arg Gln Pro Pro Gly Lys Gly Leu Glu Trp Ile
        35                  40                  45

Gly Val Leu Arg Ala Gly Gly Thr Ile Ser Tyr Asn Ser Ala Leu Met
    50                  55                  60

Ser Arg Val Thr Ile Ser Glu Asp Ile Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Asp His Tyr Tyr Tyr Ser Ser Phe Gly Gly Phe Ala Ser Trp Gly
            100                 105                 110

Gln Gly Thr Leu Val Thr Val Ser Ser
        115                 120
```

<210> SEQ ID NO 35
<211> LENGTH: 121
<212> TYPE: PRT
<213> ORGANISM: Artificial Sequence
<220> FEATURE:
<223> OTHER INFORMATION: Humanized variable fragment

<400> SEQUENCE: 35

Gln Val Gln Leu Gln Glu Ser Gly Pro Gly Leu Val Lys Pro Ser Glu
1 5 10 15

Thr Leu Ser Leu Thr Cys Thr Val Ser Gly Phe Ser Leu Ser Lys Tyr
20 25 30

Gly Val His Trp Ile Arg Gln Pro Pro Gly Lys Gly Leu Glu Trp Leu
35 40 45

Gly Val Leu Arg Ala Gly Gly Thr Ile Ser Tyr Asn Ser Ala Leu Met
50 55 60

Ser Arg Leu Thr Ile Ser Glu Asp Ile Ser Lys Ser Gln Val Ser Leu
65 70 75 80

Lys Leu Ser Ser Val Thr Ala Ala Asp Thr Ala Val Tyr Tyr Cys Ala
85 90 95

Arg Asp His Tyr Tyr Tyr Ser Ser Phe Gly Gly Phe Ala Ser Trp Gly
100 105 110

Gln Gly Thr Leu Val Thr Val Ser Ser
115 120

<210> SEQ ID NO 36
<211> LENGTH: 107
<212> TYPE: PRT
<213> ORGANISM: Artificial Sequence
<220> FEATURE:
<223> OTHER INFORMATION: Humanized variable fragment

<400> SEQUENCE: 36

Asp Ile Gln Met Thr Gln Ser Pro Ser Ser Val Ser Ala Ser Val Gly
1 5 10 15

Asp Arg Val Thr Ile Thr Cys Leu Ala Ser Gln Thr Ile Gly Ala Trp
20 25 30

Leu Ala Trp Tyr Gln Gln Lys Pro Gly Lys Ser Pro Lys Leu Leu Ile
35 40 45

Tyr Ala Ala Thr Arg Leu Ala Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Leu Asn Ser Thr Pro Tyr
85 90 95

Thr Phe Gly Gln Gly Thr Lys Val Glu Ile Lys
100 105

<210> SEQ ID NO 37
<211> LENGTH: 121
<212> TYPE: PRT
<213> ORGANISM: Artificial Sequence
<220> FEATURE:
<223> OTHER INFORMATION: Humanized variable fragment

<400> SEQUENCE: 37

Gln Val Gln Leu Gln Glu Ser Gly Pro Gly Leu Val Lys Pro Ser Glu
1 5 10 15

Thr Leu Ser Leu Thr Cys Thr Val Ser Gly Phe Ser Leu Ser Lys Tyr

```
            20                  25                  30

Gly Val His Trp Ile Arg Gln Pro Pro Gly Lys Gly Leu Glu Trp Ile
        35                  40                  45

Gly Val Leu Arg Ala Gly Gly Ser Thr Gly Tyr Asn Ser Ala Leu Met
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp His Tyr Tyr Tyr Ser Ser Tyr Gly Gly Phe Val Tyr Trp Gly
            100                 105                 110

Gln Gly Thr Leu Val Thr Val Ser Ser
        115                 120


<210> SEQ ID NO 38
<211> LENGTH: 121
<212> TYPE: PRT
<213> ORGANISM: Artificial Sequence
<220> FEATURE:
<223> OTHER INFORMATION: Humanized variable fragment

<400> SEQUENCE: 38

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Lys Tyr
            20                  25                  30

Gly Val His Trp Ile Arg Gln Pro Pro Gly Lys Gly Leu Glu Trp Ile
        35                  40                  45

Gly Val Leu Arg Ala Gly Gly Ser Thr Gly Tyr Asn Ser Ala Leu Met
    50                  55                  60

Ser Arg Val Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Asp His Tyr Tyr Tyr Ser Ser Tyr Gly Gly Phe Val Tyr Trp Gly
            100                 105                 110

Gln Gly Thr Leu Val Thr Val Ser Ser
        115                 120


<210> SEQ ID NO 39
<211> LENGTH: 121
<212> TYPE: PRT
<213> ORGANISM: Artificial Sequence
<220> FEATURE:
<223> OTHER INFORMATION: Humanized variable fragment

<400> SEQUENCE: 39

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Lys Tyr
            20                  25                  30

Gly Val His Trp Ile Arg Gln Pro Pro Gly Lys Gly Leu Glu Trp Leu
        35                  40                  45

Gly Val Leu Arg Ala Gly Gly Ser Thr Gly Tyr Asn Ser Ala Leu Met
    50                  55                  60

Ser Arg Leu Thr Ile Ser Lys Asp Ser Ser Lys Ser Gln Val Ser Leu
65                  70                  75                  80
```

-continued

```
Lys Leu Ser Ser Val Thr Ala Ala Asp Thr Ala Val Tyr Tyr Cys Val
                85                  90                  95

Arg Asp His Tyr Tyr Tyr Ser Ser Tyr Gly Gly Phe Val Tyr Trp Gly
            100                 105                 110

Gln Gly Thr Leu Val Thr Val Ser Ser
        115                 120


<210> SEQ ID NO 40
<211> LENGTH: 107
<212> TYPE: PRT
<213> ORGANISM: Artificial Sequence
<220> FEATURE:
<223> OTHER INFORMATION: Humanized variable fragment

<400> SEQUENCE: 40

Asp Ile Gln Met Thr Gln Ser Pro Ser Ser Val Ser Ala Ser Val Gly
1               5                   10                  15

Asp Arg Val Thr Ile Thr Cys Leu Ala Ser Gln Thr Ile Gly Ala Trp
            20                  25                  30

Leu Ala Trp Tyr Gln Gln Lys Pro Gly Lys Ser Pro Lys Leu Leu Ile
        35                  40                  45

Tyr Ala Ala Thr Arg Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asp Ser Ser Pro Tyr
                85                  90                  95

Thr Phe Gly Gln Gly Thr Lys Val Glu Ile Lys
            100                 105


<210> SEQ ID NO 41
<211> LENGTH: 363
<212> TYPE: DNA
<213> ORGANISM: Artificial Sequence
<220> FEATURE:
<223> OTHER INFORMATION: Humanized variable fragment

<400> SEQUENCE: 41

caggtgcagc tgcaggagtc tggaccaggc ctggtgaagc cttctgagac cctgagcctg      60

acctgtaccg tgtccggctt tagcctgaca aattatggcg tgcattggat tagacagcca     120

cctggcaagg gcctggagtg gattggcgtg attagagctg gaggttcctc tgattataat     180

tctgctctga tgtctagggt gaccattagt gtggatacat ctaagaatca gttttctctg     240

aagctgagtt ctgtgactgc cgctgataca gctgtgtatt attgtgctag ggaccattat     300

ttttctaata gctacggcgg cagtccttac tggggccagg gcacactggt gaccgtgtct     360

agc                                                                   363


<210> SEQ ID NO 42
<211> LENGTH: 363
<212> TYPE: DNA
<213> ORGANISM: Artificial Sequence
<220> FEATURE:
<223> OTHER INFORMATION: Humanized variable fragment

<400> SEQUENCE: 42

caggtgcagc tgcaggagag cggccctgga ctggtgaagc catctgagac tctgagcctg      60

acctgtacag tgagcggatt ttctctgact aattacggag tgcattggat tagactgcct     120

ccaggaaagg gcctggaatg gatcggtgtg attagagccg gaggctcctc tgattataat     180
```

-continued tccgctttga tgtctagagt gaccatctct aaagataact ctaagagtca ggtgtctctg 240
aagctgagta gcgtgacagc agctgatacc gctgtgtatt actgcgccag ggatcattac 300
ttttcaaact cttatggagg atctccttac tggggccagg gcaccctggt gacagtgagc 360
tct 363

<210> SEQ ID NO 43
<211> LENGTH: 363
<212> TYPE: DNA
<213> ORGANISM: Artificial Sequence
<220> FEATURE:
<223> OTHER INFORMATION: Humanized variable fragment

<400> SEQUENCE: 43
caggtgcagc tgcaggagtc tggccccggc ctggtgaagc cctccgagac cctgagcctg 60
acttgcactg tgagtggctt tagtctgact aattatggcg tgcattgggt gaggctgcct 120
ccaggcaagg gactggagtg gctgggagtg attagagctg gtggatctag tgattataac 180
tccgctctga tgtccagact gaccatctct aaggacaact ccaagagcca ggtgtccctg 240
aagctgtcta gtgtgaccgc cgccgacacc gccgtgtact actgcgccag ggaccactac 300
ttttctaact cttacggggg ctccccctac tggggccagg gcaccttggt gacagtgtct 360
agc 363

<210> SEQ ID NO 44
<211> LENGTH: 321
<212> TYPE: DNA
<213> ORGANISM: Artificial Sequence
<220> FEATURE:
<223> OTHER INFORMATION: Humanized variable fragment

<400> SEQUENCE: 44
gatattcaga tgacacagtc tccttcttct ctgtctgctt ctgtgggaga tagagtgacc 60
attacctgcc tggcttctca gaccattgcc acatggctgg cttggtatca gcagaagcct 120
ggaaagagcc ctaagctgct gatctatgct gctacaagac tggctgatgg cgtgccatct 180
agattctccg gatctggatc cggaacagac ttcaccctga caatctcttc tctgcagcct 240
gaggatttcg ctacctacta ttgccagcag ctgtataata ctccttatac atttggccag 300
ggcaccaagg tcgaaatcaa g 321

<210> SEQ ID NO 45
<211> LENGTH: 363
<212> TYPE: DNA
<213> ORGANISM: Artificial Sequence
<220> FEATURE:
<223> OTHER INFORMATION: Humanized variable fragment

<400> SEQUENCE: 45
caggtgcagc tgcaggaatc tggacctgga ctggtgaagc catccgagac actgtctctg 60
acatgtacag tgtctggctt ttctctgtct aagtatggag tgcattggat cagacagcct 120
cctggcaagg gcctggagtg gattggagtg ctgagagctg gcggaacaat tagttataat 180
tctgctctga tgtctagagt gaccatcagc gtggatacct ctaagaacca gttttctctg 240
aagctgagtt ctgtgacagc agccgacact gctgtgtact actgtgctcg cgaccactac 300
tactacagct ctttcggcgg cttcgcctcc tgggggcagg gcaccctggt gaccgtgtcc 360
tcc 363

<210> SEQ ID NO 46
<211> LENGTH: 363
<212> TYPE: DNA
<213> ORGANISM: Artificial Sequence
<220> FEATURE:
<223> OTHER INFORMATION: Humanized variable fragment

<400> SEQUENCE: 46
caggtgcagc tgcaggagtc cggccctggc ctggtgaagc cctccgagac cctgagcctg 60
acctgcaccg tgtccggctt ctccctgtcc aagtacggcg tgcactggat caggcagcct 120
cccggcaagg gcctggagtg gattggcgtt ctgagagctg gaggcactat ttcttataat 180
agcgcactga tgtctagagt gacaatcagt gaggatatct ctaagtccca ggtgagcctg 240
aagttaagtt ctgtgacagc tgctgacacc gctgtgtatt attgtgctag ggatcattac 300
tactactctt ccttcggcgg ctttgcctct tggggccagg gcaccctggt taccgtgagt 360
agt 363

<210> SEQ ID NO 47
<211> LENGTH: 363
<212> TYPE: DNA
<213> ORGANISM: Artificial Sequence
<220> FEATURE:
<223> OTHER INFORMATION: Humanized variable fragment

<400> SEQUENCE: 47
caggtgcagc tgcaggagag cggccccggc ctggtgaagc cctccgagac cctgagcctg 60
acctgcaccg tgtccggctt ttccctgagc aagtacggcg tgcactggat ccgccagccc 120
cccggcaagg gcctggagtg gctgggcgtg ctgagggccg gcggcaccat cagctacaac 180
tccgccctga tgtcccggct gaccatctct gaggacatct ccaagtccca ggtgtccctg 240
aagctgagct ccgtgaccgc cgccgacacc gccgtgtact actgcgcccg cgaccactac 300
tactacagca gcttcggcgg ctttgccagc tggggacagg gcaccctggt gaccgtgagc 360
agc 363

<210> SEQ ID NO 48
<211> LENGTH: 321
<212> TYPE: DNA
<213> ORGANISM: Artificial Sequence
<220> FEATURE:
<223> OTHER INFORMATION: Humanized variable fragment

<400> SEQUENCE: 48
gacatccaga tgacccagtc cccctcctcc gtgtcggcca gcgtgggcga cagagtgacc 60
atcacctgcc tggcctccca gacgatcggc gcctggctgg cctggtacca gcagaagccc 120
ggcaagtccc ccaagctgct gatctacgcc gccaccagac tggccgacgg cgtgccctcc 180
aggttcagcg gctccggatc tggtaccgat tttaccctga caatctctag cctgcagcct 240
gaggattttg ccacatacta ctgtcagcag ctgaatagta ctccatacac ctttggccag 300
ggaaccaagg tggagatcaa g 321

<210> SEQ ID NO 49
<211> LENGTH: 363
<212> TYPE: DNA
<213> ORGANISM: Artificial Sequence
<220> FEATURE:
<223> OTHER INFORMATION: Humanized variable fragment

<400> SEQUENCE: 49

-continued caggtgcagc tgcaggagtc cggccccggc ctggtgaagc catccgagac cctgagcctt 60
acctgcaccg tgtctggctt cagcctgtct aagtacggcg tgcattggat caggcagccc 120
cccggcaagg gcctggagtg gatcggcgtg ctgagagccg gcggcagcac aggctacaac 180
tccgccctga tgagcagggt gaccatcagc gtggacacca gcaagaacca gtttagcctg 240
aagctgagca gcgtgaccgc cgccgacacc gccgtgtact actgcgctcg ggaccactac 300
tactactcca gctacggcgg cttcgtgtac tggggccagg gcaccctggt gaccgtgtct 360
agc 363

<210> SEQ ID NO 50
<211> LENGTH: 363
<212> TYPE: DNA
<213> ORGANISM: Artificial Sequence
<220> FEATURE:
<223> OTHER INFORMATION: Humanized variable fragment

<400> SEQUENCE: 50
caggtgcagc tgcaggagtc tggccctgga ctggtgaagc cttctgagac actgagtctg 60
acatgtacag tgagtggctt ctctctgtcg aagtatggag tgcactggat taggcagccc 120
cctggaaagg gcctggagtg gatcggcgtg ctgcgggccg gcggctctac gggctacaac 180
tccgccctga tgagccgggt gaccatcagc aaggacacct ccaagagcca ggtgagcctg 240
aagctgtcta gcgtgaccgc cgccgacacc gccgtgtact actgcgccag ggaccactac 300
tactattcca gctatggcgg cttcgtgtac tggggccagg gcaccctggt gaccgtgtcc 360
tcc 363

<210> SEQ ID NO 51
<211> LENGTH: 363
<212> TYPE: DNA
<213> ORGANISM: Artificial Sequence
<220> FEATURE:
<223> OTHER INFORMATION: Humanized variable fragment

<400> SEQUENCE: 51
caggtgcagc tgcaggagag cggcccaggc ctggtgaagc catctgaaac cctgtctctg 60
acctgtacag tgtccggctt ttccctgtct aaatacggtg tgcactggat cagacagcct 120
cctggtaaag gcctggagtg gctgggagtg ctgagggctg gaggaagtac cggctataat 180
agcgctctga tgtctagatt gactatctct aaggatagct ctaaatctca ggtgagcctg 240
aaactgagct ctgtcaccgc tgccgatacc gctgtttatt attgtgtgag ggatcattac 300
tactactcct cttacggagg atttgtgtat tggggtcagg gcacactggt gacagtctcc 360
tct 363

<210> SEQ ID NO 52
<211> LENGTH: 321
<212> TYPE: DNA
<213> ORGANISM: Artificial Sequence
<220> FEATURE:
<223> OTHER INFORMATION: Humanized variable fragment

<400> SEQUENCE: 52
gacatccaga tgacacagtc tcctagctct gtgagcgctt ctgtgggaga tagagtgaca 60
atcacctgtc tggcttctca gaccattgga gcttggctgg cttggtacca gcagaaacca 120
ggcaagtctc ctaagctgct gatctatgct gctactagac tggctgatgg cgtgccatct 180

-continued agattttctg gcagcggatc tggaaccgat tttacactga caatctcttc tctgcagcct 240
gaggatttcg ctacatacta ttgtcagcag ctggattctt ctccttacac atttggccag 300
ggaacaaagg tggaaattaa g 321

<210> SEQ ID NO 53
<211> LENGTH: 166
<212> TYPE: PRT
<213> ORGANISM: Artificial Sequence
<220> FEATURE:
<223> OTHER INFORMATION: Human IL-33-his

<400> SEQUENCE: 53

Met Ser Ile Thr Gly Ile Ser Pro Ile Thr Glu Tyr Leu Ala Ser Leu
1 5 10 15

Ser Thr Tyr Asn Asp Gln Ser Ile Thr Phe Ala Leu Glu Asp Glu Ser
20 25 30

Tyr Glu Ile Tyr Val Glu Asp Leu Lys Lys Asp Glu Lys Lys Asp Lys
35 40 45

Val Leu Leu Ser Tyr Tyr Glu Ser Gln His Pro Ser Asn Glu Ser Gly
50 55 60

Asp Gly Val Asp Gly Lys Met Leu Met Val Thr Leu Ser Pro Thr Lys
65 70 75 80

Asp Phe Trp Leu His Ala Asn Asn Lys Glu His Ser Val Glu Leu His
85 90 95

Lys Cys Glu Lys Pro Leu Pro Asp Gln Ala Phe Phe Val Leu His Asn
100 105 110

Met His Ser Asn Cys Val Ser Phe Glu Cys Lys Thr Asp Pro Gly Val
115 120 125

Phe Ile Gly Val Lys Asp Asn His Leu Ala Leu Ile Lys Val Asp Ser
130 135 140

Ser Glu Asn Leu Cys Thr Glu Asn Ile Leu Phe Lys Leu Ser Glu Thr
145 150 155 160

His His His His His His
165

<210> SEQ ID NO 54
<211> LENGTH: 560
<212> TYPE: PRT
<213> ORGANISM: Artificial Sequence
<220> FEATURE:
<223> OTHER INFORMATION: ST2-Fc protein

<400> SEQUENCE: 54

Met Gly Phe Trp Ile Leu Ala Ile Leu Thr Ile Leu Met Tyr Ser Thr
1 5 10 15

Ala Ala Lys Phe Ser Lys Gln Ser Trp Gly Leu Glu Asn Glu Ala Leu
20 25 30

Ile Val Arg Cys Pro Arg Gln Gly Lys Pro Ser Tyr Thr Val Asp Trp
35 40 45

Tyr Tyr Ser Gln Thr Asn Lys Ser Ile Pro Thr Gln Glu Arg Asn Arg
50 55 60

Val Phe Ala Ser Gly Gln Leu Leu Lys Phe Leu Pro Ala Ala Val Ala
65 70 75 80

Asp Ser Gly Ile Tyr Thr Cys Ile Val Arg Ser Pro Thr Phe Asn Arg
85 90 95

Thr Gly Tyr Ala Asn Val Thr Ile Tyr Lys Lys Gln Ser Asp Cys Asn
100 105 110

-continued

```
Val Pro Asp Tyr Leu Met Tyr Ser Thr Val Ser Gly Ser Glu Lys Asn
        115                 120                 125

Ser Lys Ile Tyr Cys Pro Thr Ile Asp Leu Tyr Asn Trp Thr Ala Pro
    130                 135                 140

Leu Glu Trp Phe Lys Asn Cys Gln Ala Leu Gln Gly Ser Arg Tyr Arg
145                 150                 155                 160

Ala His Lys Ser Phe Leu Val Ile Asp Asn Val Met Thr Glu Asp Ala
                165                 170                 175

Gly Asp Tyr Thr Cys Lys Phe Ile His Asn Glu Asn Gly Ala Asn Tyr
            180                 185                 190

Ser Val Thr Ala Thr Arg Ser Phe Thr Val Lys Asp Glu Gln Gly Phe
        195                 200                 205

Ser Leu Phe Pro Val Ile Gly Ala Pro Ala Gln Asn Glu Ile Lys Glu
    210                 215                 220

Val Glu Ile Gly Lys Asn Ala Asn Leu Thr Cys Ser Ala Cys Phe Gly
225                 230                 235                 240

Lys Gly Thr Gln Phe Leu Ala Ala Val Leu Trp Gln Leu Asn Gly Thr
                245                 250                 255

Lys Ile Thr Asp Phe Gly Glu Pro Arg Ile Gln Gln Glu Glu Gly Gln
            260                 265                 270

Asn Gln Ser Phe Ser Asn Gly Leu Ala Cys Leu Asp Met Val Leu Arg
        275                 280                 285

Ile Ala Asp Val Lys Glu Glu Asp Leu Leu Leu Gln Tyr Asp Cys Leu
    290                 295                 300

Ala Leu Asn Leu His Gly Leu Arg Arg His Thr Val Arg Leu Ser Arg
305                 310                 315                 320

Lys Asn Pro Ser Lys Glu Cys Phe Glu Asn Leu Tyr Phe Gln Gly Thr
                325                 330                 335

His Thr Cys Pro Pro Cys Pro Ala Pro Glu Leu Leu Gly Gly Pro Ser
            340                 345                 350

Val Phe Leu Phe Pro Pro Lys Pro Lys Asp Thr Leu Met Ile Ser Arg
        355                 360                 365

Thr Pro Glu Val Thr Cys Val Val Val Asp Val Ser His Glu Asp Pro
    370                 375                 380

Glu Val Lys Phe Asn Trp Tyr Val Asp Gly Val Glu Val His Asn Ala
385                 390                 395                 400

Lys Thr Lys Pro Arg Glu Glu Gln Tyr Asn Ser Thr Tyr Arg Val Val
                405                 410                 415

Ser Val Leu Thr Val Leu His Gln Asp Trp Leu Asn Gly Lys Glu Tyr
            420                 425                 430

Lys Cys Lys Val Ser Asn Lys Ala Leu Pro Ala Pro Ile Glu Lys Thr
        435                 440                 445

Ile Ser Lys Ala Lys Gly Gln Pro Arg Glu Pro Gln Val Tyr Thr Leu
    450                 455                 460

Pro Pro Ser Arg Asp Glu Leu Thr Lys Asn Gln Val Ser Leu Thr Cys
465                 470                 475                 480

Leu Val Lys Gly Phe Tyr Pro Ser Asp Ile Ala Val Glu Trp Glu Ser
                485                 490                 495

Asn Gly Gln Pro Glu Asn Asn Tyr Lys Thr Thr Pro Pro Val Leu Asp
            500                 505                 510

Ser Asp Gly Ser Phe Phe Leu Tyr Ser Lys Leu Thr Val Asp Lys Ser
        515                 520                 525
```

-continued

```
Arg Trp Gln Gln Gly Asn Val Phe Ser Cys Ser Val Met His Glu Ala
    530                 535                 540

Leu His Asn His Tyr Thr Gln Lys Ser Leu Ser Leu Ser Pro Gly Lys
545                 550                 555                 560


<210> SEQ ID NO 55
<211> LENGTH: 160
<212> TYPE: PRT
<213> ORGANISM: Homo sapiens

<400> SEQUENCE: 55

Met Ser Ile Thr Gly Ile Ser Pro Ile Thr Glu Tyr Leu Ala Ser Leu
1               5                   10                  15

Ser Thr Tyr Asn Asp Gln Ser Ile Thr Phe Ala Leu Glu Asp Glu Ser
            20                  25                  30

Tyr Glu Ile Tyr Val Glu Asp Leu Lys Lys Asp Glu Lys Lys Asp Lys
        35                  40                  45

Val Leu Leu Ser Tyr Tyr Glu Ser Gln His Pro Ser Asn Glu Ser Gly
    50                  55                  60

Asp Gly Val Asp Gly Lys Met Leu Met Val Thr Leu Ser Pro Thr Lys
65                  70                  75                  80

Asp Phe Trp Leu His Ala Asn Asn Lys Glu His Ser Val Glu Leu His
                85                  90                  95

Lys Cys Glu Lys Pro Leu Pro Asp Gln Ala Phe Phe Val Leu His Asn
            100                 105                 110

Met His Ser Asn Cys Val Ser Phe Glu Cys Lys Thr Asp Pro Gly Val
        115                 120                 125

Phe Ile Gly Val Lys Asp Asn His Leu Ala Leu Ile Lys Val Asp Ser
    130                 135                 140

Ser Glu Asn Leu Cys Thr Glu Asn Ile Leu Phe Lys Leu Ser Glu Thr
145                 150                 155                 160


<210> SEQ ID NO 56
<211> LENGTH: 20
<212> TYPE: PRT
<213> ORGANISM: Artificial Sequence
<220> FEATURE:
<223> OTHER INFORMATION: Pep1

<400> SEQUENCE: 56

Val Gln Lys Tyr Thr Arg Ala Leu His Asp Ser Ser Ile Thr Gly Ile
1               5                   10                  15

Ser Pro Ile Thr
            20


<210> SEQ ID NO 57
<211> LENGTH: 20
<212> TYPE: PRT
<213> ORGANISM: Artificial Sequence
<220> FEATURE:
<223> OTHER INFORMATION: Pep2

<400> SEQUENCE: 57

Ser Ser Ile Thr Gly Ile Ser Pro Ile Thr Glu Tyr Leu Ala Ser Leu
1               5                   10                  15

Ser Thr Tyr Asn
            20


<210> SEQ ID NO 58
<211> LENGTH: 20
```

<212> TYPE: PRT
<213> ORGANISM: Artificial Sequence
<220> FEATURE:
<223> OTHER INFORMATION: Pep3

<400> SEQUENCE: 58

Glu Tyr Leu Ala Ser Leu Ser Thr Tyr Asn Asp Gln Ser Ile Thr Phe
1 5 10 15

Ala Leu Glu Asp
20

<210> SEQ ID NO 59
<211> LENGTH: 20
<212> TYPE: PRT
<213> ORGANISM: Artificial Sequence
<220> FEATURE:
<223> OTHER INFORMATION: Pep4

<400> SEQUENCE: 59

Asp Gln Ser Ile Thr Phe Ala Leu Glu Asp Glu Ser Tyr Glu Ile Tyr
1 5 10 15

Val Glu Asp Leu
20

<210> SEQ ID NO 60
<211> LENGTH: 20
<212> TYPE: PRT
<213> ORGANISM: Artificial Sequence
<220> FEATURE:
<223> OTHER INFORMATION: Pep5

<400> SEQUENCE: 60

Glu Ser Tyr Glu Ile Tyr Val Glu Asp Leu Lys Lys Asp Glu Lys Lys
1 5 10 15

Asp Lys Val Leu
20

<210> SEQ ID NO 61
<211> LENGTH: 20
<212> TYPE: PRT
<213> ORGANISM: Artificial Sequence
<220> FEATURE:
<223> OTHER INFORMATION: Pep6

<400> SEQUENCE: 61

Lys Lys Asp Glu Lys Lys Asp Lys Val Leu Leu Ser Tyr Tyr Glu Ser
1 5 10 15

Gln His Pro Ser
20

<210> SEQ ID NO 62
<211> LENGTH: 20
<212> TYPE: PRT
<213> ORGANISM: Artificial Sequence
<220> FEATURE:
<223> OTHER INFORMATION: Pep7

<400> SEQUENCE: 62

Leu Ser Tyr Tyr Glu Ser Gln His Pro Ser Asn Glu Ser Gly Asp Gly
1 5 10 15

Val Asp Gly Lys
20

<210> SEQ ID NO 63

<211> LENGTH: 20
<212> TYPE: PRT
<213> ORGANISM: Artificial Sequence
<220> FEATURE:
<223> OTHER INFORMATION: Pep8

<400> SEQUENCE: 63

```
Asn Glu Ser Gly Asp Gly Val Asp Gly Lys Met Leu Met Val Thr Leu
1               5                   10                  15

Ser Pro Thr Lys
            20
```

<210> SEQ ID NO 64
<211> LENGTH: 20
<212> TYPE: PRT
<213> ORGANISM: Artificial Sequence
<220> FEATURE:
<223> OTHER INFORMATION: Pep9

<400> SEQUENCE: 64

```
Met Leu Met Val Thr Leu Ser Pro Thr Lys Asp Phe Trp Leu His Ala
1               5                   10                  15

Asn Asn Lys Glu
            20
```

<210> SEQ ID NO 65
<211> LENGTH: 20
<212> TYPE: PRT
<213> ORGANISM: Artificial Sequence
<220> FEATURE:
<223> OTHER INFORMATION: Pep10

<400> SEQUENCE: 65

```
Asp Phe Trp Leu His Ala Asn Asn Lys Glu His Ser Val Glu Leu His
1               5                   10                  15

Lys Cys Glu Lys
            20
```

<210> SEQ ID NO 66
<211> LENGTH: 20
<212> TYPE: PRT
<213> ORGANISM: Artificial Sequence
<220> FEATURE:
<223> OTHER INFORMATION: Pep11

<400> SEQUENCE: 66

```
His Ser Val Glu Leu His Lys Cys Glu Lys Pro Leu Pro Asp Gln Ala
1               5                   10                  15

Phe Phe Val Leu
            20
```

<210> SEQ ID NO 67
<211> LENGTH: 20
<212> TYPE: PRT
<213> ORGANISM: Artificial Sequence
<220> FEATURE:
<223> OTHER INFORMATION: Pep12

<400> SEQUENCE: 67

```
Pro Leu Pro Asp Gln Ala Phe Phe Val Leu His Asn Met His Ser Asn
1               5                   10                  15

Cys Val Ser Phe
            20
```

-continued

```
<210> SEQ ID NO 68
<211> LENGTH: 20
<212> TYPE: PRT
<213> ORGANISM: Artificial Sequence
<220> FEATURE:
<223> OTHER INFORMATION: Pep13

<400> SEQUENCE: 68

His Asn Met His Ser Asn Cys Val Ser Phe Glu Cys Lys Thr Asp Pro
1               5                   10                  15

Gly Val Phe Ile
            20


<210> SEQ ID NO 69
<211> LENGTH: 20
<212> TYPE: PRT
<213> ORGANISM: Artificial Sequence
<220> FEATURE:
<223> OTHER INFORMATION: Pep14

<400> SEQUENCE: 69

Glu Cys Lys Thr Asp Pro Gly Val Phe Ile Gly Val Lys Asp Asn His
1               5                   10                  15

Leu Ala Leu Ile
            20


<210> SEQ ID NO 70
<211> LENGTH: 20
<212> TYPE: PRT
<213> ORGANISM: Artificial Sequence
<220> FEATURE:
<223> OTHER INFORMATION: Pep15

<400> SEQUENCE: 70

Gly Val Lys Asp Asn His Leu Ala Leu Ile Lys Val Asp Ser Ser Glu
1               5                   10                  15

Asn Leu Cys Thr
            20


<210> SEQ ID NO 71
<211> LENGTH: 20
<212> TYPE: PRT
<213> ORGANISM: Artificial Sequence
<220> FEATURE:
<223> OTHER INFORMATION: Pep16

<400> SEQUENCE: 71

Lys Val Asp Ser Ser Glu Asn Leu Cys Thr Glu Asn Ile Leu Phe Lys
1               5                   10                  15

Leu Ser Glu Thr
            20
```

HUMAN IL-33 ANTIBODIES, PREPARATION METHOD AND CONJUGATES THEREOF AND METHOD OF USE THEREOF FOR TREATMENT

CROSS REFERENCE TO RELATED APPLICATIONS

This application is a national stage application (under 35 U.S.C. § 371) of PCT/CN2021/120785, filed on Sep. 26, 2021, which claims the benefit of Chinese Patent Application No. 202011023301.8 filed Sep. 25, 2020, each of which is incorporated herein by reference in its entirety.

The instant application contains a Sequence Listing which has been submitted electronically in ASCII format and is hereby incorporated by reference in its entirety. Said ASCII copy, created on Apr. 17, 2023, is named "18246756_sub-SL.txt" and is 49,734 bytes in size.

TECHNICAL FIELD

The present invention belongs to the field of biotechnology, and specifically relates to an antibody binding to human IL-33, preparation method thereof, and use thereof.

BACKGROUND

Interleukin 33 (IL-33) is a multifunctional cytokine and a new member of the IL-1 family. It is encoded by the IL-33 gene, and is constitutively expressed in structural cells such as smooth muscle cells, epithelial cells, and endothelial cells, and can be induced by inflammatory cytokines in macrophages and dendritic cells. Studies have found that IL-33 is a bifunctional protein. On the one hand, IL-33 is localized in the nucleus and acts as a transcription factor. On the other hand, IL-33 is secreted outside the cell and acts as a cytokine by interacting with its receptor ST2. As a cytokine, IL-33 is a TH-2 type cytokine, which is considered as an alarm cytokine, inducing TH-2 cells to secrete IL-4, IL-5, IL-13 and other TH-2 cytokines by binding to ST2. In addition, IL-33 can also induce mast cells and basophils to secrete inflammatory cytokines and chemokines, such as IL-1β, IL-6, IL-8 and TNF-α, et al., and induce NK cells and NKT cells to secrete TH-1 type cytokines, such as IFγ, et al.

Asthma is also known as bronchial asthma. Bronchial asthma is a chronic airway inflammation involving many cells and cell components. Asthma has long been considered to be airway inflammation driven by CD4+Th-2 cells. However, anti-CD4 antibodies almost completely depleted CD4+ cells but did not completely reduce the production of IL-4, IL-5, or IL-13 in the lungs of asthmatic mice, suggesting that other cellular sources of these Th-2 cytokines must be present. IL-33 can produce IL-5 and IL-13 from ILC2s which expresses ST2, suggesting that IL-33 can induce the increase of IL-5-induced eosinophilias and the IL-13-induced mucous production even in the absence of Th-2 cells. In addition, the expression level of IL-33 in the lung of asthmatic patients is higher than that of healthy people, and the expression of IL-33 in the lung tissue of severe asthmatic patients is particularly obvious. IL-33 promotes collagen synthesis of asthmatic fibroblasts in children with severe asthma, suggesting that IL-33 plays a role in the development of characteristic airway remodeling in severe asthma. Allergic airway inflammation can be reduced by treatment with anti-IL-33 antibodies. Since IL-33 can activate Th-2 cells that express ST2, IL-5 and IL-13 produced by Th-2 and ILC2 cells are involved in the pathogenesis of asthma. These findings suggest that IL-33 may mediate the bridge between innate and acquired immunity, resulting the development of a severe asthma phenotype. In addition to asthma, the IL-33 pathway is involved in the treatment of a variety of conditions such as idiosyncratic/allergic dermatitis, arthritis, chronic sinusitis, chronic obstructive pulmonary disease (COPD), systemic sclerosis, liver fibrosis, psoriasis, ulcerative colitis, Crohn's disease, multiple sclerosis, diabetic kidney disease, inflammatory bowel disease, psoriasis, eosinophilic esophagitis, diabetic macular edema, age-related macular degeneration, xerophthalmus, tumors, etc. The present invention provides an IL-33 inhibitor that binds to IL-33 in a high-affinity manner and effectively neutralizes IL-33 activity.

SUMMARY OF THE INVENTION

In order to solve the above technical problems, the inventor of the present invention carried out a large number of tests, from antigen immunity, hybridoma screening, antibody expression and purification to biological activity identification, screened and obtained murine antibody specifically binding to human IL-33. On this basis, chimeric antibody and humanized antibody were constructed and obtained.

Accordingly, the object of the present invention is to provide an antibody binding to human IL-33 or an antigen-binding fragment thereof; to provide a nucleotide molecule encoding the antibody binding to human IL-33 or the antigen-binding fragment thereof; to provide an expression vector comprising the nucleotide molecule; to provide a host cell of the expression vector; to provide a preparation method of the antibody binding to human IL-33 or the antigen-binding fragment thereof; to provide a pharmaceutical composition comprising the antibody binding to human IL-33 or the antigen-binding fragment thereof; to provide a use of the antibody binding to human IL-33 or the antigen-binding fragment thereof in the preparation of drugs.

In order to achieve the above objects, the present invention adopts the following technical solutions:

On the one hand, the present invention provides an antibody binding to human IL-33 or the antigen-binding fragment thereof, wherein the affinity $EC_{50}$ of the antibody binding to human IL-33 or the antigen-binding fragment thereof is less than 1 nM.

In another preferred embodiment, the light chain of the antibody has a L-CDR2 with an amino acid sequence shown in SEQ ID No: 22, and has the following characteristics:

(t1) Blocking the binding of IL-33 to receptor ST2;

(t2) Inhibiting IL-6 secretion of HUVEC cells induced by IL-33;

(t3) Inhibiting IFNγ secretion of human PBMCs induced by IL-33 protein;

(t4) Inhibiting IFNγ secretion of NK cells induced by IL-33; and (t5) Inhibiting IL-5 and IL13 secretion of KU812 cells induced by IL-33.

In another preferred embodiment, the Kd value of the antibody against human IL33 is much smaller than that against mouse IL33 (the difference is 20 times or more).

In another preferred embodiment, the antibody comprises:

(a) heavy chain complementary determining regions H-CDR1, H-CDR2, H-CDR3, wherein the amino acid sequence of H-CDR1 is shown in SEQ ID NO: 18 or a variant with at most 2 amino acid substitution mutations in SEQ ID NO: 18; the amino acid sequence of H-CDR2 is shown in SEQ ID NO: 19 or a variant with at most 4 amino acid substitution mutations in SEQ ID NO: 19; the amino acid sequence of H-CDR3 is shown in SEQ ID NO: 20 or a variant with at most 7 amino acid substitution mutations in SEQ ID NO: 20, and (b) light chain complementary determining regions L-CDR1, L-CDR2, L-CDR3, wherein the amino acid sequence of L-CDR1 is shown in SEQ ID NO: 21 or a variant with at most 2 amino acid substitution mutations in SEQ ID NO: 21, the amino acid sequence of L-CDR2 is shown in SEQ ID NO: 22; the amino acid sequence of H-CDR3 is shown in SEQ ID NO: 23 or a variant with at most 3 amino acid substitution mutations in SEQ ID NO: 23. As a preferred embodiment, the antibody binding to human IL-33 or the antigen-binding fragment thereof comprises:

(a) heavy chain complementary determining regions H-CDR1, H-CDR2, H-CDR3, wherein the amino acid sequences of H-CDR1, H-CDR2, H-CDR3 are as shown in SEQ ID NO: 15, 16 and 17 respectively, or as shown in SEQ ID NO: 18, 19 and 20 respectively, or as shown in SEQ ID NO: 18, 24 and 25 respectively, and (b) light chain complementary determining regions L-CDR1, L-CDR2, L-CDR3, wherein the amino acid sequences of L-CDR1, L-CDR2, L-CDR3 are shown in SEQ ID NO: 21, 22 and 23 respectively, or as shown in SEQ ID NO: 26, 22 and 27 respectively, or as shown in SEQ ID NO: 26, 22 and 28 respectively.

In another preferred embodiment, the antibody binding to human IL-33 or the antigen-binding fragment thereof comprises:

(a1) heavy chain complementary determining regions H-CDR1, H-CDR2, H-CDR3, wherein the amino acid sequences of H-CDR1, H-CDR2, H-CDR3 are as shown in SEQ ID NO:15, 16 and 17 respectively, and (b1) light chain complementary determining regions L-CDR1, L-CDR2, L-CDR3, wherein the amino acid sequences of L-CDR1, L-CDR2, L-CDR3 are as shown in SEQ ID NO: 21, 22 and 23 respectively; or (a2) heavy chain complementary determining regions H-CDR1, H-CDR2, H-CDR3, wherein the amino acid sequences of H-CDR1, H-CDR2, H-CDR3 are as shown in SEQ ID NO:18, 19 and 20 respectively, and (b2) light chain complementary determining regions L-CDR1, L-CDR2, L-CDR3, wherein the amino acid sequences of L-CDR1, L-CDR2, L-CDR3 are as shown in SEQ ID NO: 21, 22 and 23 respectively; or (a3) heavy chain complementary determining regions H-CDR1, H-CDR2, H-CDR3, wherein the amino acid sequences of H-CDR1, H-CDR2, H-CDR3 are as shown in SEQ ID NO:18, 24 and 25 respectively, and (b3) light chain complementary determining regions L-CDR1, L-CDR2, L-CDR3, wherein the amino acid sequences of L-CDR1, L-CDR2, L-CDR3 are as shown in SEQ ID NO: 26, 22 and 27 respectively; or (a4) heavy chain complementary determining regions H-CDR1, H-CDR2, H-CDR3, wherein the amino acid sequences of H-CDR1, H-CDR2, H-CDR3 are as shown in SEQ ID NO:18, 19 and 20 respectively, and (b4) light chain complementary determining regions L-CDR1, L-CDR2, L-CDR3, wherein the amino acid sequences of L-CDR1, L-CDR2, L-CDR3 are as shown in SEQ ID NO: 26, 22 and 28 respectively.

In another preferred embodiment, the antibody binding to human IL-33 or the antigen-binding fragment thereof comprises:

(a2) heavy chain complementary determining regions H-CDR1, H-CDR2, H-CDR3, wherein the amino acid sequences of H-CDR1, H-CDR2, H-CDR3 are as shown in SEQ ID NO:18, 19 and 20 respectively, and (b2) light chain complementary determining regions L-CDR1, L-CDR2, L-CDR3, wherein the amino acid sequences of L-CDR1, L-CDR2, L-CDR3 are as shown in SEQ ID NO: 21, 22 and 23 respectively; or (a3) heavy chain complementary determining regions H-CDR1, H-CDR2, H-CDR3, wherein the amino acid sequences of H-CDR1, H-CDR2, H-CDR3 are as shown in SEQ ID NO:18, 24 and 25 respectively, and (b3) light chain complementary determining regions L-CDR1, L-CDR2, L-CDR3, wherein the amino acid sequences of L-CDR1, L-CDR2, L-CDR3 are as shown in SEQ ID NO: 26, 22 and 27 respectively.

In another preferred embodiment, the amino acid sequence of any one of the above-mentioned CDRs includes a derivative CDR sequence with 1, 2, 3, 4, 5, 6 or 7 amino acids added, deleted, modified and/or substituted, and the derivative antibody comprising the VH and VL containing the derivative CDR sequence can retain the affinity of binding to IL-33.

The "Antibody (Ab)" of the present invention is a heterotetrameric glycoprotein of about 150,000 daltons, which consists of two identical light chains (L) and two identical heavy chains (H). Each light chain is connected to the heavy chain through a covalent disulfide bond, and the numbers of disulfide bonds between heavy chains of different immunoglobulin isotypes are different. Each heavy and light chain also has regularly spaced intrachain disulfide bonds. Each heavy chain has a variable region (VH) at one end, followed by constant regions. Each light chain has a variable region (VL) at one end and a constant region at the other end; the constant region of the light chain is opposite to the first constant region of the heavy chain, and the variable region of the light chain is opposite to the variable region of the heavy chain. Antibody of the present invention includes monoclonal antibody, polyclonal antibody, multi-specific antibody formed by at least two antibodies, such as bispecific antibody, etc.

In the present invention, "monoclonal antibody" refers to an antibody obtained from a population that is essentially homogeneous, i.e., the individual antibodies contained in the population are identical except for a few possible naturally occurring mutations. Monoclonal antibody targets a single antigen site with high specificity. Furthermore, unlike conventional polyclonal antibodies preparation, which are usually target antibodies against different determinants, each monoclonal antibody targets a single determinant on an antigen. In addition to their specificity, the benefit of monoclonal antibodies is that they are synthesized by hybridoma culture and are not contaminated with other immunoglobulins. The modifier "monoclonal" indicates the properties of the antibody and is obtained from a homogeneous antibody population, which should not be interpreted as requiring any special method to produce the antibody.

In the present invention, "antigen-binding fragment" refers to a fragment of an antibody that can specifically bind to human IL-33. Examples of antigen-binding fragments of the invention include Fab fragment, $F(ab')_2$ fragment, Fv fragment, etc. Fab fragment is a fragment produced by an antibody digested with papain. $F(ab')_2$ fragment is a fragment produced by an antibody digested with pepsin. Fv fragment is composed of a dimer that is closely non-covalently associated with the heavy and light chain variable regions of the antibody.

In another preferred embodiment, the antibody is a murine antibody, chimeric antibody or humanized antibody.

In the present invention, "murine antibody" refers to the antibody derived from rats or mice, preferably mice. The murine antibody of the present invention is obtained by immunizing mice with human IL-33 as an antigen and screening hybridoma cells.

"Chimeric antibody" of the present invention refers to an antibody comprising heavy and light chain variable region sequences derived from one species and constant region sequences derived from another species, such as an antibody having murine heavy and light chain variable regions connected to the human constant regions. Preferably, the chimeric antibody of the present invention is obtained by recombination of the heavy chain variable region of murine antibody 864F3, 874F7, 871G1 with the heavy chain constant region of human IgG1, IgG2, IgG3 or IgG4 containing mutations, and recombination of the light chain variable region with the human kappa chain constant region.

"Humanized antibody" of the present invention refers to an antibody in which its CDRs are derived from non-human species (preferably mouse) antibody, and the residual portions of the antibody molecule (including frame regions and constant regions) are derived from human antibody. In addition, the residues of frame regions can be altered to maintain binding affinity. Preferably, the humanized antibody of the present invention is obtained by recombination of CDR regions of murine antibody 864F3, 874F7, 871G1 and non-CDR regions of human antibody; then the heavy chain variable region is recombined with the heavy chain constant region of human IgG1, IgG2, IgG3 or IgG4 containing mutations; the light chain variable region is recombined with the human kappa chain constant region and mutating some residues that have important influence.

As a preferred embodiment, the antigen-binding fragment of the present invention includes a Fab fragment, a $F(ab')_2$ fragment, a Fv fragment.

As a preferred embodiment, the amino acid sequences of the heavy chain variable region and the light chain variable region of the antibody binding to human IL-33 or antigen-binding fragment thereof are as shown in SEQ ID NO: 2 and SEQ ID NO: 6 respectively; or as shown in SEQ ID NO: 8 and SEQ ID NO: 10 respectively, or as shown in SEQ ID NO: 4 and SEQ ID NO: 12 respectively As a preferred embodiment, the amino acid sequence of the light chain variable region of the antibody binding to human IL-33 or antigen-binding fragment thereof is shown in SEQ ID NO: 32, and the amino acid sequence of the heavy chain variable region is shown in SEQ ID NO: 29, 30, 31, 33, 34 or 35.

As a preferred embodiment, the amino acid sequence of the light chain variable region of the antibody binding to human IL-33 or antigen-binding fragment thereof is shown in SEQ ID NO: 40, and the amino acid sequence of the heavy chain variable region is shown in SEQ ID NO: 37, 38 or 39.

As a preferred embodiment, the heavy chain constant region of the antibody is selected from the heavy chain constant region of human IgG1, IgG2, IgG3 or IgG4.

As a preferred embodiment, the amino acid sequence of the light chain variable region of the antibody binding to human IL-33 or antigen-binding fragment thereof is shown in SEQ ID NO: 36, and the amino acid sequence of the heavy chain variable region is shown in SEQ ID NO: 33, 34 or 35.

In another preferred embodiment, the amino acid sequence of the light chain variable region of the antibody binding to human IL-33 or antigen-binding fragment thereof is shown in SEQ ID NO: 32, and the amino acid sequence of the heavy chain variable region is shown in SEQ ID NO: 34; or the amino acid sequence of the light chain variable region of the antibody binding to human IL-33 or antigen-binding fragment thereof is shown in SEQ ID NO: 40, and the amino acid sequence of the heavy chain variable region is shown in SEQ ID NO: 38. In another preferred embodiment, the amino acid sequence of the light chain variable region has a sequence homology or sequence identity of at least 80%, 85%, 90%, 91%, 92%, 93%, 94%, 95%, 96%, 97%, 98% or 99% with the amino acid sequence shown in SEQ ID NO: 32, 40 or 36 in the sequence listing.

In another preferred embodiment, the amino acid sequence of the heavy chain variable region has a sequence homology or sequence identity of at least 80%, 85%, 90%, 91%, 92%, 93%, 94%, 95%, 96%, 97%, 98% or 99% with the amino acid sequence shown in SEQ ID NO: 29, 30, 31, 33, 34, 35, 37, 38 or 39 in the sequence listing.

As a preferred embodiment, the amino acid sequences of the heavy chain constant region and the light chain constant region of the antibody binding to human IL-33 or antigen-binding fragment thereof are shown in SEQ ID No: 13 and SEQ ID No: 14, respectively.

In another preferred embodiment, the binding epitope of the antibody binding to human IL-33 or antigen-binding fragment thereof to the IL-33 protein comprises the sites corresponding to SEQ ID NO. 55 selected from the group consisting of:

lysine at position 45 (K45), valine at position 49 (V49), aspartic acid at position 65 (D65), leucine at position 50 (L50), serine at position 60 (S60), serine at position 52 (S52), lysine at position 48 (K48), leucine at position 51 (L51), tyrosine at position 53 (Y53), glutamic acid at position 55 (E55).

Preferably, it comprises the sites selected from the group consisting of: lysine (K45) at position 45, valine (V49) at position 49, aspartic acid (D65) at position 65, leucine (L50) at position 50.

In another preferred embodiment, the site corresponds to the amino acid sequence of wild-type human IL-33 protein, and the amino acid sequence is from Ser at position 112 to Thr at position 270 of NCBI: NP_254274.1.

On the other hand of the present invention, it provides a nucleotide molecule encoding the antibody binding to human IL-33 or antigen-binding fragment thereof.

As a preferred embodiment, the nucleotide sequences of the nucleotide molecules encoding the heavy chain variable region and light chain variable region are shown in SEQ ID NO: 1 and SEQ ID NO: 5 respectively, or shown in SEQ ID NO: 3 and SEQ ID NO: 5 respectively, or shown in SEQ ID NO: 7 and SEQ ID NO: 9 respectively, or shown in SEQ ID NO: 3 and SEQ ID NO: 11 respectively.

As a preferred embodiment, the nucleotide sequence of the nucleotide molecule encoding the heavy chain variable region of the nucleotide molecule is shown in SEQ ID NO: 41, 42, 43, 45, 46 or 47, respectively, and the nucleotide sequence encoding the light chain variable region is shown in SEQ ID NO: 44.

As a preferred embodiment, the nucleotide sequence of the nucleotide molecule encoding the heavy chain variable region is shown in SEQ ID NO: 49, 50 or 51, respectively, and the nucleotide sequence encoding the light chain variable region is shown in SEQ ID NO: 52.

As a preferred embodiment, the nucleotide sequence of the nucleotide molecule encoding the heavy chain variable region is shown in SEQ ID NO: 45, 46 or 47, respectively, and the nucleotide sequence encoding the light chain variable region is shown in SEQ ID NO: 48.

In the present invention, the preparation method of the nucleic acid is a conventional preparation method in the art. Preferably, it comprises the following steps: obtaining the nucleic acid molecule encoding the above-mentioned monoclonal antibody by gene cloning technology, such as PCR method etc., or obtaining the nucleic acid molecule encoding the above-mentioned monoclonal antibody by the method of artificial full-length sequence synthesis.

Those skilled in the art know that the nucleotide sequence encoding the amino acid sequence of the antibody binding to human IL-33 or antigen-binding fragment thereof can be replaced, deleted, changed, inserted or added appropriately to provide a polynucleotide homolog. The polynucleotide homolog of the present invention can be prepared by replacing, deleting or adding one or more bases of the gene encoding the sequence of the antibody binding to human IL-33 or antigen-binding fragment thereof within the scope of maintaining the activity of the antibody.

On the other hand of the present invention, it provides an expression vector comprising the nucleotide molecule described above.

The expression vector mentioned herein is a conventional expression vector in the field, and refers to an expression vector comprising appropriate regulatory sequences, such as promoter sequence, terminator sequence, polyadenylate acylation sequence, enhancer sequence, marker gene and/or sequence, and other appropriate sequences. The expression vector may be a virus or plasmid, such as an appropriate bacteriophage or phagemid, see e.g., Sambrook et al., Molecular Cloning: A Laboratory Manual, Second Edition, Cold Spring Harbor Laboratory Press, 1989 for more technical details. Many of the known techniques and protocols used for nucleic acid manipulation can be found in Current Protocols in Molecular Biology, Second Edition, edited by Ausubel et al. The expression vector of the present invention is preferably pDR1, pcDNA3.1 (+), pcDNA3.1/ZEO (+), pDHFR, pcDNA4, pDHFF, pGM-CSF or pCHO 1.0.

The present invention further provides a host cell containing the expression vector described above.

The host cell of the present invention is one of a variety of conventional host cells in the art, as long as the recombinant expression vector can replicate itself stably and the nucleic acid carried can be effectively expressed. Wherein the host cells comprise prokaryotic expression cells and eukaryotic expression cells, and the host cells preferably comprise: COS, CHO (Chinese Hamster Ovary), NS0, sf9, sf21, DH5α, BL21 (DE3) or TG1, preferably *E. coli* TG1, BL21 (DE3) cells (expressing single-chain antibodies or Fab antibodies) or CHO-K1 cells (expressing full-length IgG antibodies). The above-mentioned expression vector is transformed into a host cell to obtain the preferred recombinant expression transformant of the present invention, wherein the transformation method is a conventional transformation method in the art, preferably a chemical transformation method, a heat shock method or an electrotransformation method.

On the other hand of the present invention, it provides a method for preparing the antibody binding to human IL-33 or antigen-binding fragment thereof described above, which comprises the following steps:

a) culturing the host cell described above under conditions suitable for expression to express the antibody binding to human IL-33 or antigen-binding fragment thereof;
b) isolating and purifying the antibody binding to human IL-33 or antigen-binding fragment thereof in step a).

The culture method of the host cell of the present invention, the isolation and purification method of the antibody is a conventional method in the art, please refer to the corresponding cell culture technology manual and antibody isolation and purification technology manual for specific operation methods. The preparation method of the antibody binding to human IL-33 or an antigen-binding fragment thereof disclosed in the present invention comprises: under expression conditions, the host cells described above are cultured, thereby expressing the antibody binding to human IL-33 or antigen-binding fragment thereof; isolating and purifying the antibody binding to human IL-33 or antigen-binding fragment thereof. With the above method, the recombinant protein can be purified into a substantially homogeneous substance, such as a single band on SDS-PAGE electrophoresis.

The antibody binding to human IL-33 or antigen-binding fragment thereof disclosed in the present invention may be separated and purified by affinity chromatography, and according to the characteristics of the affinity column utilized, conventional methods such as high salt buffer, changing PH and the like may be used to elute the antibody binding to human IL-33 or antigen-binding fragment thereof bound to the affinity column. The inventor of the present invention has conducted detection experiments on the antibody binding to human IL-33 or antigen-binding fragment thereof, and the experimental results show that the antibody binding to human IL-33 or antigen-binding fragment thereof can bind well to the antigen with a high affinity.

On the other hand of the present invention, it provides a composition comprising the antibody binding to human IL-33 or antigen-binding fragment thereof described above and a pharmaceutically acceptable carrier.

The antibody binding to human IL-33 or antigen-binding fragment thereof provided by the present invention, may be combined with a pharmaceutically acceptable carrier to form a pharmaceutical formulation composition to exert efficacy more stably. These preparations can ensure the conformational integrity of the antibody binding to human IL-33 or antigen-binding fragment thereof disclosed in the present invention, while also protecting the protein multifunctional groups from degradation (including but not limited to coagulation, deamination or oxidation). Typically, it is generally stable for at 2° C.-8° C. for liquid formulations and at 30° C. for at least six months for lyophilized preparations. The bispecific antibody preparation may be suspension, water needle, lyophilized preparation and other preparations commonly used in the pharmaceutical field.

For the water needle or lyophilized preparation of the antibody binding to human IL-33 or antigen-binding fragment thereof disclosed in the present invention, pharmaceutically acceptable carriers preferably include, but are not limited to: one of surfactant, solution stabilizer, isotonic modulator and buffer, or a combination thereof. Wherein the surfactants preferably include, but are not limited to, non-ionic surfactants such as polyoxyethylene sorbitan fatty acid ester (Tween 20 or 80); poloxamer (e.g., poloxamer 188); Triton; sodium dodecyl sulfate (SDS); sodium lauryl sulfate; tetradecyl, linoleyl, or octadecyl sarsarine; Pluronics; MONAQUAT™ et al., the dosage of which should minimize the granulation tendency of the antibody binding to human IL-33 or antigen-binding fragment thereof. Solution stabilizers preferably include, but are not limited to one of sugars, e.g., reducing sugars and non-reducing sugars; amino acids, such as monosodium glutamate or histidine; alcohols, such as ternary alcohols, advanced sugar alcohols, propylene glycol, polyethylene glycol, etc., or a combination thereof. The addition amount of solution stabilizer should keep the final preparation stable for the time considered stable by the skilled in the art. Isotonic modifiers preferably include, but are not limited to one of sodium chloride, mannitol, or a combination thereof. Buffers preferably include, but are not limited to one of Tris, histidine buffer, phosphate buffer, or a combination thereof.

On the other hand of the present invention, it provides an antibody-drug conjugate, which comprises:

(a) an antibody moiety, which comprises the antibody binding to human IL-33 or antigen-binding fragment thereof as described above; and (b) a coupling moiety coupled to the antibody moiety, which is selected from the group consisting of a detectable label, a drug, a toxin, a cytokine, a radionuclide, an enzyme, and a combination thereof.

On the other hand of the present invention, it provides a use of the above-mentioned binding human IL-33 antibody or antigen-binding fragment thereof or pharmaceutical composition, antibody-drug conjugate in the preparation of a drug for treating asthma, arthritis, specific reactive/allergic dermatitis, chronic sinusitis, chronic obstructive pulmonary disease (COPD), systemic sclerosis, liver fibrosis, psoriasis, ulcerative colitis, Crohn's disease, multiple sclerosis, diabetic kidney disease, inflammatory bowel disease, psoriasis, eosinophilic esophagitis, diabetic macular edema, age-related macular degeneration, xerophthalmus, tumors. The arthritis comprises rheumatoid arthritis, osteoarthritis, ankylosing spondylitis, gouty arthritis, reactive arthritis, infectious arthritis, traumatic arthritis, psoriatic arthritis, enteropathic arthritis.

When the antibody binding to human IL-33 or antigen-binding fragment thereof or composition thereof of the present invention is administered to animals including humans, the dosage varies depending on the age and weight of the patient, the characteristics and severity of the disease, and the route of administration. The results of animal experiments and various situations can be referred, and the total dosage should not exceed a certain range. Specifically, the dose of intravenous injection is 1-1800 mg/day.

On the other hand of the present invention, it provides a method for treating asthma, arthritis, specific reactive/allergic dermatitis, chronic sinusitis, chronic obstructive pulmonary disease (COPD), systemic sclerosis, liver fibrosis, psoriasis, ulcerative colitis, Crohn's disease, multiple sclerosis, diabetic kidney disease, inflammatory bowel disease, psoriasis, eosinophilic esophagitis, diabetic macular edema, age-related macular degeneration, xerophthalmus, tumors, which comprises: administering to the subject in need with the above-mentioned antibody binding to human IL-33 or antigen-binding fragment thereof, composition, antibody-drug conjugate, or a combination thereof.

On the other hand of the present invention, it provides a mutant of IL-33 protein, corresponding to the amino acid sequence of wild-type human IL-33 protein, the mutant comprises mutation at one or more sites selected from the group consisting of:

(Z1) lysine at position 45 (K45);
(Z2) valine at position 49 (V49);
(Z3) aspartic acid at position 65 (D65);
(Z4) leucine at position 50 (L50);
(Z5) serine at position 60 (S60);
(Z6) serine at position 52 (S52);
(Z7) lysine at position 48 (K48);
(Z8) leucine at position 51 (L51);
(Z9) tyrosine at position 53 (Y53);
(Z10) glutamic acid at position 55 (E55).

In another preferred embodiment, the amino acid sequence of wild-type human IL-33 protein is as shown in SEQ ID NO 55.

In another preferred embodiment, the mutant comprises mutation at one or more sites selected from the group consisting of:

(Z1) lysine at position 45 (K45);
(Z2) valine at position 49 (V49);
(Z3) aspartic acid at position 65 (D65);
(Z4) leucine at position 50 (L50); and/or the mutant comprises mutation at one or more sites selected from the group consisting of:

(Z5) serine at position 60 (S60);
(Z6) serine at position 52 (S52); and/or the mutant comprises mutation at one or more sites selected from the group consisting of:

(Z7) lysine at position 48 (K48);
(Z8) leucine at position 51 (L51);
(Z9) tyrosine at position 53 (Y53);
(Z10) glutamic acid at position 55 (E55).

In another preferred embodiment, compared with the affinity between the wild-type IL-33 protein and the antibody binding to human IL-33, the affinity between IL-33 protein mutant and the antibody binding to human IL-33 is reduced by 1 fold, preferably by 5 fold, more preferably by 10 fold, more preferably by 25 fold, and most preferably by 50 fold.

In another preferred embodiment, the mutant comprises mutation at one or more sites selected from the group consisting of:

(Z11) lysine at position 41 (K41);
(Z12) lysine at position 42 (K42);
(Z13) aspartic acid at position 43 (D43);
(Z14) glutamic acid at position 44 (E44);
(Z15) lysine at position 46 (K46);
(Z16) aspartic acid at position 47 (D47);
(Z17) tyrosine at position 54 (Y54);
(Z18) serine at position 56 (S56);
(Z19) glutamine at position 57 (Q57);
(Z20) histidine at position 58 (H58);
(Z21) proline at position 59 (P59);
(Z22) asparagine at position 61 (N61);
(Z23) glutamic acid at position 62 (E62);
(Z24) serine at position 63 (S63);
(Z25) valine at position 67 (V67);
(Z26) aspartic acid at position 68 (D68);
(Z27) lysine at position 70 (K70).

In another preferred embodiment, the IL-33 protein mutant comprises mutating one or more amino acids in (Z1)-(Z27) to alanine (A) or glycine (G).

In another preferred embodiment, the mutation of IL-33 protein mutant is selected from the group consisting of:

K45A, V49A, D65A, L50A, S60A, S52A, K48A, L51A, Y53A, E55A, K41A, K42A, D43A, E44A, K46A, D47A, Y54A, S56A, Q57A, H58A, P59A, N61A, E62A, S63A, V67A, D68A, K70A, or a combination thereof;

Preferably, one or more from the following group: K45A, V49A, D65A, L50A, S60A, S52A, K48A, L51A, Y53A, E55A; more preferably, one or more from the following group: K45A, V49A, D65A, L50A, S60A, S52A; most preferably, one or more from the following group: K45A, V49A, D65A, L50A.

In another preferred embodiment, the IL-33 protein mutant is selected from the group consisting of:

a derivative polypeptide with the function of binding to IL-33 antibody formed by substituting, deleting or adding one or several amino acid residues, preferably 1-20, more preferably 1-15, more preferably 1-10, more preferably 1-8, more preferably 1-3, most preferably 1 amino acid residue in amino acid sequence shown in SEQ ID NO.: 55.

In another preferred embodiment, the amino acid sequence of the IL-33 protein mutant has a sequence identity of at least 70%, preferably at least 75%, 80%, 85%, 90%, and more preferably at least 95%, 96%, 97%, 98%, 99% or more with SEQ ID NO.55.

On the other hand of the present invention, it provides a method for evaluating anti-human IL-33 antibody binding to epitopes, which comprises:

(S1) providing an anti-human IL-33 antibody;

(S2) compared to the affinity A2 of binding to wild-type IL-33 protein, detecting the affinity A1 of the anti-human IL-33 antibody with the IL-33 mutant, wherein the IL-33 mutant comprises one or more site mutations of K45A, V49A, L50A, D65A, S60A or S52A, if the affinity decreases by a ratio of $A1/A2 \geq 2.5$ times, preferably $\geq 10$ times, indicating that the linear and/or spatial epitope to which the anti-human IL-33 antibody that binding of wild-type IL-33 protein comprises one or more sites of the K45, V49, L50, D65, 560A or S52A; wherein the anti-human IL-33 antibody comprises:

heavy chain complementary determining regions H-CDR1, H-CDR2, H-CDR3, wherein amino acid sequences of H-CDR1, H-CDR2, H-CDR3 are as shown in SEQ ID NO:18, 24 and 25, respectively, and light chain complementary determining regions L-CDR1, L-CDR2, L-CDR3, wherein amino acid sequences of L-CDR1, L-CDR2, L-CDR3 are as shown in SEQ ID NO:26, 22 and 27, respectively.

On the basis of conforming to common knowledge in the art, the above-mentioned preferred conditions can be combined arbitrarily to obtain preferred embodiments of the present invention.

The reagents and raw materials used in the present invention are all commercially available.

The positive progressive effect of the present invention is that there is an urgent need to develop new, specific and efficient therapeutic drugs for IL-33 strong expression diseases, so as to improve the quality of life of people with such diseases and provide more and more effective treatment options for patients. The antibodies of the present invention have a good affinity for human IL-33 and can block the binding of IL-33 and its receptor ST2, which can be used to treat a variety of diseases, and have good clinical application prospects.

DETAILED DESCRIPTION

Figure 1A:
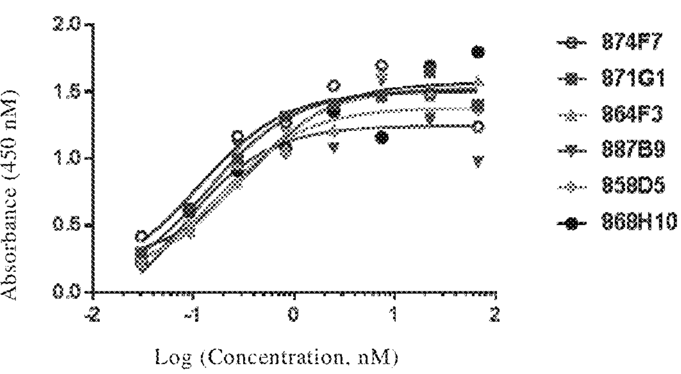
FIG. 1A-1B: Binding activity of murine antibodies to human IL-33.

Through extensive and intensive research, the present inventors obtained a series of anti-IL-33 humanized antibodies with high affinity after a large—scale screening. Specifically, the humanized antibody of the present invention can block the binding of IL-33 and its receptor ST2, inhibit the secretion of IFN-γ by PBMC and NK cells induced by IL-33, and inhibit the secretion of IL-5 and IL-13 by basophilic leukemia cells KU812 induced by IL-33. The humanized antibody of the present invention has obvious neutralizing activity in vivo. In animal experiments on mice, single treatment with the humanized antibody of the present invention can effectively reduce the increase of eosinophils induced by human IL-33 stimulation in peripheral blood of mice. The antibody of the present invention is expected to treat a variety of IL-33 related diseases. On this basis, the present invention has been completed.

The Terms

As used herein, the term "antibody (Ab)" or "immunoglobulin (IgG)" is a heterotetrameric glycoprotein with the same structural characteristics, which consists of two identical light chains (L) and two identical heavy chains (H). Each light chain is connected to the heavy chain through a covalent disulfide bond, and the numbers of disulfide bonds between heavy chains of different immunoglobulin isotypes are different. Each heavy and light chain also has regularly spaced intrachain disulfide bonds. Each heavy chain has a variable region (VH) at one end, followed by a constant region, which consists of three domains CH1, CH2, and CH3. Each light chain has a variable region (VL) at one end and a constant region at the other end; the constant region of the light chain is paired to the CH1 domain of the constant region of the heavy chain, and the variable region of the light chain is paired to the variable region of the heavy chain. The constant regions are not directly involved in the binding of antibodies to antigens, but they exhibit different effector functions, such as participating in antibody-dependent cell-mediated cytotoxicity (ADCC). The heavy chain constant region includes IgG1, IgG2, IgG3, IgG4 subtypes; the light chain constant region includes κ (Kappa) or λ (Lambda). The heavy and light chains of the antibody are covalently linked together by disulfide bonds between the CH1 domain of the heavy chain and the CL domain of the light chain, and the two heavy chains of the antibody are covalently linked together by the polypeptide disulfide bonds formed between the hinge regions.

In the present invention, the terms "Fab" and "Fc" refer to papain may cleave the antibody into two identical Fab segments and one Fc segment. The Fab segment consists of VH and CH1 domains of the heavy chain of the antibody and VL and CL domains of the light chain of the antibody. The Fab segment is fragment crystallizable (Fc), which consists of CH2 and CH3 domains of the antibody. The Fc segment has no antigen-binding activity and is the site for interaction between antibodies and effector molecules or cells.

In the present invention, the term "scFv" is a single-chain antibody (scFv), which is usually formed by linking heavy chain variable region and light chain variable region of the antibody by a short linking peptide (linker) with 15-25 amino acids.

In the present invention, the term "variable" means that certain parts of the variable region of an antibody differ in sequence, which forms the binding activity and specificity of various specific antibodies for their specific antigens. However, the variability is not evenly distributed throughout the variable region of the antibody. It is concentrated in three segments called complementary determining regions (CDRs) or hypervariable regions in the light chain and heavy chain variable regions. The more conserved part of the variable region is called framework region (FR). The variable regions of the natural heavy and light chains each contain four FR regions, which are roughly in a β-folded configuration, connected by the three CDRs that form the connecting loop, and in some cases may form a partly β folded structure. The CDRs in each chain get close through the FR regions and together with the CDRs of the other chain form the antigen-binding site of the antibody (see Kabat et al., NIH Publ. No. 91-3242, Volume I, pages 647-669 (1991)).

As used herein, the term "framework region (FR)" refers to amino acid sequences inserted between CDRs, i.e., those relatively conserved portions of the light and heavy chain variable regions of immunoglobulins between different immunoglobulins in a single species. The light and heavy chains of immunoglobulins each have four FRs, which are called FR1-L, FR2-L, FR3-L, FR4-L and FR1-H, FR2-H, FR3-H, FR4-H, respectively. Accordingly, the light chain variable domain can thus be called (FR1-L)-(CDR1-L)-(FR2-L)-(CDR2-L)-(FRR3-L)-(CDR3-L)-(FR4-L) and the heavy chain variable domain can thus be expressed as (FR1-H)-(CDR1-H)-(FR2-H)-(CDR2-H)-(FR3-H)-(FRR3-H)-(FR4-H). Preferably, the FR of the present invention is a human antibody FR or a derivative thereof, the derivative of the human antibody FR is substantially the same as the naturally occurring human antibody FR, i.e., sequence identity reaches 85%, 90%, 95%, 96%, 97%, 98% or 99%.

Knowing the amino acid sequence of the CDR, those skilled in the art can easily determine the frame region FR1-L, FR2-L, FR3-L, FR4-L and/or FR1-H, FR2-H, FR3-H, FR4-H.

As used herein, the term "human frame region" is substantially the same (about 85% or more, specifically 90%, 95%, 97%, 99% or 100%) frame region as the naturally occurring human antibody frame region.

As used herein, the term "linker" refers to one or more amino acid residues inserted into the immunoglobulin domain to provide sufficient mobility for the domain of light and heavy chains to fold into exchange dual variable region immunoglobulins. In the present invention, a preferred linker refers to the Linker1 and Linker2, wherein Linker 1 connects VH and VL of a single-chain antibody (scFv), and Linker2 is used to connect scFv with a heavy chain of another antibody.

Examples of suitable linkers include single glycine (Gly), or serine (Ser) residues, and the identification and sequence of amino acid residues in the linker may vary with the type of secondary structural element to be implemented in the linker.

In the present invention, the antibody of the present invention also includes conservative variants thereof, which means that compared with the amino acid sequence of the antibody of the present invention, there are at most 10, preferably at most 8, more preferably at most 5, most preferably at most 3 amino acids replaced by amino acids with the same or similar properties to form a polypeptide. These conservatively variant polypeptides are preferably produced by amino acid substitution according to Table A.

TABLE A

| Initial residue | Representative substitution | Preferred substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

In the present invention, the terms "anti", "binding", "specific binding" refers to a non-random binding reaction between two molecules, such as a reaction between an antibody and an antigen targeted thereto. Typically, antibody binds to its antigen with an equilibrium dissociation constant (KD) of less than about $10^{-7}$M, e.g., less than about $10^{-8}$M, $10^{-9}$M, $10^{-10}$M, $10^{-11}$M, or less. In the present invention, the term "KD" refers to the equilibrium dissociation constant of a particular antibody-antigen interaction, which is used to describe the binding affinity between the antibody and the antigen. The smaller the equilibrium dissociation constant is, the closer the antibody-antigen binding is and the higher the affinity between the antibody and the antigen is. For example, the binding affinity of an antibody to an antigen is determined using Surface Plasmon Resonance (SPR) in a BIACORE apparatus or the relative affinity of an antibody binding to an antigen is determined using ELISA.

In the present invention, the term "epitope" refers to a peptide determinant specifically binding to an antibody. The epitope of the present invention is the region of the antigen bound by the antibody.

The present invention also provides the polynucleotide molecule encoding the above-mentioned antibody or fragment thereof or fusion protein thereof. The polynucleotide of the present invention may be in a form of DNA or RNA. DNA forms include cDNA, genomic DNA, or synthetic DNA. DNA may be single stranded or double stranded. DNA may be the coding strand or the non-coding strand.

Once a relevant sequence is obtained, recombination methods can be used to obtain the relevant sequence in large quantities. This is usually carried out by cloning the sequence into a vector, transforming a cell with the vector, and then separating the relevant sequence from the proliferated host cell by conventional methods.

The present invention further relates to a vector comprising said suitable DNA sequence and suitable promoters or control sequences. These vectors can be used to transform suitable host cells to enable them to express protein.

Pharmaceutical Composition and Application

The present invention further provides a composition. Preferably, the composition is a pharmaceutical composition comprising the above-mentioned antibody, or an active fragment thereof, or a fusion protein thereof, and a pharmaceutically acceptable carrier. In general, these substances may be formulated in a non-toxic, inert and pharmaceutically acceptable aqueous carrier medium, wherein the pH is generally about 5-8, preferably, pH is about 6-8, though the pH value may be varied depending on the nature of the substances to be formulated and the condition to be treated. The formulated pharmaceutical composition may be administered by conventional routes, including (but not limited to): intravenous injection, intravenous drip, subcutaneous injection, local injection, intramuscular injection, intratumoral injection, intraperitoneal injection (e.g., intraperitoneal), intracranial injection, or intraluminal injection. In the present invention, the term "pharmaceutical composition" refers to the bispecific antibody of the present invention may be combined with a pharmaceutically acceptable carrier to form a pharmaceutical formulation composition to exert efficacy more stably. These preparations can ensure the conformational integrity of the amino acid core sequence of the bispecific antibody disclosed in the present invention, while also protecting the protein multifunctional groups from degradation (including but not limited to coagulation, deamination or oxidation). The pharmaceutical composition according to the present invention comprises a safe and effective amount (e.g. 0.001-99 wt %, preferably 0.01-90 wt %, preferably 0.1-80 wt %) of the above-mentioned bispecific antibody according to the present invention (or a conjugate thereof) and a pharmaceutically acceptable carrier or excipient. Such carriers include (but are not limited to): saline, buffer, glucose, water, glycerol, ethanol, and a combination thereof. Pharmaceutical preparations should correspond to the administration modes. The pharmaceutical composition according to the present invention can be prepared in the form of an injection, for example, by a conventional method using physiological saline or an aqueous solution containing glucose and other adjuvants. A pharmaceutical composition, for example, an injection and a solution, should be prepared under a sterile condition. The dosage of active ingredient is therapeutically effective amount, for example from about 10 microgram per kilogram of body weight to about 50 milligrams per kilogram of body weight per day. In addition, the bispecific antibody of the present invention may also be used in combination with an additional therapeutic agent.

When the pharmaceutical composition is used, a safe and effective amount of the bispecific antibody or immunoconjugate thereof is administered to a mammal, wherein the safe and effective amount is generally at least about 10 μg per kilogram of body weight, and in most cases, no more than about 50 mg per kilogram of body weight, preferably, the amount is from about 10 μg per kilogram of body weight to about 10 mg per kilogram of body weight. Of course, a specific amount should also depend on the factors such as administration route and physical conditions of a patient, which fall into the skills of skilled physicians.

Antibody-Drug Conjugate (ADC)

The present invention also provides an antibody-drug conjugate (ADC) based on the antibody of the present invention.

Typically, the antibody-drug conjugate comprises the antibody and an effector molecule, wherein the antibody is conjugated, preferably chemically conjugated to the effector molecule. Preferably, the effector molecule is a therapeutically active drug. In addition, the effector molecule may be one or more of a toxic protein, a chemotherapeutic drug, a small-molecule drug or a radionuclide.

The antibody of present invention and the effector molecule may be coupled by a coupling agent. Examples of the coupling agent may be any one or more of a non-selective coupling agent, a coupling agent utilizing a carboxyl group, a peptide chain, and a coupling agent utilizing a disulfide bond. The non-selective coupling agent refers to a compound that forms a covalent bond between the effector molecule and the antibody, such as glutaraldehyde, etc. The coupling agent utilizing a carboxyl group may be any one or more of cis-aconitic anhydride coupling agents (such as cis-aconitic anhydride) and acyl hydrazone coupling agents (the coupling site is acyl hydrazone).

Certain residues on an antibody (such as Cys or Lys, etc.) are used to link a variety of functional groups, including imaging agents (such as chromophores and fluorophores), diagnostic agents (such as MRI contrast agents and radioisotopes), stabilizers (such as poly(ethylene glycol)) and therapeutic agents. An antibody can be conjugated to a functional agent to form a conjugate of the antibody-functional agent. A functional agent (e.g., a drug, a detection reagent, a stabilizer) is conjugated (covalently linked) to an antibody. A functional agent can be linked to an antibody either directly or indirectly via a linker.

Antibodies can be conjugated to drugs to form antibody-drug conjugates (ADCs). Typically, an ADC comprises a linker between a drug and an antibody. The linker can be a degradable or non-degradable linker. Typically, the degradable linker is easily degraded in an intracellular environment, for example, the linker is degraded at the target site, thereby releasing the drug from the antibody. Suitable degradable linkers include, for example, enzyme-degradable linkers, including peptidyl-containing linkers that can be degraded by protease (e.g., lysosomal protease or endosomal protease) in a cell, or sugar linkers, for example, glucuronide-containing linkers that can be degraded by glucuronidase. Peptidyl linkers may include, for example, dipeptides, such as valine-citrulline, phenylalanine-lysine or valine-alanine. Other suitable degradable linkers include, for example, pH sensitive linkers (e.g., linkers that are hydrolyzed at a pH of below 5.5, such as hydrazone linkers) and linkers that are degraded under reducing conditions (e.g., disulfide-bond linkers). A non-degradable linker typically releases a drug under conditions that the antibody is hydrolyzed by protease.

Prior to linkage to an antibody, a linker has a reactive group capable of reacting with certain amino acid residues, and the linkage is achieved by the reactive group. A thiol-specific reactive group is preferred, and includes, for example, a maleimide compound, a halogenated (e.g., iodo-, bromo- or chloro-substituted) amide; a halogenated (e.g., iodo-, bromo- or chloro-substituted) ester; a halogenated (e.g., iodo-, bromo- or chloro-substituted) methyl ketone, a benzyl halide (e.g., iodide, bromide or chloride); vinyl sulfone, pyridyl disulfide; a mercury derivative such as 3,6-di-(mercurymethyl)dioxane, wherein the counter ion is CH3COO—, Cl— or NO3-; and polymethylene dimethyl sulfide thiosulfonate. The linker may include, for example, a maleimide linked to an antibody via thiosuccimide.

A drug may be any cytotoxic, cytostatic or immunosuppressive drug. In an embodiment, an antibody is linked to a drug via a linker, and the drug has a functional group that can form a bond with the linker. For example, a drug may have an amino group, a carboxyl group, a thiol group, a hydroxyl group, or a ketone group that can form a bond with a linker. When a drug is directly linked to a linker, the drug has a reactive group before being linked to an antibody.

Useful drugs include, for example, anti-tubulin drugs, DNA minor groove binding agents, DNA replication inhibitors, alkylating agents, antibiotics, folic acid antagonists, antimetabolites, chemotherapy sensitizers, topoisomerase inhibitors, vinca alkaloids, etc. In the present invention, a drug-linker can be used to form an ADC in a simple step. In other embodiments, a bifunctional linker compound can be used to form an ADC in a two-step or multi-step process. For example, a cysteine residue is reacted with the reactive moiety of a linker in a first step, and then the functional group on the linker is reacted with a drug in the subsequent step, so as to form an ADC.

In general, the functional group on a linker is selected so that it can specifically react with the suitable reactive group on a drug moiety. As a non-limiting example, an azide-based moiety can be used to specifically react with the reactive alkynyl group on a drug moiety. The drug is covalently bound to the linker by 1,3-dipolar cycloaddition between the azide and alkynyl group. Other useful functional groups include, for example, ketones and aldehydes (suitable for reacting with hydrazides and alkoxyamines), phosphines (suitable for reacting with azides); isocyanates and isothiocyanates (suitable for reacting with amines and alcohols); and activated esters, for example, N-hydroxysuccinimide esters (suitable for reacting with amines and alcohols). These and other linkage strategies, for example, as described in Bioconjugation Technology (2nd Edition (Elsevier)), are well known to those skilled in the art. Those skilled in the art could understand that when a complementary pair of reactive functional groups are selected for a selective reaction between a drug moiety and a linker, each member of the complementary pair can be used for the linker, and can also be used for the drug.

The present invention further provides a method for preparing an ADC, which may further comprise: under conditions sufficient to form an antibody-drug conjugate (ADC), connecting an antibody to a drug-linker compound.

In certain embodiments, the method according to the present invention comprises: under conditions sufficient to form an antibody-linker conjugate, connecting an antibody to a bifunctional linker compound. In these embodiments, the method according to the present invention further comprises: under conditions that the drug moiety is sufficient to be covalently linked to the antibody via a linker, connecting the antibody-linker conjugate to the drug moiety.

In some embodiments, an antibody-drug conjugate (ADC) has a formula as follows:

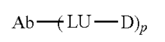

wherein,

Ab is an antibody,

LU is a linker;

D is a drug;

and the subscript p is a value selected from 1 to 8.

The following embodiments are further descriptions of the present invention and should not be understood as limitations of the present invention. Examples do not include a detailed description of traditional methods, such as those methods for constructing vectors and plasmids, methods for inserting genes encoding proteins into such vectors and plasmids, or methods for introducing plasmids into host cells. Such methods are well known to those with ordinary skills in the art and have been described in numerous publications, including Sambrook, J., Fritsch, E. F. and Maniais, T. (1989) Molecular Cloning: A Laboratory Manual, 2nd edition, Cold spring Harbor Laboratory Press.

The experimental materials and sources used in the following examples and the preparation methods of the experimental reagents are described below.

Experimental Materials and Reagents:

Balb/c mouse: purchased from Shanghai Lingchang Biotechnology Co., Ltd.

PBMC: purchased from Ausails Biotechnology (Shanghai) Co., Ltd., catalog number PB004-C.

Human IL-33-his: Ser112-Thr270 (NCBI accession number NP_254274.1) of the IL-33 sequence was cloned to the *E. coli* expression vector for expression, and 6×His tag was added to the C-terminus of IL-33 for purification by $Ni^+$ affinity chromatography column, whose amino acid sequence is shown in SEQ ID NO: 53.

Cynomolgus IL-33-his: purchased from Yiqiao Shenzhou company, catalog number 90912-CNAE.

IL-33-his-biotin protein: purchased from Thermo Fisher, catalog number 20217. IL-33-his protein was biotinized according to the reagent manual for EZ-Link NHS-Biotin Reagent.

Rat-Anti-human IL-6: purchased from BD Pharmingen, catalog number 554543.

Biotin Rat Anti Human IL-6: purchased from BD Pharmingen, catalog number 554546.

Mouse-Anti-human IFNγ: purchased from BD Biosciences, catalog number 551221.

Biotin mouse-anti-human IFNγ: purchased from BD Biosciences, catalog number 554550.

Sheep Goat anti-mouse secondary antibody: purchased from Millipore, catalog number AP181P.

HRP-anti human IgG Fc secondary antibody: purchased from Sigma, catalog number A0170.

HRP-labeled streptavidin secondary antibody: purchased from BD Biosciences, catalog number 554066.

IL-6 kit: Invitrogen, catalog number 88-7066-77.

IL-8 kit: Invitrogen, catalog number BMS204-3TEN

IL-12: purchased from Sino Biological, catalog number CT011-H08H.

ST2-Fc protein: the human ST2 sequence (NCBI accession number NP_003847.2) was fused with the Fc region sequence of human IgG1 and cloned into the eukaryotic expression vector PTT5, which was fused and expressed by transfection of HEK-293F cells, and then the expression supernatant was collected and purified by ProteinA affinity chromatography column. The ST2-Fc amino acid sequence is shown in SEQ ID NO: 54.

TMB: purchased from BD Company, catalog number 555214.

1% Glutmine, 1% Sodium pyruvate, 1% MEM-NEAA (minimum basic medium-non-essential amino acid solution), 1% Penicillin-streptomycin, β-mercaptoethanol and 20% FBS (fetal bovine serum): all purchased from Gibco Company.

SA protein: Streptavidin, purchased from Sigma, catalog number 85878-1MG.

SFM Medium: purchased from life technologies Company, catalog number 12045-076.

RPMI1640 Complete Medium: purchased from Gibco.

Experimental Instruments:

Electrofusion Instrument: purchased from BTX Scientific Company.

Microplate reader: purchased from Molecular Devices, model: SpectraMax 190.

The antibody sequences of the present invention are shown in the following table:

| SEQ ID NO. | Name | Sequence |
|---|---|---|
| 2 | 864F3-ch1 VH | QVQLKESGPGLVAPSQSLSITCTVSGFSLTNYGVHWV RLPPGKGLEWLGVIRAGGSSDYNSALMSRLNIRKDNS KSQVFLEMNSLQTADTAMYYCARDHYFSNSYGGSPYW GQGTLVTVSA |
| 4 | 864F3-ch2, 871G1-ch VH | QVHLKESGPGLVAPSQSLSITCNVSGFSLSKYGVHWI RQTPGRGLDWLGVLRAGGTISYNSALMSRLSISEDIS KSQVFLKMNDLQTDDSAIYFCARDHYYYSSFGGFASW GQGTLVTVSA |
| 6 | 864F3-ch1, 864F3-ch2 VL | DIQMTQSPASQSASLGESVTITCLASQTIATWLAWYQ QKPGKSPQLLIYAATRLADGVPSRFSGSGSGTEFSFK ISSLQAEDFVIYYCQQLYNTPYTFGGGTKLEIK |
| 8 | 874F7-ch VH | QVQLKESGPGLVAPSHSLSITCNVSGFSLSKYGVHWI RQIPGRGLDWLGVLRAGGSTGYNSALMSRLSISKDSS KSQVFLKMNDLRTDDTAVYFCVRDHYYYSSYGGFVYW GQGTLVTVSA |
| 10 | 874F7-ch VL | DIQMTQSPASQSASLGESVTITCLASQTIGAWLAWYR QQPGKSPQLLIYAATRLADGVPSRFSGSGSGTEFSFK INNLQAEDFVSYYCQQLDSSPYTFGGGTRLEM |
| 12 | 871G1-ch VL | DIQMTQSPASQSASLGESVTITCLASQTIGAWLAWYR QQPGKSPQLLIYAATRLADGVPSRFSGSGSGTKFSFK INNLQAEDFVIYYCQQLNSTPYTFGGGTRLEM |
| 13 | Heavy chain constant region | ASTKGPSVFPLAPCSRSTSESTAALGCLVKDYFPEPV TVSWNSGALTSGVHTFPAVLQSSGLYSLSSVVTVPSS SLGTKTYTCNVDHKPSNTKVDKRVESKYGPPCPPCPA PEFLGGPSVFLFPPKPKDTLMISRTPEVTCVVVDVSQ |

-continued

| SEQ ID NO. | Name | Sequence |
|---|---|---|
| | | EDPEVQFNWYVDGVEVHNAKTKPREEQFNSTYRVVSV LTVLHQDWLNGKEYKCKVSNKGLPSSIEKTISKAKGQ PREPQVYTLPPSQEEMTKNQVSLTCLVKGFYPSDIAV EWESNGQPENNYKTTPPVLDSDGSFFLYSRLTVDKSR WQEGNVFSCSVMHEALHNHYTQKSLSLSLGK |
| 14 | Light chain constant region | RTVAAPSVFIFPPSDEQLKSGTASVVCLLNNFYPREA KVQWKVDNALQSGNSQESVTEQDSKDSTYSLSSTLTL SKADYEKHKVYACEVTHQGLSSPVTKSFNRGEC |
| 15 | 864F3 HCDR1 | NYGVH |
| 16 | 864F3 HCDR2 | VIRAGGSSDYNSALMS |
| 17 | 864F3 HCDR3 | DHYFSNSYGGSPY |
| 18 | 864F3, 874F7, 871G1 HCDR1 | KYGVH |
| 19 | 864F3, 871G1 HCDR2 | VLRAGGTISYNSALMS |
| 20 | 864F3, 871G1 HCDR3 | DHYYYSSFGGFAS |
| 21 | 864F3 LCDR1 | LASQTIATWLA |
| 22 | 864F3, 874F7, 871G1 LCDR2 | AATRLAD |
| 23 | 864F3 LCDR3 | QQLYNTPYT |
| 24 | 874F7 HCDR2 | VLRAGGSTGYNSALMS |
| 25 | 874F7 HCDR3 | DHYYYSSYGGFVY |
| 26 | 874F7, 871G1 LCDR1 | LASQTIGAWLA |
| 27 | 874F7 LCDR3 | QQLDSSPYT |
| 28 | 871G1 LCDR3 | QQLNSTPYT |
| 29 | 864F3-HuG VH | QVQLQESGPGLVKPSETLSLTCTVSGFSLTNYGVHWI RQPPGKGLEWIGVIRAGGSSDYNSALMSRVTISVDTS KNQFSLKLSSVTAADTAVYYCARDHYFSNSYGGSPYW GQGTLVTVSS |
| 30 | 864F3-Hu1 VH | QVQLQESGPGLVKPSETLSLTCTVSGFSLTNYGVHWI RLPPGKGLEWIGVIRAGGSSDYNSALMSRVTISKDNS KSQVSLKLSSVTAADTAVYYCARDHYFSNSYGGSPYW GQGTLVTVSS |
| 31 | 864F3-Hu2 VH | QVQLQESGPGLVKPSETLSLTCTVSGFSLTNYGVHWV RLPPGKGLEWLGVIRAGGSSDYNSALMSRLTISKDNS KSQVSLKLSSVTAADTAVYYCARDHYFSNSYGGSPYW G |

-continued

| SEQ ID NO. | Name | Sequence |
|---|---|---|
| 32 | 864F3-HuG, 864F3-Hu1, 864F3-Hu2, 864F3-Hu3, 864F3-Hu4, 864F3-Hu5VL | DIQMTQSPSSLSASVGDRVTITCLASQTIATWLAWYQQKPGKSPKLLIYAATRLADGVPSRFSGSGSGTDFTLTISSLQPEDFATYYCQQLYNTPYTFGQGTKVEIK |
| 33 | 864F3-Hu3, 871G1-HuG VH | QVQLQESGPGLVKPSETLSLTCTVSGFSLSKYGVHWIKRQPPGGLEWIGVLRAGGTISYNSALMSRVTISVDTSKNQFSLKLSSVTAADTAVYYCARDHYYYSSFGGFASWGQGTLVTVSS |
| 34 | 864F3-Hu4, 871G1-Hu1 VH | QVQLQESGPGLVKPSETLSLTCTVSGFSLSKYGVHWIRQPPGKGLEWIGVLRAGGTISYNSALMSRVTISEDISKSQVSLKLSSVTAADTAVYYCARDHYYYSSFGGFASWGQGTLVTVSS |
| 35 | 864F3-Hu5, 871G1-Hu2 VH | QVQLQESGPGLVKPSETLSLTCTVSGFSLSKYGVHWIRQPPGKGLEWLGVLRAGGTISYNSALMSRLTISEDISKSQVSLKLSSVTAADTAVYYCARDHYYYSSFGGFASWGQGTLVTVSS |
| 36 | 871G1-HuG, 871G1-Hu1, 871G1-Hu2 VL | DIQMTQSPSSVSASVGDRVTITCLASQTIGAWLAWYQQKPGKSPKLLIYAATRLADGVPSRFSGSGSGTDFTLTISSLQPEDFATYYCQQLNSTPYTFGQGTKVEIK |
| 37 | 874F7-HuG VH | QVQLQESGPGLVKPSETLSLTCTVSGFSLSKYGVHWIRQPPGKGLEWIGVLRAGGSTGYNSALMSRVTISVDTSKNQFSLKLSSVTAADTAVYYCARDHYYYSSYGGFVYWGQGTLVTVSS |
| 38 | 874F7-Hu1 VH | QVQLQESGPGLVKPSETLSLTCTVSGFSLSKYGVHWIRQPPGKGLEWIGVLRAGGSTGYNSALMSRVTISKDTSKSQVSLKLSSVTAADTAVYYCARDHYYYSSYGGFVYWGQGTLVTVSS |
| 39 | 874F7-Hu2 VH | QVQLQESGPGLVKPSETLSLTCTVSGFSLSKYGVHWIRQPPGKGLEWLGVLRAGGSTGYNSALMSRLTISKDSSKSQVSLKLSSVTAADTAVYYCVRDHYYYSSYGGFVYWGQGTLVTVSS |
| 40 | 874F7-HuG, 874F7-Hu1, 874F7-Hu2 VL | DIQMTQSPSSVSASVGDRVTITCLASQTIGAWLAWYQQKPGKSPKLLIYAATRLADGVPSRFSGSGSGTDFTLTISSLQPEDFATYYCQQLDSSPYTFGQGTKVEIK |

Example 1 Immunizing Animals with Antigens and Preparation and Screening of Hybridomas Step 1: Immunizing Mice with Antigens Balb/c mice were routinely intraperitoneal immunized with human IL-33-his protein expressed by prokaryotic recombination. On the first day, the soluble human IL-33-his protein was emulsified with Freund's complete adjuvant or thoroughly mixed with water-soluble adjuvant (quick antibody), then Balb/c mice were injected intraperitoneally (human IL-33-his 50 μg/mouse). On the fourteenth day, the soluble human IL-33-his protein was emulsified with Freund's incomplete adjuvant or fully mixed with water-soluble adjuvant (quick antibody), and Balb/c mice were subjected to intraperitoneal booster immunization (human IL-33-his 50 μg/mouse).0n the thirty-sixth day, the animal was subjected to booster immunization with soluble human IL-33-his protein as the previous time (human IL-33-his 50 μg/mouse). Human IL-33-his was injected intraperitoneally three weeks later for stimulation, and after 3~4 days, the mouse spleen was taken for fusion experiment.

Step 2: Preparation and Screening of Hybridomas 3-4 days after the last booster immunization of mice, mouse spleen cells and mouse myeloma cells SP2/0 were fused by electrofusion apparatus using conventional hybridoma technique protocols. The fused cells were suspended evenly in complete medium, which consisted of RPMI1640 and DMEM F12 medium mixed 1:1 and added with 1% Glutmine, 1% Sodium pyruvate, 1% MEM-NEAA (minimum basic medium-non-essential amino acid solution), 1% Penicillin-streptomycin, 50 μM medium β-mercaptoethanol and 20% FBS (fetal bovine serum). The cells were divided into 36 pieces of 96-well culture plates with $10^5$ cells per 100 μl/well and were cultured overnight. On the next day, 100 μl complete medium containing 2×HAT was added to each well, so that the culture medium in the 96-well plate was 200 μl well (containing 1×HAT). After 7-12 days, the supernatant was harvested and wells containing hybridomas with positive IL-33-his binding activity were screened by indirect enzyme-linked immunosorbent assay (ELISA).

Wherein, the method of indirect enzyme-linked immunosorbent assay used to screen hybridoma wells with positive human IL-33-his binding activity was as follows: recombinant human IL-33-his protein was diluted to 1 μg/ml in a coating solution (50 mM carbonate coating buffer, pH 9.6), added to an enzyme-labeled plate at 100 μl/well, and coated overnight at 4° C. The plate was washed three times with PBST, and blocking solution (2% BSA-PBS) was added at 200 μl/well, and placed at 37° C. for 1 hour, and then washed once with PBST for later use. The collected hybridoma supernatant was added into the blocked enzyme-labeled plate sequentially, 100 μl/well, and the plate was placed at 37° C. for 1 h. The plate was washed with PBST for 3 times, and the HRP-labeled goat anti-mouse IgG secondary antibody was added and the plate was placed at 37° C. for 30 min. After washing the plate with PBST for 5 times, the plate was patted on the absorbent paper to remove residual droplets as far as possible. 100 μl TMB was added to each well, and the plate was placed at room temperature (20±5° C.) for 5 minutes away from light; 50 μ2M $H_2SO_4$ terminating solution was added to each well to terminate the substrate reaction. OD values were read at 450 nm on the microplate reader to analyze the binding ability of the antibody to the target antigen human IL-33-his.

The 10 hybrioma cell lines obtained through screening were expanded in serum-containing complete medium, and centrifuged to replace the medium with serum-free medium SFM medium, so that the cell density was adjusted to 1~2×$10^7$/ml. The cells were cultured at 5% $CO_2$ and 37° C. for 2 weeks. The supernatant was obtained by centrifugation and purified by Protein G affinity chromatography. Ten strains of monoclonal antibody against human IL-33 were obtained. Each antibody was named as 874F7, 871G1, 864F3, 887B9, 858D5, 868H10, 604A8, 604A12, 646F8, 651H2, respectively.

Example 2 Binding Activity of Murine Antibody to Human IL-33 Determined by ELISA The binding ability of murine antibody to human IL-33 protein was determined by indirect enzyme-linked immunosorbent assay (ELISA). The specific methods were as follows: The plate was pre-coated with biotin-avidin (SA) which was diluted in coating solution (50 mM carbonate coating buffer, pH 9.6) to 2 μg/ml at 4° C. overnight, then the plate was blocked with 5% skim milk powder at 37° C. for 2 hours and stored at −80° C. for later use. Biotinylated recombinant human IL-33-his protein was diluted to 0.5 μg/ml in coating solution (50 mM carbonate coating buffer, pH 9.6) and was added at 100 μl/well to the pre-coated SA plate, 37° C., 0.5 h. After washing the plate with PBST for 3 times, the antibodies to be tested were diluted by gradient with 1% BSA buffer and added into the blocked plate at 100 μl/well, and incubated at 37° C. for 1 hour. The plate was washed with PBST for 3 times, and the HRP-labeled goat anti-mouse IgG was added and placed at 37° C. for 30 min. After washing the plate with PBST for 3 times, the plate was patted on the absorbent paper to remove residual droplets as far as possible. 100 μl TMB was added to each well, and the plate was placed at room temperature (20±5° C.) for 5 minutes away from light; 50 μl 2M $H_2SO_4$ terminating solution was added to each well to terminate the substrate reaction. OD values were read at 450 nm on the microplate reader to analyze the binding ability of the antibodies to be tested to the target antigen human IL-33-his.

Figure 1B:
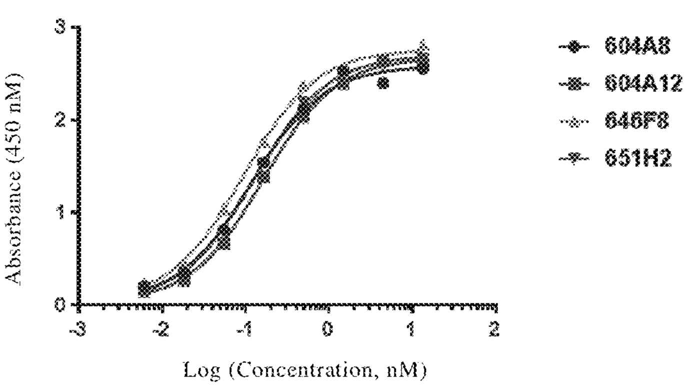

As shown in FIGS. 1A, 1B, all the antibodies represented have good binding activity. The $EC_{50}$ values of 874F7, 871G1, 864F3, 887B9, 858D5 and 868H10 are 0.11 nM, 0.14 nM, 0.27 nM, 0.07 nM, 0.18 nM and 0.36 nM, respectively. The $EC_{50}$ of 604A8, 604A12, 646F8 and 651H2 are 0.11 nM, 0.16 nM, 0.10 nM and 0.13 nM, respectively.

Example 3: Determination of Activity of Murine Antibody Blocking ST2 Binding to IL-33

ST2 is the only receptor for IL-33 that has been discovered so far. As a cytokine, IL-33 exerts its physiological function depending on ST2 signaling pathway, and the blocking activity of antibody can reflect the neutralizing activity thereof. The specific method was as follows: the plate was coated with 2 μg/ml ST2 PBS solution at 4° C. overnight; the plate was washed with PBST for 3 times, then the plated was blocked with 5% skim milk powder at 37° C. for 2 hours; the plate was washed with PBST for 3 times for later use. 20 ng/ml IL-33-his-biotin antigen diluted by 1% BSA was mixed with antibodies to be tested diluted by gradient with 1% BSA at 1:1 equal volume and incubated at 37° C. for hours. The mixture was added to a pre-coated ST2 plate and incubated at 37° C. for 1 h. The plate was washed with PBST for 3 times. HRP-labeled streptavidin secondary antibody was added at 1:8000 and incubated at 37° C. for 0.5 hours. After washing the plate with PBST for 3 times, the plate was patted on the absorbent paper to remove residual droplets as far as possible. 100 μl TMB was added to each well, and the plate was placed at room temperature (20±5° C.) for 5 minutes away from light; 50 μl 2M $H_2SO_4$ terminating solution was added to each well to terminate the substrate reaction. OD values were read at 450 nm on the microplate reader.

Figure 2A:
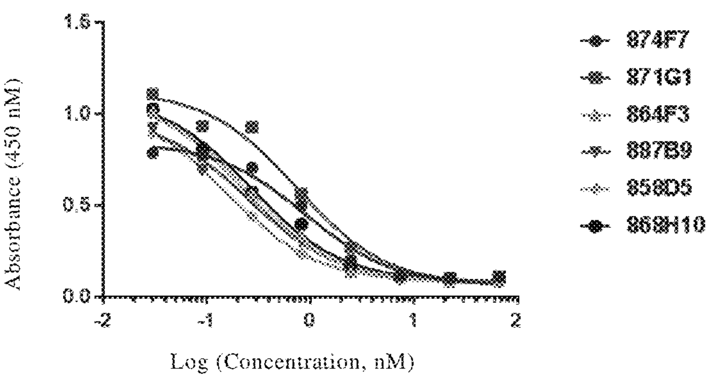
FIG. 2A-2B: Murine antibodies block the activity of ST2 binding to IL-33.
Figure 2B:
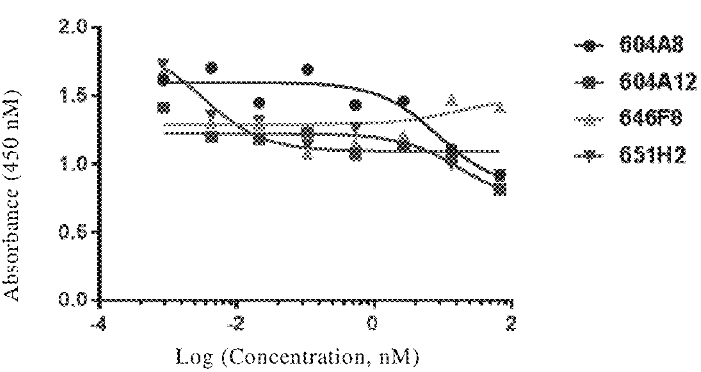

The results are shown in FIGS. 2A and 2B. As shown in FIG. 2A, the antibodies 874F7, 871G1, 864F3, 887B9, 858D5 and 868H10 show good blocking activity, with $IC_{50}$ values of 0.90 nM, 0.74 nM, 0.23 nM, 0.25 nM, 0.16 nM and 0.27 nM, respectively. As shown in FIG. 2B, antibodies 604A8, 604A12, 646F8 and 651H2 have no or very weak blocking activity.

Example 4 Inhibition of IL-33 Induced IL-6 Expression in HUVEC Cells by Murine Antibodies The biological activity of anti-IL-33 antibody was determined using HUVEC cells. The specific methods were as follows: HUVEC cells were cultured in T75 culture bottle, and subcultured to the fifth generation. HUVEC cells in T75 culture bottle were washed with 1×PBS, and digested with 1 ml trypsin for 10 min. When the cells fell off, digestion was terminated with 10 ml culture medium. Cells were counted and seeded into the plate at 100 μl/well, 6000 cells/well. The rest cells were kept in T75 culture bottle for further culture and frozen storage. IL-33-his was diluted to 20 ng/ml by medium, the antibodies to be tested were diluted four times with 8 gradients starting from 40 μg/ml, and four wells whereas blank wells. After dilution, 50 μl of antigen and antibody were added into the cell plate and mixed. That is, the final concentration of IL-33-his was 5 ng/ml. After mixing, the plate was incubated at 37° C. for 12 h-18 h. The supernatant was taken to determine the concentration of IL-6. The detection method can be seen in the instructions of IL-6 kit. IL-6 inhibition rate was calculated according to the following formula and fitting analysis was performed using GraphPad Prism 6 software:

$$\text{Inhibition rate} = (ODAgIL\text{-}33\text{-}OD\ \text{administration})/(ODAgIL\text{-}33\text{-}OD\ \text{blank})\times 100\%$$

Figure 3A:
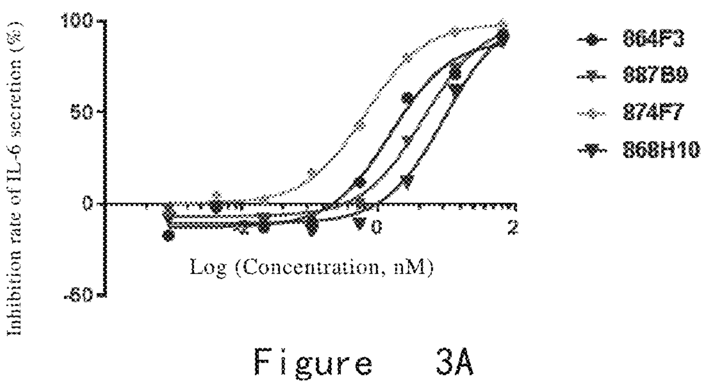
FIG. 3A-3C: Inhibitory effect of murine antibodies on IL-6 expression in HUVEC cells induced by IL-33.
Figure 3B:
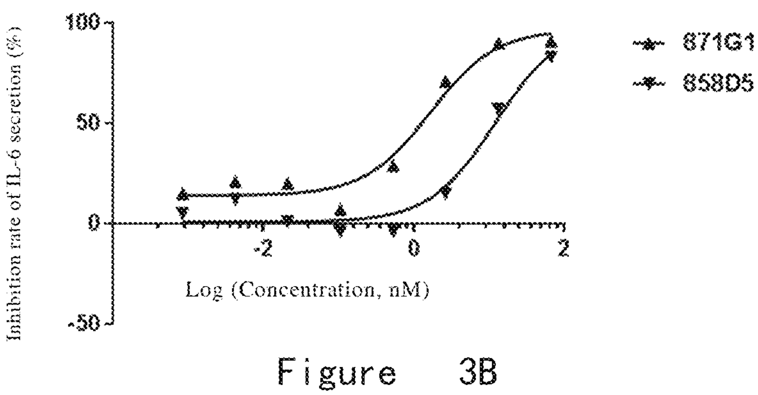
Figure 3C:
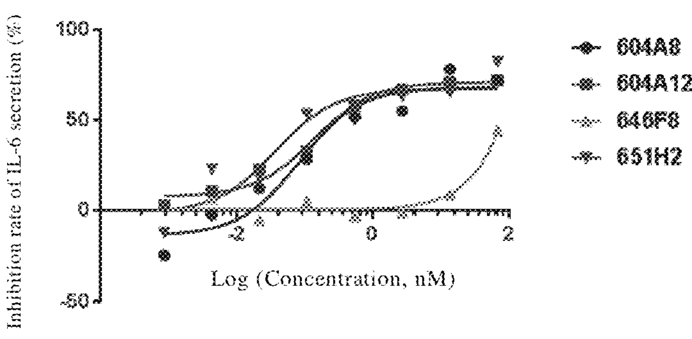

The results are shown in FIGS. 3A, 3B and 3C. The $IC_{50}$ values of inhibition activity of 874F7, 871G1, 864F3, 887B9, 858D5, 868H10, 604A8, 604A12 and 651H2 are 0.65 nM, 1.66 nM, 1.52 nM, 4.53 nM, 12.25 nM, 9.35 nM 0.08 nM, 0.13 nM, and 0.04 nM, respectively. In addition, the maximum inhibition rate of antibodies 604A8, 604A12 and 651H2 is poor.

Example 5 Inhibition of IL-33 Induced IL-8 Expression in HUVEC Cells by Murine Antibodies The biological activity of anti-IL-33 antibody was determined using HUVEC cells. The specific methods were as follows: HUVEC cells were cultured in T75 culture bottle, and subcultured to the fifth generation. HUVEC cells in T75 culture bottle were washed with 1×PBS, and digested with 1 ml trypsin for 10 min. When the cells fell off, digestion was terminated with 10 ml culture medium. Cells were counted and seeded into plate at 100 μl/well, 6000 cells/well. The rest cells were kept in T75 culture bottle for further culture and frozen storage. IL-33-his was diluted to 20 ng/ml by medium, the antibody to be tested was diluted four times with 8 gradients starting from 40 μg/ml, and four wells whereas blank wells. After dilution, 50 μl of antigen and antibody were added into the cell plate and mixed. That is, the final concentration of IL-33-his was 5 ng/ml. After mixing, the plate was incubated at 37° C. for 12 h-18 h. The supernatant was taken to determine the concentration of IL-8. The detection method can be seen in the instructions of IL-8 kit. IL-8 inhibition rate was calculated according to the following formula and fitting analysis was performed using GraphPad Prism 6 software:

Inhibition rate =

$$(ODAgIL-33-OD \text{ administration})/(ODAgIL-33-OD \text{ blank})\times 100\%$$

Figure 4:
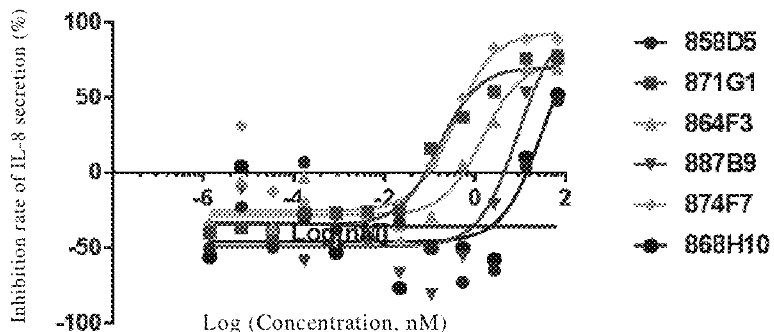
FIG. 4: Inhibitory effect of murine antibodies on IL-8 expression in HUVEC cells induced by IL-33.

As shown in FIG. 4, the activity of antibody 858D5 and 868H10 is very weak, and the $IC_{50}$ values of antibody 874F7, 871G1, 864F3 and 887B9 are 0.35 nM, 0.16 nM, 1.46 nM and 8.90 nM, respectively.

Example 6 Determination of Cross-Activity Between Murine Antibody and Cynomolgus IL-33 Antigen The binding ability of murine antibody to cynomolgus IL-33 was determined by indirect enzyme-linked immunosorbent assay (ELISA). The specific methods were as follows: The plate was pre-coated by biotin-avidin (SA) which was diluted in coating solution (50 mM carbonate coating buffer, pH 9.6) to 2 μg/ml at 4° C. overnight. The plate was blocked with 5% skim milk powder at 37° C. for 2 hours, and stored at −80° C. for later use. Biotinylated recombinant cynomolgus IL-33-his protein was diluted to 1 μg/ml in coating solution (50 mM carbonate coating buffer, pH 9.6) and was added at 100 μl/well to the pre-coated SA plate for 0.5 h at 37° C. After washing the plate with PBST for 3 times, the antibodies to be tested were diluted by gradient with 1% BSA buffer and added into the blocked plate with 100 μl/well, and incubated at 37° C. for 1 hour. The plate was washed with PBST for 3 times, and the HRP-labeled goat anti-mouse IgG was added and placed at 37° C. for 30 min. After washing the plate with PBST for 3 times, the plate was patted on the absorbent paper to remove residual droplets as far as possible. 100 μl TMB was added to each well, and the plate was placed at room temperature (20±5° C.) for 5 minutes away from light; 50 μl 2M $H_2SO_4$ terminating solution was added to each well to terminate the substrate reaction. OD values were read at 450 nm on the microplate reader to analyze the binding ability of the antibody to the target antigen cynomolgus IL-33-his.

Figure 5:
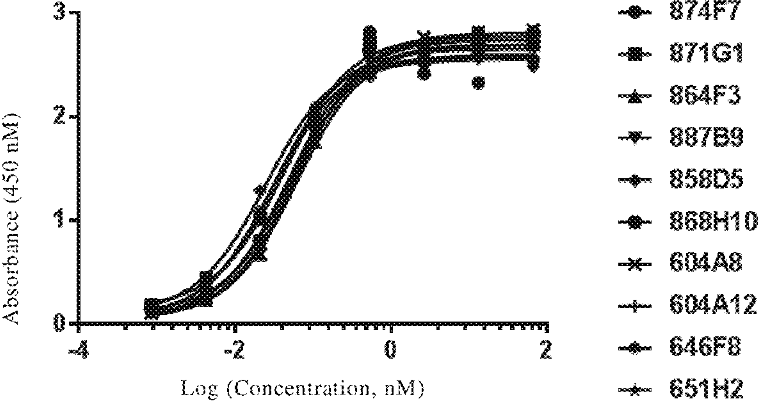
FIG. 5: Cross activity of murine antibodies with cynomolgus IL-33 antigen.

The results are shown in FIG. 5, in which all the antibodies represented can well bind to the cynomolgus IL-33 protein. The $EC_{50}$ values of antibodies 874F7, 871G1, 864F3, 887B9, 858D5, 868H10, 604A8, 604A12, 646F8 and 651H2 are 0.03 nM, 0.04 nM, 0.06 nM, 0.05 nM, 0.02 nM 0.05 nM, 0.06 nM, 0.06 nM, 0.03 nM, and 0.06 nM, respectively.

Example 7: Evaluation of In Vivo Neutralization Activity of Murine Antibodies Intravenous administration of the antigen IL-33 in animals can cause changes in the inflammatory response in vivo, and the proliferation of spleen cells thereby causing an increase in spleen weight, which can be used to evaluate the activity of antibody drugs neutralizating IL-33 in vivo. The specific method was as follows: female BALB/C mice weighing 18-20 g were randomly divided into 6 groups with 10 animals per group. The first group was the normal control group. The second group was the IL-33-his antigen attack group, in which mice were intraperitoneally injected with IL-33 antigen 0.4 ug/mouse every day from the second day of grouping for 6 consecutive days. The third group was the 864F3 treatment group, in which mice were intraperitoneally injected with 864F3 antibody (5 mg/kg) on the day of grouping, and intraperitoneally injected with IL-33 antigen 0.4 ug/mouse every day from the second day after grouping for 6 consecutive days. The fourth group was the 871G1 treatment group, in which mice were intraperitoneally injected with 871G1 antibody (5 mg/kg) on the day of grouping, and intraperitoneally injected with IL-33-his antigen 0.4 ug/mouse every day from the second day after grouping for 6 consecutive days. The fifth group was the 874F7 treatment group, in which mice were intraperitoneally injected with 874F7 antibody (5 mg/kg) on the day of grouping, and intraperitoneally injected with IL-33 antigen 0.4 ug/mouse every day from the second day after grouping for 6 consecutive days. On day 7 after grouping, animals were weighed and euthanized to take the spleens to weigh.

Figure 6:
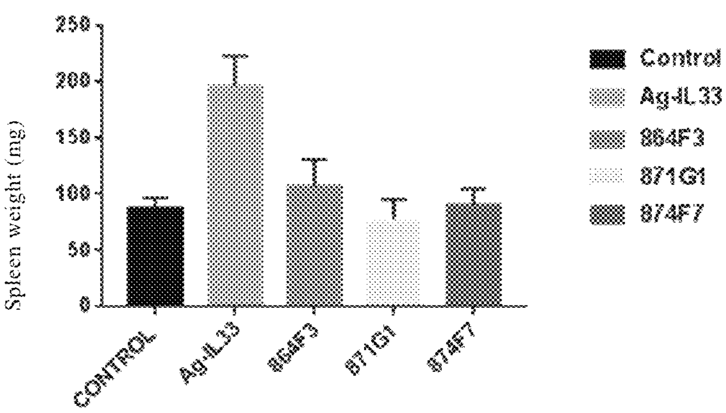
FIG. 6: Evaluation of in vivo neutralization activity of murine antibodies by spleen weighing experiment.

The experimental results are shown in FIG. 6. The average spleen weight of the PBS control group is 86.9±9.4 mg, while the weight of the Ag-IL-33 group is increased obviously as 195.7±26.9 mg. The average spleen weight of 864F3, 871G1 and 874F7 groups is 106.3±24.5 mg, 77.7±17.5 mg and 89.9±14.7 mg, respectively, showing significant neutralizing activity.

Example 8 Preparation of Chimeric Antibody

In the present example, the heavy chain variable region and light chain variable region of hybridomas 864F3, 874F7 and 871G1 were obtained by molecular biology related methods, and further chimeric antibodies were constructed.

RNA of the three hybridoma cells (864F3, 874F7, and 871G1) was extracted by Trizol, and subjected to mRNA reverse transcription to obtain cDNA. cDNA was then used as a template using degenerate primers of heavy and light chains of murine antibodies (Antibody Engineering Volume 1, Edited by Roland Kontermann and Stefan Dubel, the sequence of combination primers was from page 323) for PCR. The PCR products were sequenced and analyzed by kabat database, and the obtained sequences were confirmed to be the variable region sequences of murine antibodies.

Relevant sequence information is as follows:

864F3 has two heavy chain variable region gene sequences, both of which are 363 bp in length, encoding 121 amino acid residues respectively. The nucleotide sequences are shown in SEQ ID NO: 1 and SEQ ID NO: 3, and the amino acid sequences are shown in SEQ ID NO: 2 and SEQ ID NO: 4, respectively. The full length of 864F3 light chain variable region gene sequence is 321 bp, encoding 107 amino acid residues. The nucleotide sequence is shown in SEQ ID NO: 5, and the amino acid sequence is shown in SEQ ID NO: 6.

The full length of 874F7 heavy chain variable region gene sequence is 363 bp, encoding 121 amino acid residues. The nucleotide sequence is shown in SEQ ID NO: 7 and the amino acid sequence is shown in SEQ ID NO: 8. The full length of 874F7 light chain variable region gene sequence is 318 bp, encoding 106 amino acid residues. The nucleotide sequence is shown in SEQ ID NO: 9, and the amino acid sequence is shown in SEQ ID NO: 10.

The full length of 871G1 heavy chain variable region gene sequence is 363 bp, encoding 121 amino acid residues. The nucleotide sequence is shown in SEQ ID NO: 3, and the amino acid sequence is shown in SEQ ID NO: 4. The full length of 871G1 light chain variable region gene sequence is 318 bp, encoding 106 amino acid residues. The nucleotide sequence is shown in SEQ ID NO: 11, and the amino acid sequence is shown in SEQ ID NO: 12.

The homology of 3 H-CDRs and 3 L-CDRs of the three preferred murine anti-IL-33 antibodies is high, especially with the same L-CDR2 (SEQ ID No: 22).

The obtained heavy chain variable region sequence of each hybridoma was spliced with the human IgG4 constant region (comprising S228P mutation) (amino acid sequence is shown in SEQ ID NO: 13), and the light chain variable region sequence was spliced with human kappa chain constant region (amino acid sequence is shown in SEQ ID NO: 14), respectively. The heavy chain and light chain of each chimeric antibody were constructed to pcDNA3.4 expression vector. HEK-293F cells were transfected, and each chimeric antibody was obtained by Protein A purification. The molecular weight of each antibody expressed was determined by SDS-PAGE electrophoresis and SEC-HPLC to be about 150 kD, and the purity of the antibody was >95%. The antibody was quantified, packaged, and frozen at −80° C. for later use.

Example 9 Binding Activity of Each Chimeric Antibody to Human IL-33 Determined by ELISA Method SA protein was diluted to 2 μg/mL to coat ELISA plate at 100 μL/well overnight at 4° C. The plate was washed with PBST (PBS containing 0.05% Tween20) for 3 times, and blocked with 2% BSA prepared in PBS at 200 μL/well, at room temperature for 2 h. After the plate was washed twice with PBST, IL-33-his-biotin protein was diluted to 1 μg/mL with 1% BSA prepared in PBST, and was added to ELISA plate at 100 μL/well. The plate was incubated at room temperature for 1 h, and each monoclonal antibody was diluted with 1% BSA prepared in PBST in a 3-fold gradient. The highest concentration of antibody was 10 μg/mL, and the antibody was diluted for 12 gradients. Each diluted monoclonal antibody was added to ELISA wells with 100 μL/well, and the plate was incubated at room temperature for 1 h. Each sample was added to duplicate wells in parallel. The plate was washed with PBST for 3 times, and HRP-anti human IgG Fc secondary antibody prepared with PBST was diluted at an appropriate ratio, and was added to ELISA wells at 100 μL/well. The plate was incubated at room temperature for 1 h. After washing with PBST for 3 times, TMB developing solution was added at 100 μL/well. When the development met expectations, 2M $H_2SO_4$ was added to terminate the chromogenic reaction at 70 μL/well. Each reaction solution was shaken uniformly and OD450 nm was read on a microplate reader. The data was analyzed and $EC_{50}$ was calculated.

Figure 7:
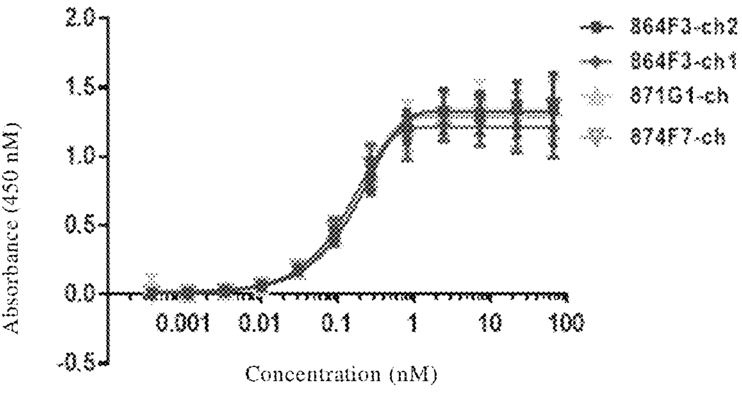
FIG. 7: Binding activity of chimeric antibodies to human IL-33.

The experimental results are shown in FIG. 7. The $EC_{50}$ values of chimeric antibodies 864F3-ch2, 864F3-ch1, 871G1-ch and 874F7-ch are 0.173 nM, 0.127 nM, 0.178 nM and 0144 nM, respectively, indicating that all chimeric antibodies have a good affinity with IL-33.

Example 10: Determination of Activity of Chimeric Antibody Blocking ST2 Binding to IL-33

ST2-Fc protein was diluted to 1 μg/mL with ELISA coating solution to coat ELISA plate with 100 μL/well. The plate was placed in a wet box at 4° C. for 16 h for coating. The ELISA plate was washed 3 times with PBST, and then was blocked with 2% BSA prepared in PBS at 200 μL/well at room temperature for 2 h. The plate was washed once with PBST, and was patted dry to remove the excess blocking solution. Each monoclonal antibody was diluted with 1% BSA prepared in PBST in a 3-fold gradient. The highest concentration of antibody was 10 μg/mL, and the antibody was diluted for 11 gradients. The diluted antibody was mixed 1:1 with 10 ng/ml IL-33-his-biotin, and then the mixture was added into the ELISA well at 100 μL/well. The plate was incubated at room temperature for 1 h. Each concentration was added to duplicate wells in parallel (maximum final concentration of antibody was 20 μg/mL, final concentration of IL-33-his-biotin was 5 ng/mL). Unbound or non-specifically bound primary antibodies were washed out. According to the instructions of the antibody, HRP labeled streptavidin secondary antibody was diluted to an appropriate concentration with antibody diluent solution, then it was added to ELISA plate with 100 μL/well, and was incubated at room temperature for 1 h. The ELISA plate was washed with PBST for 5 times, and was patted dry on absorbent paper to remove excess liquid. TMB developing solution was added with 100 μL/well for development to an appropriate degree. 2M $H_2SO_4$ was added with 70 μL/well to terminate development, and the absorbance was measured at 450 nm on a multifunctional microplate reader. The data were analyzed.

Figure 8:
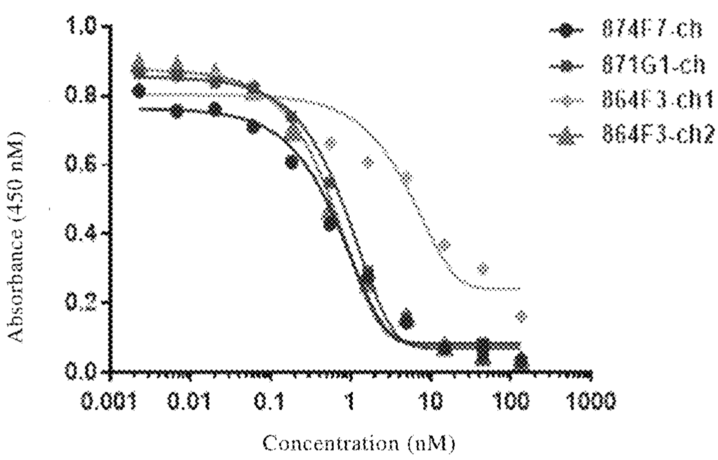
FIG. 8: Chimeric antibodies block the activity of ST2 binding to IL-33.
Figure 9A:
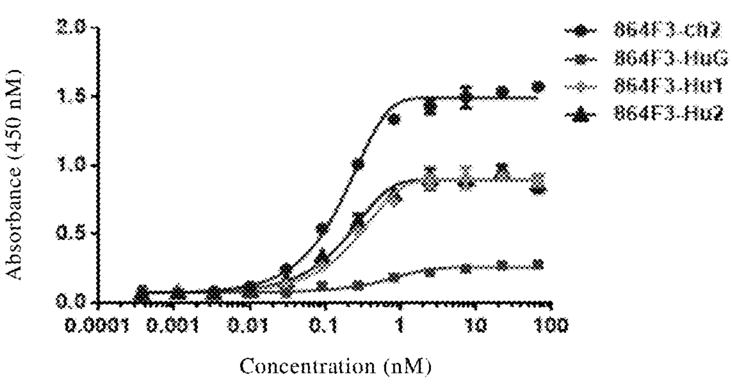
FIG. 9A-9D: Binding activity of each humanized antibody to human IL-33.
Figure 9B:
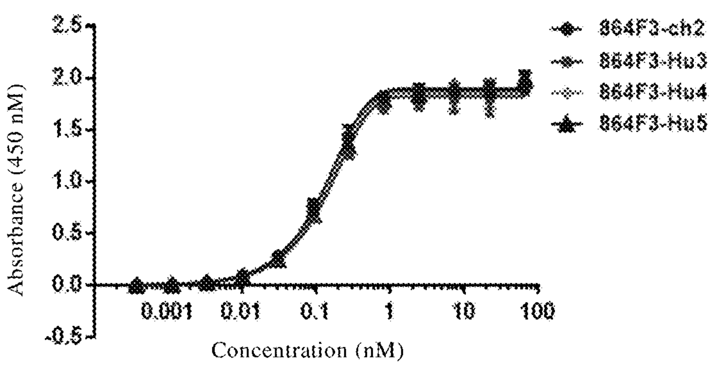
Figure 9C:
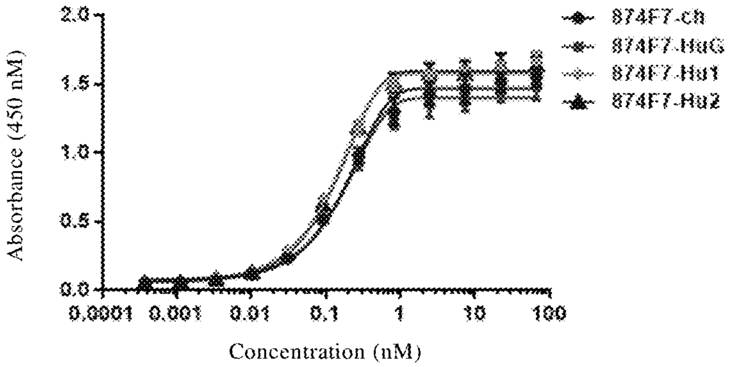
Figure 9D:
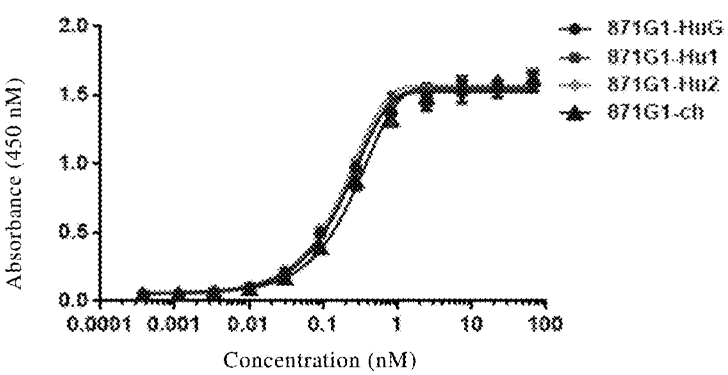

The experimental results are shown in FIG. 8. The $IC_{50}$ values of chimeric antibodies 874F7-ch, 871G1-ch, 864F3-ch1 and 864F3-ch2 are 0.634 nM, 0.853 nM, 45.245 nM and 0.580 nM, respectively, indicating that each chimeric antibody is IL-33 blocking antibody, which can effectively block the binding of IL-33 to its receptor ST2, and 874F7-ch, 871G1-ch and 864F3-ch2 are preferred.

Example 11 Preparation of Humanized Antibodies

The amino acid sequences of the light chain variable region and heavy chain variable region of each candidate murine antibody were analyzed. The complementary determinant regions (CDR) and frame regions (FR) of murine antibody were determined according to the Kabat rule. Wherein, the amino acid sequences of the heavy chain complementary determining regions of 864F3 are

```
HCDR1:
                              (SEQ ID NO: 15)
NYGVH,

HCDR2:
                              (SEQ ID NO: 16)
VIRAGGSSDYNSALMS,

HCDR3:
                              (SEQ ID NO: 17)
DHYFSNSYGGSPY
or

HCDR1:
                              (SEQ ID NO: 18)
KYGVH,

HCDR2:
                              (SEQ ID NO: 19)
VLRAGGTISYNSALMS,

HCDR3:
                              (SEQ ID NO: 20)
DHYYYSSFGGFAS,
```

The amino acid sequences of the light chain complementary determining regions are

LCDR1: (SEQ ID NO: 21)
LASQTIATWLA,

LCDR2: (SEQ ID NO: 22)
AATRLAD
and

LCDR3: (SEQ ID NO: 23)
QQLYNTPYT.

The amino acid sequences of 874F7 heavy chain complementary determining regions are

HCDR1: (SEQ ID NO: 18)
KYGVH,

HCDR2: (SEQ ID NO: 24)
VLRAGGSTGYNSALMS,

HCDR3: (SEQ ID NO: 25)
DHYYYSSYGGFVY,

The amino acid sequences of the light chain complementary determining regions are

LCDR1: (SEQ ID NO: 26)
LASQTIGAWLA,

LCDR2: (SEQ ID NO: 22)
AATRLAD
and

LCDR3: (SEQ ID NO: 27)
QQLDSSPYT.

The amino acid sequences of 871G1 heavy chain complementary determining regions are

HCDR1: (SEQ ID NO: 18)
KYGVH,

HCDR2: (SEQ ID NO: 19)
VLRAGGTISYNSALMS,

HCDR3: (SEQ ID NO: 20)
DHYYYSSFGGFAS,

The amino acid sequences of the light chain complementary determining regions are

LCDR1: (SEQ ID NO: 26)
LASQTIGAWLA,

LCDR2: (SEQ ID NO: 22)
AATRLAD
and

-continued

LCDR3: (SEQ ID NO: 28)
QQLNSTPYT.

The CDR sequences of the murine antibody are shown in Table 1a below:

| | Sequence | SEQ ID NO. |
|---|---|---|
| HCDR1 | NYGVH | 15 |
| | KYGVH | 18 |
| HCDR2 | VIRAGGSSDYNSALMS | 16 |
| | VLRAGGTISYNSALMS | 19 |
| | VLRAGGSTGYNSALMS | 24 |
| HCDR3 | DHYFSNSYGGSPY | 17 |
| | DHYYYSSFGGFAS | 20 |
| | DHYYYSSYGGFVY | 25 |
| LCDR1 | LASQTIATWLA | 21 |
| | LASQTIGAWLA | 26 |
| LCDR2 | AATRLAD | 22 |
| LCDR3 | QQLYNTPYT | 23 |
| | QQLDSSPYT | 27 |
| | QQLNSTPYT | 28 |

The humanized template that best matched the non-FR regions of each of the murine antibodies described above was selected from the Germline database. Then, the CDR regions of murine antibody were transplanted to the selected humanized template to replace the CDR regions of the human template. Then the heavy chain variable region was recombined with the constant region of human IgG4 (including S228P mutation), and the light chain variable region was recombined with the constant region of human kappa chain. At the same time, based on the three-dimensional structure of the antibody, the embedded residues, residues that interact directly with the CDR regions, and residues that have important effects on the conformation of VL and VH of each antibody were subjected to reverse mutation. Finally, a plurality of humanized antibodies was obtained. The sequences of heavy chain and light chain variable regions of each humanized antibody and chimeric antibody are shown in Table 1b. The heavy chain and light chain of each humanized antibody were constructed to pcDNA3.4 expression vector respectively, and pcDNA3.4 expression vectors were transfected into HEK-293F cells to purify each humanized antibody by ProteinA. The molecular weight and purity of the antibodies were determined by SDS-PAGE electrophoresis and SEC-HPLC, and the molecular weight was right and purity was >95%.

TABLE 1b

Sequence listing of variable regions of each humanized antibody

| Antibody | | Amino acid sequence | Nucleotide sequence |
|---|---|---|---|
| 864F3-ch1 | VH | SEQ ID NO: 2 | SEQ ID NO: 1 |
| | VL | SEQ ID NO: 6 | SEQ ID NO: 5 |
| 864F3-ch2 | VH | SEQ ID NO: 4 | SEQ ID NO: 3 |
| | VL | SEQ ID NO: 6 | SEQ ID NO: 5 |
| 874F7-ch | VH | SEQ ID NO: 8 | SEQ ID NO: 7 |
| | VL | SEQ ID NO: 10 | SEQ ID NO: 9 |
| 871G1-ch | VH | SEQ ID NO: 4 | SEQ ID NO: 3 |
| | VL | SEQ ID NO: 12 | SEQ ID NO: 11 |

TABLE 1b-continued

| Sequence listing of variable regions of each humanized antibody | | | |
|---|---|---|---|
| Antibody | | Amino acid sequence | Nucleotide sequence |
| 864F3-HuG | VH | SEQ ID NO: 29 | SEQ ID NO: 41 |
| | VL | SEQ ID NO: 32 | SEQ ID NO: 44 |
| 864F3-Hu1 | VH | SEQ ID NO: 30 | SEQ ID NO: 42 |
| | VL | SEQ ID NO: 32 | SEQ ID NO: 44 |
| 864F3-Hu2 | VH | SEQ ID NO: 31 | SEQ ID NO: 43 |
| | VL | SEQ ID NO: 32 | SEQ ID NO: 44 |
| 864F3-Hu3 | VH | SEQ ID NO: 33 | SEQ ID NO: 45 |
| | VL | SEQ ID NO: 32 | SEQ ID NO: 44 |
| 864F3-Hu4 | VH | SEQ ID NO: 34 | SEQ ID NO: 46 |
| | VL | SEQ ID NO: 32 | SEQ ID NO: 44 |
| 864F3-Hu5 | VH | SEQ ID NO: 35 | SEQ ID NO: 47 |
| | VL | SEQ ID NO: 32 | SEQ ID NO: 44 |
| 874F7-HuG | VH | SEQ ID NO: 37 | SEQ ID NO: 49 |
| | VL | SEQ ID NO: 40 | SEQ ID NO: 52 |
| 874F7-Hu1 | VH | SEQ ID NO: 38 | SEQ ID NO: 50 |
| | VL | SEQ ID NO: 40 | SEQ ID NO: 52 |
| 874F7-Hu2 | VH | SEQ ID NO: 39 | SEQ ID NO: 51 |
| | VL | SEQ ID NO: 40 | SEQ ID NO: 52 |
| 871G1-HuG | VH | SEQ ID NO: 33 | SEQ ID NO: 45 |
| | VL | SEQ ID NO: 36 | SEQ ID NO: 48 |
| 871G1-Hu1 | VH | SEQ ID NO: 34 | SEQ ID NO: 46 |
| | VL | SEQ ID NO: 36 | SEQ ID NO: 48 |
| 871G1-Hu2 | VH | SEQ ID NO: 35 | SEQ ID NO: 47 |
| | VL | SEQ ID NO: 36 | SEQ ID NO: 48 |

Example 12 Binding Activity of Each Humanized Antibody to Human IL-33 Determined by ELISA Method The binding affinity of the above humanized antibodies to human IL-33 was determined by ELISA, and the relevant experimental methods were referred to Example 9.

The experimental results were shown in FIG. 9A-9D. The $EC_{50}$ values of chimeric antibody 864F3-ch2 and humanized antibodies 864F3-HuG, 864F3-Hu1 and 864F3-Hu2 are 0.169 nM, 0.760 nM, 0.249 nM and 0.181 nM, respectively. Compared with chimeric antibody 864F3-ch2, humanized antibodies 864F3-HuG, 864F3-Hu1 and 864F3-Hu2 show more loss of affinity to human IL-33. The $EC_{50}$ values of chimeric antibodies 864F3-ch2, 864F3-Hu3, 864F3-Hu4 and 864F3-Hu5 are 0.124 nM, 0.138 nM, 0.135 nM and 0.146 nM, respectively. Compared with chimeric antibody 864F3-ch2, the affinity of 864F3-Hu3, 864F3-Hu4 and 864F3-Hu5 to human IL-33 is almost unchanged.

The $EC_{50}$ values of chimeric antibody 874F7-ch and humanized antibodies 874F7-Hμg, 874F7-Hu1 and 874F7-Hu2 are 0.177 nM, 0.170 nM, 0.129 nM and 0.136 nM, respectively. Compared with chimeric antibody 874F7-ch, humanized antibodies 874F7-Hu1 and 874F7-Hu2 show no loss of affinity to human IL-33.

The $EC_{50}$ values of chimeric antibody 871G1-ch and humanized antibodies 871G1-HuG, 871G1-Hu1 and 871G1-Hu2 are 0.255 nM, 0.187 nM, 0.191 nM and 0.176 nM, respectively. Compared with chimeric antibody 871G1-ch, all of humanized antibodies 871G1-Hu1, 871G1-Hu2 and 871G1-HuG do not lose their affinity to human IL-33.

Example 13 Determination of Activity of Humanized Antibody Blocking ST2 Binding to IL-33

The blocking effect of the above humanized antibodies on the binding of IL-33 to its receptor ST2 was determined by the ELISA method, and the relevant experimental methods were referred to Example 10.

Figure 10:
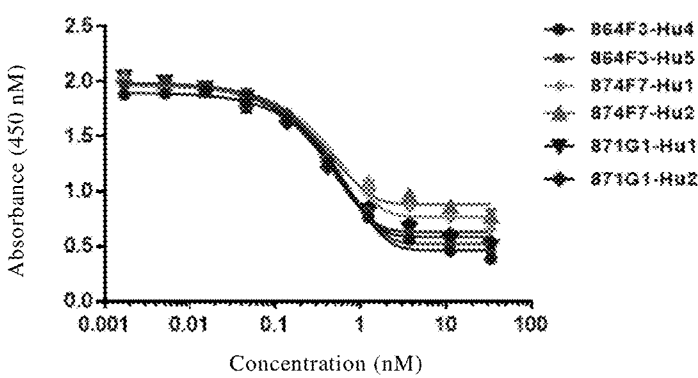
FIG. 10: Humanized antibodies block the activity of ST2 binding to IL-33.

The experimental results are shown in FIG. 10. The IC50 values of humanized antibodies 864F3-Hu4, 864F3-Hu5, 871G1-Hu1, 871G1-Hu2, 874F7-Hu1 and 874F7-Hu2 to block the binding of IL-33 to ST2 protein are 0.512 nM, 0.473 nM, 0.404 nM, 0.361 nM, 0.451 nM, 0.350 nM, respectively. These results indicate that all humanized antibodies retained the blocking effect on the binding of IL-33 to ST2.

Example 14 Determination of Binding Kinetics of Humanized Monoclonal Antibody to IL-33

A chip with covalently coupled Protein A/G (purchased from GE Healthcare, catalog number BR-1005-30) was used to capture each antibody to be tested, and the relevant operating parameters were as follows: The antibody concentration was 2 g/mL, the contact time was 75 s, the flow rate was 10 L/min, and the regeneration contact time was 30 s. The IL-33-his antigen was diluted with HBS-EP pH7.4 buffer solution (purchased from GE Healthcare, catalog number BR-1006-69). The maximum concentration was 50 nM, and diluted to 0.39 nM by two-fold dilution. Duplicate wells and 0 concentration point well were set, and 6M guanidine hydrochloride solution was used as the regeneration buffer. The sample was injected on Biacore 8K according to the following parameters, the binding time was 180 s, the dissociation time was 900 s, the flow rate was 30 μL/min, and the regeneration contact time was 30 s. After running, Biacore 8K Evaluation Software was used to analyze the data according to the "1:1 binding kinetics model", and the binding kinetics parameters of each antibody to IL-33 were obtained.

The results are shown in Table 2. The binding constants (ka), dissociation constants (kd) and equilibrium dissociation constants (KD) of all humanized antibodies are at the same level.

TABLE 2

| Binding kinetics parameters of each humanized antibody to IL-33 | | | |
|---|---|---|---|
| Sample | ka (1/Ms) | kd (1/s) | KD (M) |
| 864F3-Hu4 | 3.23E+05 | 4.47E−04 | 1.38E−09 |
| 864F3-Hu5 | 3.23E+05 | 4.39E−04 | 1.36E−09 |
| 874F7-Hu1 | 2.02E+05 | 5.70E−04 | 2.82E−09 |
| 874F7-Hu2 | 1.94E+05 | 5.76E−04 | 2.97E−09 |
| 871G1-Hu1 | 2.95E+05 | 5.04E−04 | 1.71E−09 |
| 871G1-Hu2 | 3.00E+05 | 5.27E−04 | 1.76E−09 |

Example 15 Inhibitory Effect of Humanized Antibodies on IL-6 Expression in HUVEC Cells Induced by IL-33

In this example, the activity of each humanized antibody was evaluated by measuring the inhibitory effect of each humanized antibody on IL-6 expression in HUVEC cells induced by IL-33-his protein. The specific experimental steps were as follows: HUVEC cells in T75 culture bottle were digested and counted, and the cells were placed in complete culture medium with 100 μL/well and 6000 cells/well, then were cultured in an incubator at 37° C. for 2 h. The drug was administered after the cells were adhered to the wall. The antibody to be tested was diluted with complete medium with the highest concentration of 200 nM, and was diluted 5 times with 9 gradients. The positive blank control and negative blank control were set. After dilution, the antibody was mixed with 20 ng/mL IL-33-his at a volume ratio of 1:1 (the highest final concentration of antibody after being added to cells was 50 nM, and the final concentration of IL-33-his was 5 ng/mL). After incubating at room temperature for 30 min, 100 μL antibody/IL-33-his mixture was added into the cell suspension and mixed gently. After 20 h in a $CO_2$ incubator at 37° C., the supernatant was collected by centrifugation and stored at −80° C. for IL-6 determination.

Rat-Anti-human IL-6 protein was diluted to 2.5 μg/mL by ELISA coating solution to coat an ELISA plate at 100 μL/well. The plate was placed in a wet box at 4° C. for 16 h for coating. The ELISA plate was washed 3 times with PBST to remove unbound protein and was patted dry on the absorbent paper to remove the excess blocking solution, then the plate was blocked with 2% BSA prepared in PBS with 200 μL/well at room temperature for 1-2 h. The IL-6 standard was diluted with 1% BSA prepared in PBS in a 3-fold gradient with the highest concentration of 30 ng/mL. After evenly mixed, the mixture was added into the ELISA wells at 100 μL/well. 100 μL/well of the above cell supernatant was added to the ELISA wells, and the plate was incubated at room temperature for 1 h. Each sample for the standard curve was set to 2 duplicates in parallel. The unbound or non-specifically bound primary antibodies were washed out and biotin Rat Anti Human IL-6 was diluted with antibody diluent at 1:1000, which was mixed evenly and added into ELISA wells at 100 μL/well. After incubating at room temperature for 1 h, the unbound or non-specifically bound antibodies were washed out. HRP-labeled streptavidin secondary antibody was diluted to an appropriate concentration and added into the ELISA plate at 100 μL/well. After incubating at room temperature for 1 h, the ELISA plate was washed with PBST for 5 times, and it was patted dry on absorbent paper to remove excess liquid. TMB developing solution was added for development to an appropriate degree. 2M $H_2SO_4$ was added at 50 μL/well to terminate development, and the absorbance was measured at 450 nm on a multifunctional microplate reader. The data were analyzed.

Figure 11:
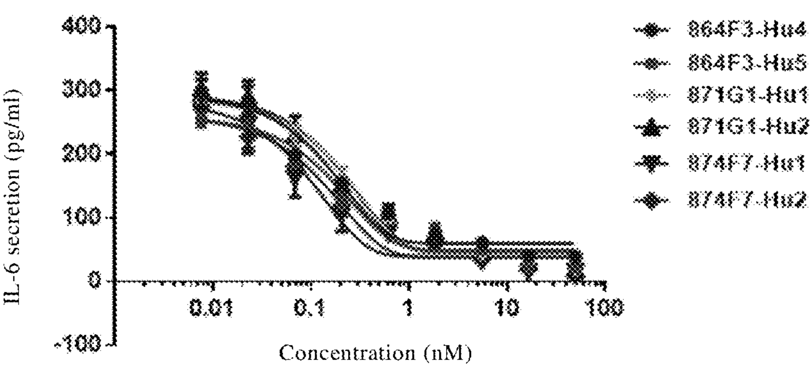
FIG. 11: Inhibitory effect of humanized antibodies on IL-6 expression in HUVEC cells induced by IL-33.

The experimental results are shown in FIG. 11. The $IC_{50}$ values of the inhibitory effect of humanized antibodies 864F3-Hu4, 864F3-Hu5, 871G1-Hu1, 871G1-Hu2, 874F7-Hu1 and 874F7-Hu2 on IL-6 expression in HUVEC cells induced by IL-33 are 0.073 nM and 0.147 nM, 0.210 nM, 0.175 nM, 0.051 nM, 0.050 nM, respectively. These results indicate that all humanized antibodies can effectively inhibit IL-6 secretion in HUVEC cells induced by IL-33-his protein, especially, 874F7-Hu1 and 874F7-Hu2, which have better effects.

Example 16 Inhibitory Effect of Humanized Antibodies on IFNγ Secretion of PBMC Induced by IL-33

In this example, the activity of each humanized antibody was evaluated by measuring the inhibition on IFN-γsecretion of PBMC induced by IL-33-his protein. The specific experimental steps were as follows: fresh PBMC was centrifuged and counted, and washed once with PBS, and was diluted to $4\times10^6$ cells/Ml with complete medium RPMI1640. PBMC cells were added into a 96-well U-shaped culture plate, 50 μL ($2\times10^5$ cells/well) per well, and were placed in an incubator at 37° C. for recovery. The antibody was diluted with RPMI1640 complete medium with a maximum concentration of 200 nM (final concentration of 50 nM), in a 3-fold gradient dilution. After dilution, an equal volume of 40 ng/mL IL-33-his (final concentration of 10 ng/mL) was added to each well, and was incubated at 37° C. for 30 min. 50 μL of 40 ng/mL IL-12 diluted by complete medium was added into the above PBMC cell culture plate, then 100 μL mixture of antibody and IL-33-his was added. After mixing evenly, the mixture was cultured in a cell incubator at 37° C. for 24 h. The cell culture plate was centrifuged at 500 g for 5 min, and 180 μL supernatant was absorbed from each well for detection.

(purchased from BD Biosciences, catalog number 551221) was diluted to 1 μg/mL with ELISA coating solution to coat an ELISA plate at 100 μL/well. The plate was placed in a wet box at 4° C. for 16 h for coating. The ELISA plate was washed 3 times with PBST, and was patted dry on absorbent paper to remove the excess blocking solution, then the plate was blocked with 2% BSA prepared in PBS with 200 μL/well at room temperature for 1-2 h. The ELISA plate was washed once to remove excess blocking solution, and was patted dry to remove excess liquid. The IFNγ standard was diluted in half with 12 gradients with the highest concentration of 250 ng/mL. Then it was added into the ELISA wells at 100 μL/well, and each sample was set to 2 duplicates in parallel. 100 μL of the above cell supernatant was added to the ELISA plate and the plate was incubated at room temperature for 1 h. The plate was washed with PBST for three times and biotin mouse-anti-human IFNγ (purchased from BD Biosciences, catalog number 554550) which diluted with 1% BSA PBST at 1:1000 was added at 100 μL/well. The plate was incubated at room temperature for 1 h, and the unbound or non-specifically bound antibodies were washed out. According to the instructions of the antibody, HRP-labeled Streptavidin (purchased from BD, catalog number 554066) was diluted with 1% BSA PBST to an appropriate concentration, then it was added to ELISA plate at 100 μL/well, and the plate was incubated at room temperature for 1 h. The ELISA plate was washed with PBST for 5 times, and was patted dry on absorbent paper to remove excess liquid. TMB developing solution was added at 100 μL/well for development to an appropriate degree. The color 2M $H_2SO_4$ was added at 50 μL/well to terminate development, and the absorbance was measured at 450 nm on a multifunctional microplate reader. The data were analyzed.

Figure 12:
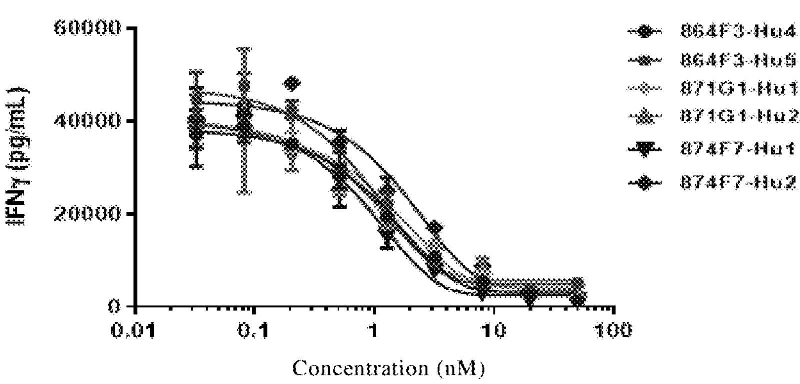
FIG. 12: Inhibitory effect of humanized antibodies on IFNγ secretion of PBMC induced by IL-33.

The experimental results are shown in FIG. 12. The $IC_{50}$ values of the inhibitory effect of humanized antibodies 864F3-Hu4, 864F3-Hu5, 871G1-Hu1, 871G1-Hu2, 874F7-Hu1 and 874F7-Hu2 on the IFN-γ secretion of PBMC induced by IL-33 are 1.224 nM, 0.839 nM and 1.395 nM, 1.061 nM, 0.850 nM, and 1.736 nM, respectively. These results indicate that all humanized antibodies can effectively inhibit the IFNγ secretion of human PBMC induced by IL-33-his protein, wherein the activity of 874F7-Hu2 is relatively poor.

Example 17: Inhibitory Effect of Humanized Antibodies on IFNγ Secretion of Nk Cells Induced by IL-33

Fresh PBMCS were centrifuged and counted, and NK cells were isolated according to the instructions of Nk Cell Isolation Kit human (purchased from Miltenyi, catalog number 130-092-657). NK cells were washed twice with PBS and then counted. Cells were diluted to $0.8\times10^6$ cells/mL with 1640+10% FBS+1% Glutamax medium, and were seeded into a 96-well cell culture plate at 50 μL cell suspension per well. Each antibody was diluted with 1640+10% FBS+1% Glutamax medium, and the final maximum concentration was 100 nM with gradient dilution of ¼. After dilution, IL-33-his with a final concentration of 10 ng/mL was added to each well and incubated in a cell incubator at 37° C. for 30 min. Subsequently, IL-12 with a final concentration of 2 ng/mL diluted by complete medium was added to the 96-well cell culture plate containing NK cells, and finally the above 100 μL mixture of antibody and IL-33 was added. After incubating at a cell culture incubator at 37° C. for 24 h, cell culture supernatant was collected to determine the secretion level of IFNγ.

Figure 13:
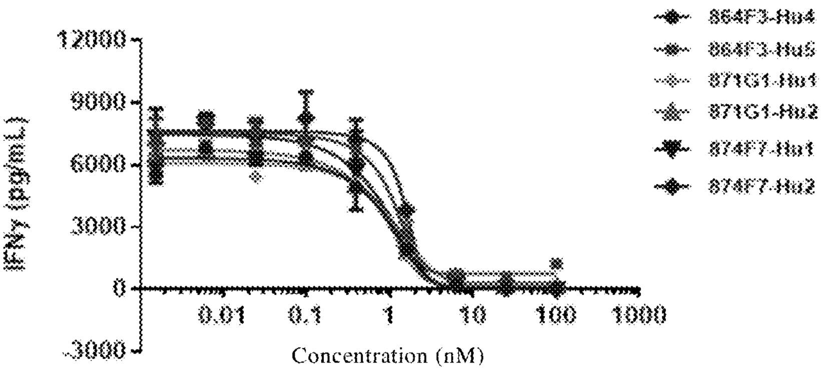
FIG. 13: Inhibitory effect of humanized antibodies on IFNγ secretion of NK cells induced by IL-33.

The method of IFNγ detection was referred to Example 16. The experimental results are shown in FIG. 13. The humanized antibodies 864F3-Hu4, 864F3-Hu5, 871G1-Hu1, 871G1-Hu2, 874F7-Hu1 and 874F7-Hu2 have inhibitory effects on IL-33 to induce the secretion of IFNγ by NK cells, and the $IC_{50}$ values are 0.904 nM, 1.021 nM, 0.851 nM, 0.900 nM, 0.742 nM and 1.559 nM, respectively.

Example 18 Inhibitory Effect of Humanized Antibodies on IL-5 and IL-13 Secretion of KU812 Cells Induced by IL-33

Basophilic leukemia cells KU812 at logarithmic growth stage were collected, centrifuged, counted, and resuspended with IMDM medium containing 20% FBS (complete medium, purchased from Gibco, No. 11965-092). 96-well cell culture plates were prepared with 20,000 cells per well. Each antibody to be tested was prepared with complete medium in a 3-fold gradient dilution as the administration group, each group was continuously diluted with 9 gradients, the maximum working concentration of the antibody was 200 μg/mL. At the same tome, IL-33-his was prepared with complete medium at a working concentration of 700 ng/ml. After mixing evenly at 1:1, the mixture was added to the above 96-well cell culture plate, and the final volume of each well was 200 μL. The unadministered group was set as a negative control, and only IL-33 was added as the single drug control group. Each concentration was set to 2 duplicates in parallel, and the culture was continued in a cell culture incubator at 37° C. for 48 h. The supernatant was collected for the determination of secretion of IL-5 and IL-13.

Antibodies anti-human IL-5 (purchased from BD, catalog number 554488) and anti-human IL-13 (purchased from BD, catalog number 554570) were diluted to 5 ug/ml with ELISA coating solution to coat an ELISA plate at 100 μL/well. The plate was placed in a wet box at 4° C. for 16 h for coating. The ELISA plate was washed three times with PBST to remove the unbound antigens, and was patted dry on absorbent paper to remove the excess liquid, then the plate was blocked by 2% BSA prepared in PBS at 200 μL/well at room temperature for 1 h. The ELISA plate was washed with PBST once to remove excess blocking solution, and was patted dry to remove the excess liquid. The hu-IL-5 standard was diluted with 1% BSA prepared in PBST in a 3-fold gradient with the highest concentration of antibody of 50 μg/mL, and with 12 gradients, then it was added to ELISA wells with 100 μL/well, and the plate was incubated at room temperature for 1 h. Each sample was set to 2 duplicates in parallel. The collected cell supernatant was added at 100 μL/well. Hu-IL-13 standard was diluted with 1% BSA prepared in PBST in a 3-fold gradient, with the highest concentration of 10 ng/mL, and with 12 gradients, then it was added to ELISA wells with 100 μL/well, and the plate was incubated for 2 h at room temperature. Each sample was set to 2 duplicates in parallel The collected cell supernatant was added at 50 μL/well. Unbound or non-specifically bound primary antibodies were washed out, and Biotin-anti-human-IL-5 (purchased from BD, catalog number 554491) and Biotin-anti-human-IL-13 (purchased from BD, catalog number 555054) secondary antibody were diluted with antibody diluents to an appropriate concentration, then were added to the ELISA plate at 100 μL/well, and the plate was incubated at room temperature for 2 h. The ELISA plate was washed with PBST for three times, and patted dry on absorbent paper to remove the excess liquid. The HRP-labeled Streptavidin (purchased from BD, catalog number 554066) was diluted with antibody diluent to an appropriate concentration, and added to the ELISA plate at 100 μL/well, and the plate was incubated at room temperature for 0.5 h. The ELISA plate was washed with PBST three times, and patted dry on absorbent paper to remove the excess liquid. TMB developing solution was added at 100 μL/well for development to an appropriate degree. 2M $H_2SO_4$ was added at 50 μL/well to terminate development, and the absorbance was measured at 450 nm on a multi-functional microplate reader. The data were analyzed.

Figure 14:
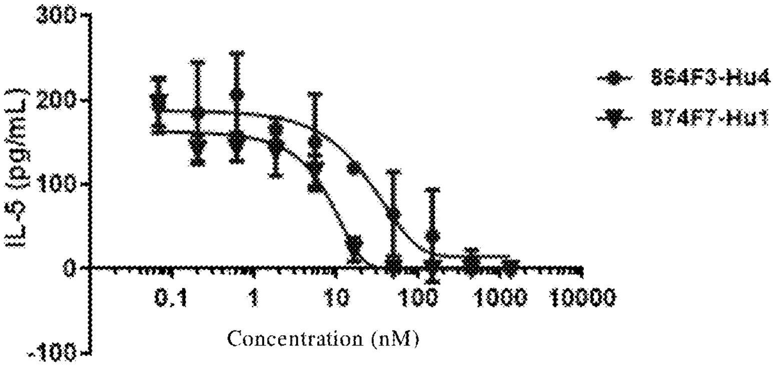
FIG. 14: Humanized antibodies 864F3-Hu4 and 874F7-Hu1 effectively inhibit IL-5 secretion of KU812 cells induced by IL-33.

As shown in FIG. 14, humanized antibodies 864F3-Hu4 and 874F7-Hu1 can effectively inhibit IL-5 secretion of KU812 cells induced by IL-33, with IC50 values of 27.605 nM and 7.828 nM, respectively.

Figure 15:
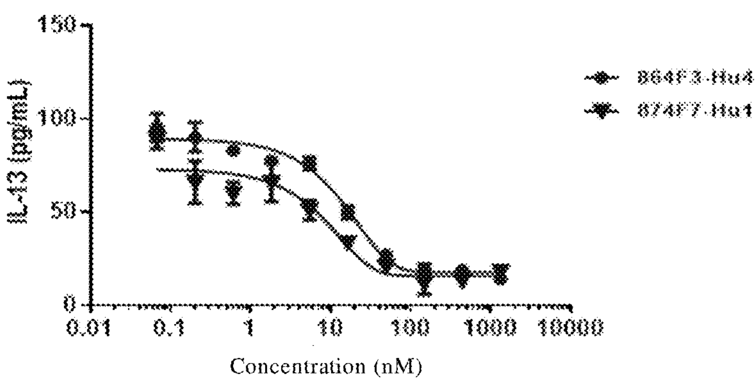
FIG. 15: Humanized antibodies 864F3-Hu4 and 874F7-Hu1 effectively inhibit IL-13 secretion of KU812 cells induced by IL-33.

As shown in FIG. 15, humanized antibodies 864F3-Hu4 and 874F7-Hu1 can also effectively inhibit IL-13 secretion of KU812 cells induced by IL-33, with IC50 values of 14.745 nM and 5.219 nM, respectively.

Example 19 Cross-Reactivity of Humanized Antibodies to Different Species of IL-33 Protein The experimental methods were referred to Example 14, in which the antigens cynomolgus IL-33 protein (purchased from Sino catalog number 90912-CNAE) and mouse IL-33 protein (purchased from R&D, 3626-ML-010/CF) were used, and human IL-33 protein was used as the control. The experimental results are shown in Table 3. Both 864F3-Hu4 and 874F7-Hu1 cross-react with cynomolgus IL-33 protein, and are consistent with the characteristics of each antibody binding to human IL-33 protein. In addition, 864F3-Hu4 and 874F7-Hu1 also cross-react with mouse IL-33 protein to some extent, but the affinity is significantly lower than that of binding with human IL-33 protein.

TABLE 3

Cross-reactivity of humanized antibodies to cynomolgus and mouse IL-33 protein

| | Human IL-33 | | | Cynomolgus monkeys IL-33 | | | Mouse IL-33 | | |
|---|---|---|---|---|---|---|---|---|---|
| Sample | ka (1/Ms) | kd (1/s) | KD (M) | ka (1/Ms) | kd (1/s) | KD (M) | ka (1/Ms) | kd (1/s) | KD (M) |
| 864F3-Hu4 | 2.70E+05 | 1.49E−04 | 5.52E−10 | 3.85E+05 | 2.45E−04 | 6.37E−10 | 1.08E+05 | 2.05E−02 | 1.90E−07 |
| 874F7-Hul | 1.80E+05 | 2.04E−04 | 1.13E−09 | 2.73E+05 | 3.49E−04 | 1.27E−09 | 6.40E+04 | 2.12E−03 | 3.32E−08 |

Example 20 Evaluation of In Vivo Neutralizing Activity of Humanized Antibodies

The specific experimental procedure was referred to Example 7, with 10 BALB/C mice in each experimental group.

Figure 16:
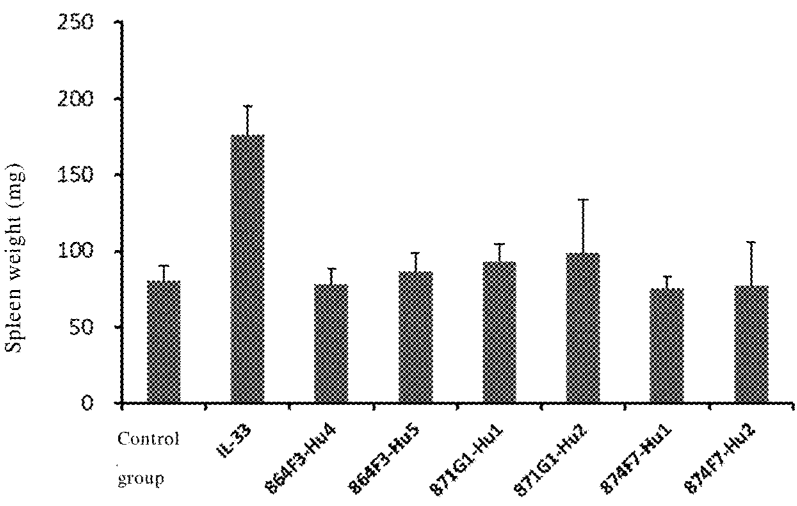
FIG. 16: Evaluation of pharmacodynamic activity of humanized antibodies by spleen weighing assay.

As shown in FIG. 16, the results show that the weight of spleen in the IL-33 antigen group is increased significantly compared with the control group (spleen weight 80.55 mg), which is 176.49 mg. The average spleen weight in the 864F3-Hu4, 864F3-Hu5, 871G1-Hu1, 871G1-Hu2, 874F7-Hu1 and 874F7-Hu2 antibody groups are 78.39 mg, 86.6 mg, 92.82 mg, 98.87 mg, 75.63 mg and 77.49 mg, respectively, which indicates that all humanized antibodies have obvious neutralizing activity in vivo.

Figure 17:
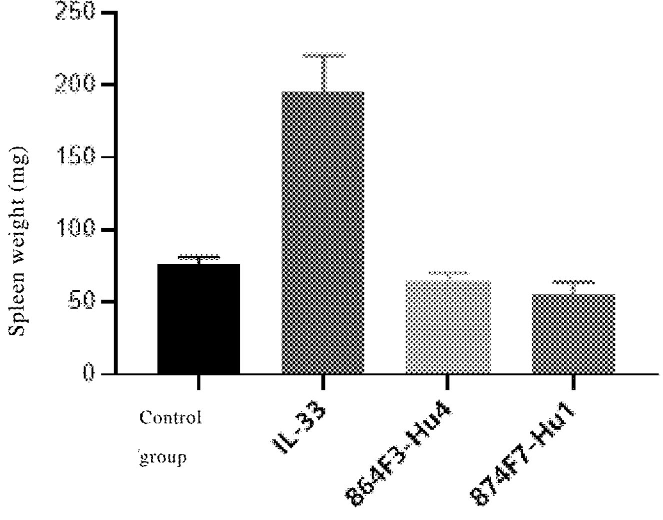
FIG. 17: Evaluation of the in vivo pharmacodynamic activity of humanized antibodies 864F3-Hu4 and 874F7-Hu1 by spleen weighing assay.

Example 21 Determination of In Vivo Pharmacodynamic Activity of Humanized Antibodies The experimental method was referred to Example 7. As shown in FIG. 17, after intrapitoneal injection of human IL-33, spleen enlargement of mice was significantly stimulated (IL-33 group), and spleen weight was about 194.6 mg, while that of the control group (without human IL-33 stimulation) was 76.1 mg. Single treatment with 5 mg/kg 864F3-Hu4 and 874F7-Hu1 could effectively inhibit spleen enlargement in mice, with spleen weight of 65.4 mg and 55.9 mg, respectively.

At the end of the experiment, mice in each group were euthanized, and eosinophils and IL-5 levels in peripheral blood were detected respectively.

Part of the whole blood of the above mice was taken out and placed in an common EP tube, which was placed at 4° C. for more than 5 h to make complete coagulation. After coagulation, the EP tube was placed in a 4° C. pre-cooled centrifuge for centrifugation at 8000 rmp for 6 min. After centrifugation, the serum was taken out and placed in a new centrifuge tube, and was centrifuged again at 8000 rmp at 4° C. for 6 min. After centrifugation, the supernatant was taken out, packaged and stored in −80° C. Standard and serum samples to be tested were diluted according to the instructions for the BD CBA Mouse Enhanced Sensitivity Master Buffer Kit (purchased from BD biosciences, catalog number 562246). Subsequently, each sample was processed according to the instructions of Mouse IL-5 Enhanced Sensitivity Flex Set (purchased from BD biosciences, catalog number 562234). After the detection parameters were set, the samples were detected by Flow cytometer (BD FACSCelesta). The above data were analyzed by GraphPad Prism, and the content of IL-5 in serum samples of each experimental group was calculated according to the standard curve.

Figure 18:
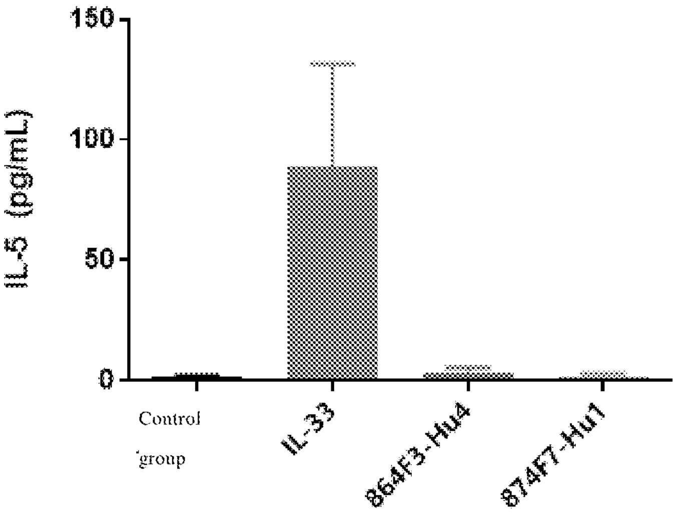
FIG. 18: Humanized antibodies 864F3-Hu4 and 874F7-Hu1 effectively inhibit IL-5 secretion in peripheral blood of mice.

The experimental results are shown in FIG. 18. Compared with the control group (without stimulation of human IL-33), intraperitoneal injection of human IL-33 can significantly stimulate the secretion of IL-5 in peripheral blood of mice (IL-33 group), about 78.6 times. When 5 mg/kg 864F3-Hu4 and 874F7-Hu1 were administered for a single treatment, the secretion of IL-5 in peripheral blood of mice was effectively inhibited by 1.7 times and 0.9 times of the control group, respectively.

Part of the whole blood of the above mice was taken out and placed in an EDTA anticoagulant tube, mixed upside down evenly, and the tube was placed at 4° C. for later use. 10 mL of round-bottom centrifuge tubes were taken and 2 μL of mouse Fc blocker (purchased from BD biosciences, catalog number 553142) was added to each tube. 50 μL of blood sample was taken from each sample in a 10 mL centrifuge tube and the mixture was gently pipetted to mix the blood sample with the blocker. The tube was incubated on ice for 15 min. 2 μL of the three mixed antibodies (0.5 μL CD45.2 Monoclonal Antibody (104), PerCP-Cyanine5.5 (purchased from eBioscience™, catalog number 45-0454-82), 0.5 μL CD170 (Siglec F) Monoclonal Antibody (1RNM44N), PE (purchased from eBioscience™, catalog number 12-1702-82), 1 μL Ly-6G/Ly-6C Monoclonal Antibody (RB6-8C5), APC-eFluor 780 (purchased from eBioscience™, catalog number 47-5931-82)) were added to each centrifuge tube, and the tube was incubated on ice for 1 h away from light. 500 mL 1× Lysing buffer (purchased from BD Biosciences, catalog number 555899) was added to the centrifuge tube and mixed evenly, and the erythrocytes were lysed at room temperature for 5 min. The tube was centrifuged at 350 g for 5 min to discard the supernatant. 3 mL of pre-cooled PBS cells (had been washed) were added into the tube and the tube was centrifuged at 350 g for 5 min. The supernatant was discarded, and 500 μL pre-cooled and filtered PBS was added into the tube, and the settling cells were sprung up gently. The cell suspension was filtered into the flow tube by cell sieve, and the proportion of eosinophils to leukocytes in each sample was analyzed by flow cytometer.

Figure 19:
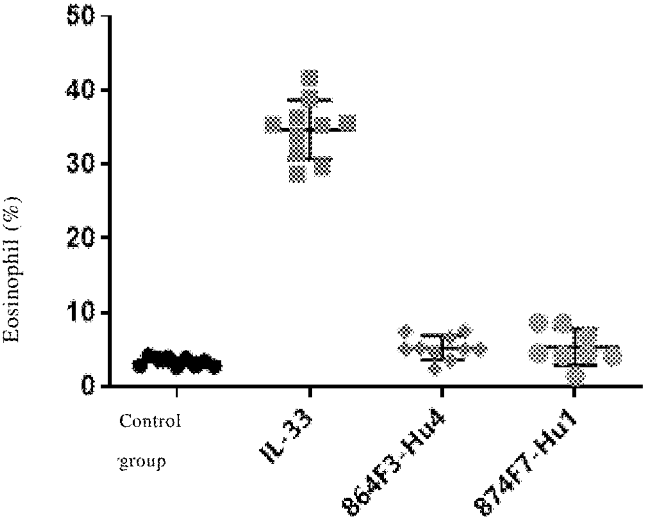
FIG. 19: Humanized antibodies 864F3-Hu4 and 874F7-Hu1 effectively reduce the increase of eosinophils stimulated by human IL-33 in peripheral blood of mice.
Figure 20:
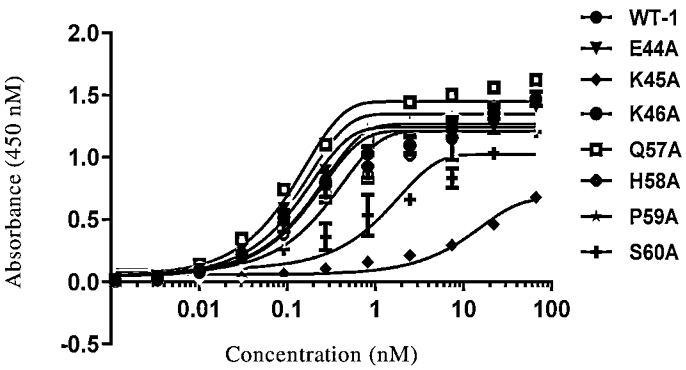
FIG. 20: Affinity of IL-33 mutant proteins (E44A, K45A, K46A, Q57A, H58A, P59A, S60A) to 874F7-Hu1.
Figure 21:
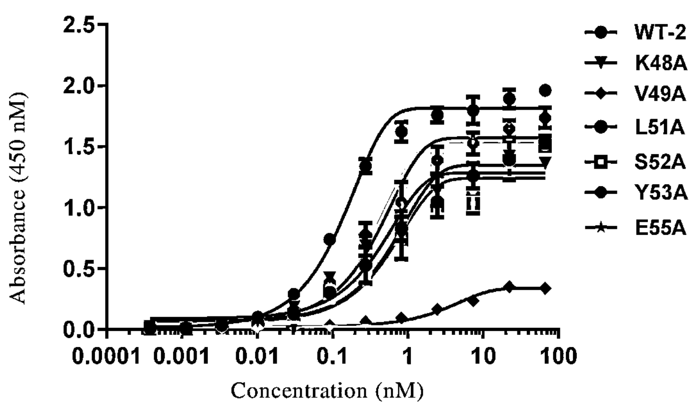
FIG. 21: Affinity of IL-33 mutant proteins (K48A, V49A, L51A, S52A, Y53A, E55A) to 874F7-Hu1.
Figure 22:
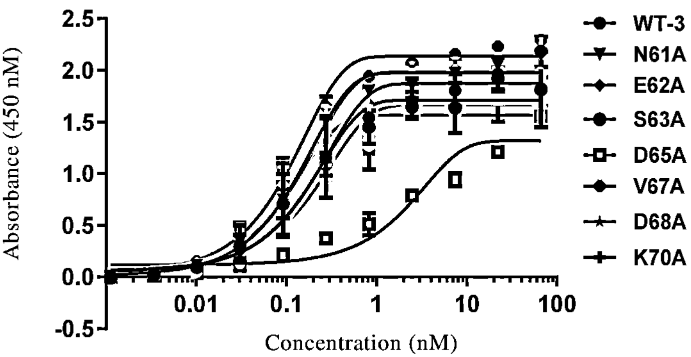
FIG. 22: Affinity of IL-33 mutant proteins (N61A, E62A, S63A, D65A, V67A, D68A, K70A) to 874F7-Hu1.
Figure 23:
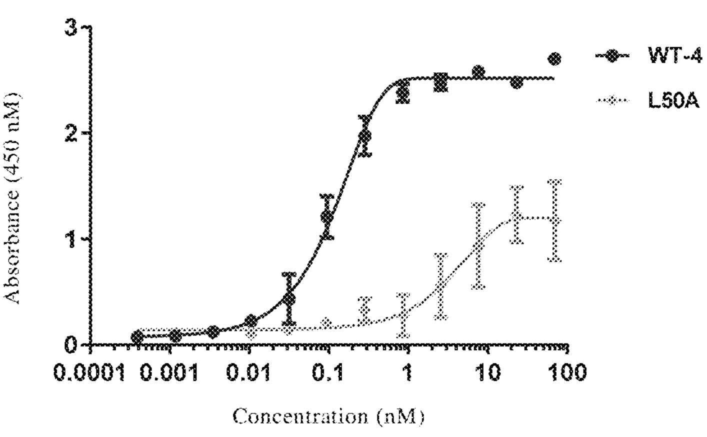
FIG. 23: Affinity of IL-33 mutant protein (L50A) to 874F7-Hu1.

The experimental results are shown in FIG. 19. Compared with the control group (without human IL-33 stimulation), after intraperitoneal injection of human IL-33, the increase of eosinophils in the peripheral blood of mice (IL-33 group) could be significantly stimulated by about 10.5 times, and when 5 mg/kg of 864F3-Hu4 and 874F7-Hu1 were administered for a single treatment, it could effectively reduce the increase of eosinophils caused by human IL-33 stimulation in the peripheral blood of mice, which were 1.6 times and 1.58 times that of the control group.

Example 22 Determination of Binding Epitopes of Humanized Antibodies to IL-33

According to the amino Amino acid sequence of IL-33 mature protein:

MSITGISPITEYLASLSTYNDQSITFALEDESYEIYVEDLKKDEKKDKVLLS YYESQHPSNESGDGVDGKMLMVTLSPTKDFWLHANNKEHSVELHKCEKPLP DQAFFVLHNMHSNCVSFECKTDPGVFIGVKDNHLALIKVDSSENLCTENILFK LSET (SEQ ID NO. 55) (The amino acid sequences were derived from Ser 112 to Thr 270 of NCBI: NP_254274.1), and the following 16 polypeptides were synthesized for the characterization of binding epitopes of humanized antibodies to IL-33. The amino acid sequences of each polypeptide were shown in Table 4, and the N-terminus of each polypeptide was biotinized.

TABLE 4

Amino acid sequences of polypeptides

| Poly-peptide name | Polypeptide sequence | SEQ ID NO. |
|---|---|---|
| Pep1 | Bio- VQKYTRALHDSSITGISPIT | 56 |
| Pep2 | Bio- SSITGISPITEYLASLSTYN | 57 |

TABLE 4-continued

Amino acid sequences of polypeptides

| Poly-peptide name | Polypeptide sequence | SEQ ID NO. |
|---|---|---|
| Pep3 | Bio- EYLASLSTYNDQSITFALED | 58 |
| Pep4 | Bio- DQSITFALEDESYEIYVEDL | 59 |
| Pep5 | Bio- ESYEIYVEDLKKDEKKDKVL | 60 |
| Pep6 | Bio- KKDEKKDKVLLSYYESQHPS | 61 |
| Pep7 | Bio- LSYYESQHPSNESGDGVDGK | 62 |
| Pep8 | Bio- NESGDGVDGKMLMVTLSPTK | 63 |
| Pep9 | Bio- MLMVTLSPTK DFWLHANNKE | 64 |
| Pep10 | Bio- DFWLHANNKE HSVELHKCEK | 65 |
| Pep11 | Bio- HSVELHKCEK PLPDQAFFVL | 66 |
| Pep12 | Bio- PLPDQAFFVL HNMHSNCVSF | 67 |
| Pep13 | Bio- HNMHSNCVSF ECKTDPGVFI | 68 |
| Pep14 | Bio- ECKTDPGVFI GVKDNHLALI | 69 |
| Pep15 | Bio- GVKDNHLALI KVDSSENLCT | 70 |
| Pep16 | Bio- KVDSSENLCT ENILFKLSET | 71 |

To determine the binding activity of antibody to each polypeptide fragment, the ELISA plate was pre-coated by biotin-avidin (SA) which was diluted in coating solution (50 mM carbonate coating buffer, pH 9.6) to 2 μg/ml at 4° C. overnight. The plate was washed with PBST for 3 times, and then blocked with 2% BSA prepared in PBS at room temperature for 2 h with 200 μL/well. The plate was washed once with PBST, and 864F3 and 874F7 with final concentrations of 10 μg/mL were added at 100 μL/well, respectively, and the plate was incubated at room temperature for 1 h. The plate was washed with PBST for 3 times, and the goat anti-mouse IgG labeled by HRP was added and placed at 37° C. for 30 min. After washing the plate with PBST for 3 times, the plate was patted on the absorbent paper to remove residual droplets as far as possible. 100 μl TMB developing solution was added to each well, and the plate was placed at room temperature (20±5° C.) for 5 minutes away from light; 50 μl 2M $H_2SO_4$ terminating solution was added to each well to terminate the substrate reaction. OD values were read at 450 nm on the microplate reader to analyze the binding ability of the antibody to each polypeptide fragment. The experimental results are shown in Table 5, indicating that 874F7 can significantly bind to Pep6 but not to other peptides.

TABLE 5

Amino acid sequences of polypeptides

| Peptide | Sample: 864F3 | | 874F7 | |
|---|---|---|---|---|
| Pep1 | 0.059 | 0.048 | 0.074 | 0.061 |
| Pep2 | 0.054 | 0.050 | 0.056 | 0.050 |
| Pep3 | 0.048 | 0.047 | 0.053 | 0.048 |
| Pep4 | 0.047 | 0.047 | 0.050 | 0.048 |
| Pep5 | 0.046 | 0.047 | 0.050 | 0.049 |

TABLE 5-continued

Amino acid sequences of polypeptides

| Peptide | Sample: 864F3 | | 874F7 | |
|---|---|---|---|---|
| Pep6 | 0.051 | 0.053 | 1.042 | 1.027 |
| Pep7 | 0.047 | 0.047 | 0.055 | 0.051 |
| Pep8 | 0.047 | 0.047 | 0.053 | 0.047 |
| Pep9 | 0.061 | 0.060 | 0.065 | 0.061 |
| Pep10 | 0.050 | 0.051 | 0.053 | 0.052 |
| Pep11 | 0.049 | 0.048 | 0.056 | 0.053 |
| Pep12 | 0.050 | 0.051 | 0.056 | 0.053 |
| Pep13 | 0.048 | 0.049 | 0.054 | 0.053 |
| Pep14 | 0.048 | 0.048 | 0.059 | 0.053 |
| Pep15 | 0.047 | 0.049 | 0.055 | 0.052 |
| Pep16 | 0.050 | 0.057 | 0.049 | 0.049 |

Based on the above experimental results, the Kd value of 874F7-Hu1 binding to mouse IL-33 protein is $3.32\times10^{-8}$; According to the amino acid sequence of the mature IL-33 protein, "KKDEKKDKVLLSYYESQHPSNESGDGVDGK" region (positions 41-70 of SEQ ID NO. 55) was selected for alanine scanning site-specific mutation by PCR (polymerase chain reaction), followed by prokaryotic expression and purification, and IL-33 mutant proteins with the following amino acid site mutations were obtained, respectively:

K41A, K42A, D43A, E44A, K45A, K46A, D47A, K48A, V49A, L50A, L51A, S52A, Y53A, Y54A, E55A, S56A, Q57A, H58A, P59A, S60A, N61A, E62A, S63A, D65A, V67A, D68A, K70A.

Subsequently, according to the experimental method of Example 9, the affinity of the above mutant proteins to 874F7-Hu1 was determined, and IL-33 proteins (WT-1, WT-2, WT-3, and WT-4) without any mutation were set as controls.

Representative experimental results are shown in FIGS. 20-23 and Table 6 respectively. It can be seen that, compared with WT, the affinity between 874F7-Hu1 and IL-33 is significantly reduced by more than 25 times after mutation of K45, V49, L50 and D65. After mutation of S60 and S52, the affinity between 874F7-Hu1 and IL-33 was significantly reduced by 10-25 times. After mutation of K48, L51, Y53 and E55, the affinity between 874F7-Hu1 and IL-33 was reduced to some extent, by 2.5-10 times. This also indicates that the key sites affecting the binding of 874F7-Hu1 to IL-33 are mainly K45, V49, D65, and L50, followed by S60, S52, and K48, L51, Y53, and E55.

Figure 24:
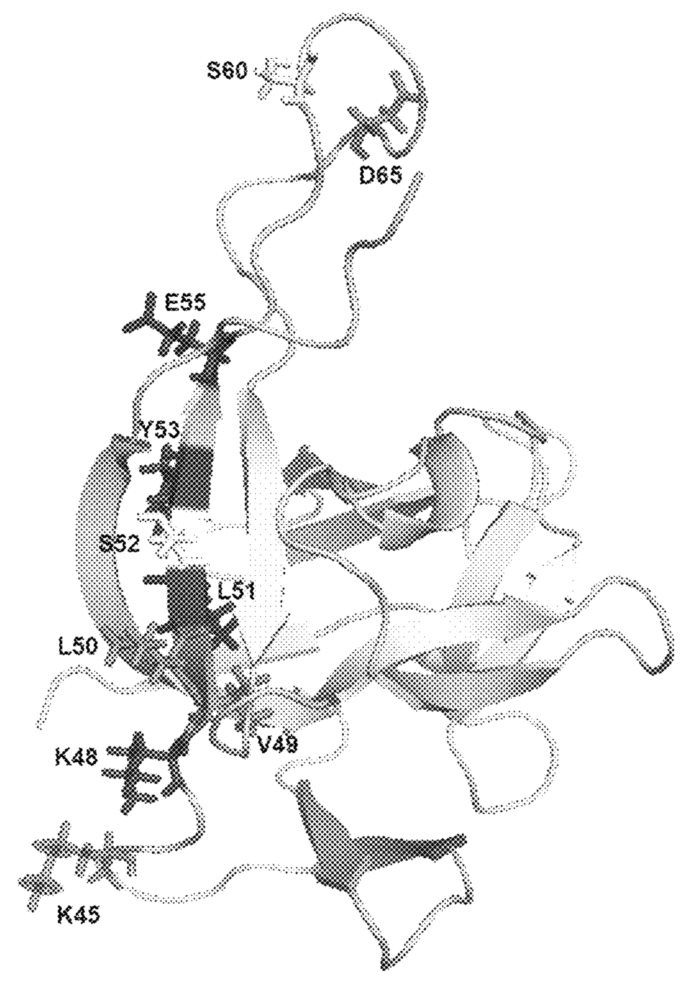
FIG. 24: Positions of key amino acid sites affecting 874F7-Hu1 binding in the 3D structure of IL-33 crystallization

The positions of the above sites in the 3D structure diagram of IL-33 crystallization (from PDB: 2KLL) are shown in FIG. 24, which further indicates that the binding epitopes of 874F7-Hu1 to IL-33 are linear and spatial epitopes comprising the above key amino acid sites.

TABLE 6

Binding affinity of 874F7-Hu1 to all IL-33 mutants

| Sample name | $EC_{50}$ (nM) | SD | Top value | Affinity decline ratio |
|---|---|---|---|---|
| WT-1 | 0.23 | 0.03 | 1.21 | 1.0 |
| E44A | 0.13 | 0.01 | 1.24 | 0.6 |
| K45A | \ | \ | 0.67 | >25 |
| K46A | 0.23 | 0.05 | 1.27 | 1.0 |
| Q57A | 0.12 | 0.01 | 1.45 | 0.5 |
| H58A | 0.43 | 0.23 | 1.21 | 1.9 |

TABLE 6-continued

Binding affinity of 874F7-Hu1 to all IL-33 mutants

| Sample name | $EC_{50}$ (nM) | SD | Top value | Affinity decline ratio |
|---|---|---|---|---|
| P59A | 0.12 | 0.00 | 1.35 | 0.5 |
| S60A | 5.31 | 0.62 | 1.02 | 23.2 |
| WT-2 | 0.13 | 0.00 | 1.81 | 1.0 |
| K48A | 0.49 | 0.29 | 1.28 | 3.7 |
| V49A | \ | \ | 0.34 | >25 |
| L51A | 0.91 | 0.52 | 1.35 | 6.8 |
| S52A | 1.96 | 1.31 | 1.24 | 14.6 |
| Y53A | 0.44 | 0.13 | 1.57 | 3.3 |
| E55A | 0.33 | 0.00 | 1.54 | 2.5 |
| WT-3 | 0.18 | 0.08 | 1.87 | 1.0 |
| N61A | 0.15 | 0.08 | 1.98 | 0.8 |
| E62A | 0.15 | 0.06 | 1.99 | 0.8 |
| S63A | 0.16 | 0.04 | 1.71 | 0.9 |
| D65A | 35.30 | 0.09 | 1.32 | 191.8 |

TABLE 6-continued

Binding affinity of 874F7-Hu1 to all IL-33 mutants

| Sample name | $EC_{50}$ (nM) | SD | Top value | Affinity decline ratio |
|---|---|---|---|---|
| V67A | 0.11 | 0.03 | 2.14 | 0.6 |
| D68A | 0.22 | 0.09 | 1.67 | 1.2 |
| K70A | 0.11 | 0.04 | 1.57 | 0.6 |
| WT-4 | 0.12 | 0.03 | 2.52 | 1.0 |
| L50A | 3.34 | 2.14 | 1.20 | 28.5 |

All literatures mentioned in the present application are incorporated herein by reference, as though each one is individually incorporated by reference. In addition, it should also be understood that, after reading the above teachings of the present invention, those skilled in the art can make various changes or modifications, and these equivalents also fall in the scope of claims as defined in the appended claims.

The invention claimed is:

1. A human IL-33 antibody or antigen-binding fragment thereof comprising:

(a) heavy chain complementarity determining regions H-CDR1, H-CDR2, and H-CDR3, having the amino acid sequences of SEQ ID NO: 15, 16, and 17, respectively, SEQ ID NO: 18, 19, and 20, respectively, or SEQ ID NO: 18, 24, and 25, respectively, and (b) light chain complementarity determining regions L-CDR1, L-CDR2, and L-CDR3, having the amino acid sequences of SEQ ID NO: 21, 22, and 23, respectively, SEQ ID NO: 26, 22, and 27, respectively, or SEQ ID NO: 26, 22, and 28, respectively.

2. The antibody or antigen-binding fragment thereof of claim 1, wherein the antibody is a murine antibody, a chimeric antibody, or a humanized antibody, or wherein the antigen-binding fragment comprises a Fab fragment, a $F(ab')_2$ fragment, or a Fv fragment.

3. The antibody or antigen-binding fragment thereof of claim 1, comprising a heavy chain variable region and a light chain variable region having the amino acid sequences of SEQ ID NO: 2 and SEQ ID NO: 6, respectively; SEQ ID NO: 8 and SEQ ID NO: 10, respectively; or SEQ ID NO: 4 and SEQ ID NO: 12, respectively.

4. The antibody or antigen-binding fragment thereof of claim 1, comprising:

(i) a light chain variable region having the amino acid sequence of SEQ ID NO: 32, and a heavy chain variable region having the amino acid sequence of SEQ ID NO: 29, 30, 31, 33, 34, or 35;

(ii) a light chain variable region having the amino acid sequence of SEQ ID NO: 40, and a heavy chain variable region having the amino acid sequence of SEQ ID NO: 37, 38, or 39; or (iii) a light chain variable region having the amino acid sequence of SEQ ID NO: 36, and a heavy chain variable region having the amino acid sequence of SEQ ID NO: 33, 34, or 35.

5. The antibody or antigen-binding fragment thereof of claim 1, further comprising a heavy chain constant region selected from the heavy chain constant regions of human IgG1, IgG2, IgG3, and IgG4.

6. The antibody or antigen-binding fragment thereof of claim 1, further comprising a heavy chain constant region and a light chain constant region having the amino acid sequence of SEQ ID NO: 13 and SEQ ID NO: 14, respectively.

7. The antibody or antigen-binding fragment thereof of claim 1, wherein the binding epitope of the antibody or antigen-binding fragment comprises one or more sites corresponding to SEQ ID NO: 55 selected from the group consisting of:

lysine at position 45 (K45), valine at position 49 (V49), aspartic acid at position 65 (D65), leucine at position 50 (L50), serine at position 60 (S60), serine at position 52 (S52), lysine at position 48 (K48), leucine at position 51 (L51), tyrosine at position 53 (Y53), and glutamic acid at position 55 (E55).

8. The antibody or antigen-binding fragment thereof of claim 1, having one or more of the following characteristics:

(1) blocking the binding of IL-33 to receptor ST2;

(2) inhibiting IL-6 secretion of HUVEC cells induced by IL-33;

(3) inhibiting IFNγ secretion of human PBMCs induced by IL-33 protein;

(4) inhibiting IFNγ secretion of NK cells induced by IL-33; and (5) inhibiting IL-5 and IL-13 secretion of KU812 cells induced by IL-33.

9. A nucleotide molecule encoding the antibody or antigen-binding fragment thereof of claim 1.

10. The nucleotide molecule of claim 9, further comprising the following nucleotide sequences encoding the heavy chain variable region and light chain variable region: (i) SEQ ID NO: 1 and SEQ ID NO: 5, respectively; (ii) SEQ ID NO: 3 and SEQ ID NO: 5, respectively; (iii) SEQ ID NO: 7 and SEQ ID NO: 9, respectively; or (iv) SEQ ID NO: 3 and SEQ ID NO: 11, respectively.

11. The nucleotide molecule of claim 9, wherein the nucleotide sequence encoding the heavy chain variable region comprises SEQ ID NO: 41, 42, 43, 45, 46, or 47, and the nucleotide sequence encoding the light chain variable region comprises SEQ ID NO: 44.

12. The nucleotide molecule of claim 9, wherein the nucleotide sequence encoding the heavy chain variable region comprises SEQ ID NO: 49, 50, or 51, and the nucleotide sequence encoding the light chain variable region comprises SEQ ID NO: 52.

13. The nucleotide molecule of claim 9, wherein the nucleotide sequence encoding the heavy chain variable region comprises SEQ ID NO: 45, 46, or 47, and the nucleotide sequence encoding the light chain variable region comprises SEQ ID NO: 48.

14. An expression vector comprising the nucleotide molecule of claim 9.

15. A host cell comprising the expression vector of claim 14.

16. A method for preparing an antibody binding to human IL-33 or antigen-binding fragment thereof, which comprises the following steps:

(a) culturing the host cell of claim 15 under conditions suitable for expression to express the antibody or antigen-binding fragment thereof;

(b) isolating and purifying the antibody or antigen-binding fragment thereof in step (a).

17. A composition comprising the antibody or antigen-binding fragment thereof of claim 1 and a pharmaceutically acceptable carrier.

18. An antibody-drug conjugate, which comprises:

(a) an antibody moiety, which comprises the antibody or antigen-binding fragment thereof of claim 1; and (b) a coupling moiety coupled to the antibody moiety, which is selected from the group consisting of a detectable label, a drug, a toxin, a cytokine, a radionuclide, an enzyme, and a combination thereof.

19. A method for treating asthma, arthritis, specific reactive/allergic dermatitis, chronic sinusitis, chronic obstructive pulmonary disease (COPD), systemic sclerosis, liver fibrosis, psoriasis, ulcerative colitis, Crohn's disease, multiple sclerosis, diabetic kidney disease, inflammatory bowel disease, psoriasis, eosinophilic esophagitis, diabetic macular edema, age-related macular degeneration, xerophthalmus, or tumors, which comprises: administering to a subject in need thereof with the antibody or antigen-binding fragment thereof of claim 1, a composition comprising the antibody or the antigen-binding fragment thereof of claim 1, an antibody-drug conjugate of the antibody or the antigen-fragment thereof of claim 1, or a combination thereof.

* * * * *